(12) United States Patent
Wu et al.

(10) Patent No.: US 7,972,596 B2
(45) Date of Patent: Jul. 5, 2011

(54) ANTIBODIES AGAINST VASCULAR ENDOTHELIAL GROWTH FACTOR RECEPTOR-1

(75) Inventors: Yan Wu, Flemington, NJ (US); Danny J. Hicklin, Montclair, NJ (US); Peter Bohlen, New York, NY (US)

(73) Assignee: ImClone LLC, New York, NY (US)

( * ) Notice: Subject to any disclaimer, the term of this patent is extended or adjusted under 35 U.S.C. 154(b) by 38 days.

(21) Appl. No.: 11/719,677

(22) PCT Filed: Nov. 18, 2005

(86) PCT No.: PCT/US2005/041904
§ 371 (c)(1),
(2), (4) Date: Oct. 6, 2009

(87) PCT Pub. No.: WO2006/055809
PCT Pub. Date: May 26, 2006

(65) Prior Publication Data
US 2010/0028347 A1 Feb. 4, 2010

(51) Int. Cl.
*A61K 39/395* (2006.01)
*C12P 21/08* (2006.01)
*C07K 16/18* (2006.01)
*C07K 16/28* (2006.01)

(52) U.S. Cl. .............. 424/130.1; 424/141.1; 424/143.1; 530/387.1; 530/388.15; 530/388.22

(58) Field of Classification Search .................. None
See application file for complete search history.

(56) References Cited

U.S. PATENT DOCUMENTS

| | | |
|---|---|---|
| 4,683,295 A | 7/1987 | Carson |
| 4,714,680 A | 12/1987 | Civin |
| 4,946,778 A | 8/1990 | Ladner et al. |
| 4,965,204 A | 10/1990 | Civin |
| 5,061,620 A | 10/1991 | Tsukamoto et al. |
| 5,130,144 A | 7/1992 | Civin |
| 5,185,438 A | 2/1993 | Lemischka |
| 5,270,458 A | 12/1993 | Lemischka |
| 5,283,354 A | 2/1994 | Lemischka |
| 5,367,057 A | 11/1994 | Lemischka |
| 5,530,101 A | 6/1996 | Queen et al. |
| 5,543,503 A | 8/1996 | Chuntharapai et al. |
| 5,548,065 A | 8/1996 | Lemischka |
| 5,558,864 A | 9/1996 | Bendig et al. |
| 5,621,090 A | 4/1997 | Lemischka |
| 5,710,134 A | 1/1998 | Bosslet et al. |
| 5,747,651 A | 5/1998 | Lemischka |
| 5,837,242 A | 11/1998 | Holliger et al. |
| 5,840,301 A | 11/1998 | Rockwell et al. |
| 5,851,999 A | 12/1998 | Ullrich et al. |
| 5,861,301 A | 1/1999 | Terman et al. |
| 5,861,499 A | 1/1999 | Rockwell et al. |
| 5,874,542 A | 2/1999 | Rockwell et al. |
| 5,912,133 A | 6/1999 | Lemischka |
| 5,955,311 A | 9/1999 | Rockwell et al. |
| 6,004,554 A | 12/1999 | Thorpe et al. |
| 6,075,181 A | 6/2000 | Kucherlapati et al. |
| 6,297,238 B1 | 10/2001 | Doyle et al. |
| 6,342,219 B1 | 1/2002 | Thorpe et al. |
| 6,365,157 B2 | 4/2002 | Rockwell et al. |
| 6,448,077 B1 | 9/2002 | Rockwell et al. |
| 6,448,277 B2 | 9/2002 | Altmann et al. |
| 6,811,779 B2 | 11/2004 | Rockwell et al. |
| 6,960,446 B2 | 11/2005 | Lemischka |
| 2001/0021382 A1 | 9/2001 | Ferrara et al. |
| 2003/0018545 A1 | 1/2003 | Yonezawa et al. |
| 2004/0259156 A1 | 12/2004 | Zhu |
| 2005/0004066 A1 | 1/2005 | Rockwell et al. |
| 2006/0189608 A1 | 8/2006 | Bingaman |
| 2007/0142401 A1 | 6/2007 | Auberson et al. |

FOREIGN PATENT DOCUMENTS

| | | |
|---|---|---|
| CA | 2085291 | 1/1994 |
| EP | 0239400 | 9/1987 |
| EP | 0317156 | 5/1989 |
| EP | 0330191 | 8/1989 |
| EP | 332424 | 9/1989 |
| EP | 0332424 | 9/1989 |
| EP | 338745 | 10/1989 |
| EP | 0395355 | 10/1990 |

OTHER PUBLICATIONS

Urbich et al., Circulation Research 95:343-353 (2004).
Urlab and Chasm, PNAS 77:4216 (1980).
Von Heinje et al., Nucl. Acids Res.14:4683-4690 (1986).
Wade, Nicholas, "Brain Stem Cell is Discovered Twice" New York Times, (Jun. 1, 1996).
Waldmann, Science, 252: 1657-1662, (Jun. 1991).
Wek et al., Proc. Nat'l Acad. Sci, USA, 86: 4579-4583 (1989).
Wikstrand et al., Cancer Res. 55:3140-48 (1995).
Wilks, PNAS 86:1603-1607 Mar. 1989.
Williams et al., Cell 63, 163-174 (1990).
Winters, et al., TIPS, 14: 139-143, (May 1993).
Yamaguchi, et al., Development 118:489-98 (1993).
Yang et al., J. Mol. Bio. 254:392-403 (1995).
Yang et al., J. Neuroscience 16:6089-99(1996).
Zhu et al., Cancer Research 58: 3209-3214 (1998).
Zhu, Z. et al., Cancer Lett. 136:203-213 (1999).
Zipori, Int'l. Journal of Cell Cloning, 7: 281-291 (1989).
Morrison, S.L. et al., Proc. Natl. Acad. Sci. USA 81:6851-6855 (Nov. 1984).
Mould, et al., Arthritis Rheum. 48:2660-2669 (2003).
Moulton et al., Circulation, 99:1726-32 (1999).

(Continued)

*Primary Examiner* — Phuong Huynh
(74) *Attorney, Agent, or Firm* — Averie K. Hason

(57) ABSTRACT

Monoclonal antibodies that are specific for vascular endothelial growth factor receptor 1 (VEGFR-I). This invention also provides nucleotide sequences encoding and amino acid sequences comprising variable heavy and light chain immunoglobulin molecules, including sequences corresponding to the complementarity determining regions of CDR1, CDR2, and CDR3. The invention also provides methods for generation and expression of anti -VEGFR-I antibodies and methods of treating angiogenic-related disorders and reducing tumor growth by administering anti-VEGFR-I antibodies.

6 Claims, 33 Drawing Sheets

OTHER PUBLICATIONS

Nakamura, et al, Ex Vivo Generation of CD34+ cells from CD34- Hematopoietic cells, 94(12): 4053-4059, Dec. 15, 1999.
Ngo et al., In the Protein Folding Problem and Tertiary Structure Prediction Edited by Merz and Le Grand, Birkhauser, Boston 1994, pp. 433-506.
Nocka et al., Candidate ligand for the C-kit transmembrane Kinase receptor: KL, a fibroblast derived growth factor stimulates mast cells and erythroid progenitors, 9(10): 3287-3294, 1990.
Nocka, K. et al., Expression of C-Kit gene products in known cellular targets of W mutations in normal and W mutant mice-evidence for an impaired C-Kit Kinase in mutant mice, Genes and Development, 3(6): 739-920, 1989.
Orr, Genetic Engineering News, p. 8, (Feb. 1991).
Panek et al., J. Pharmacol. and Exp. Therapeutics 283:1433-44 (1997).
Parham, J. Immunol. 131:2895-2902 (1983).
Pearson and Lipman PNAS 85:2444-8 (1988).
Pepper, Michael, S., Manipulating Angiogenesis Arteriosclerosis, Thrombosis, and Vascular Biology 17, 605-619 (1997).
Petit et at. American Journal of Pathology. 151 (6): 1523-1530,1997.
Petrides et al., CancerRes. 50:3934-39 (1990).
Plate et al., Cancer Research 53:5822-5827 (Dec. 1, 1993).
Plate, Journal of Neuropathology and Exprimental Neurology 58(4):313-320 (1999).
Prewett et al., Cancer Research, 59: 5209-5218, 1999.
Price et al., Cell Growth and Bifferentiation, 12:129-35, (Mar. 2001).
Radinsky et al., Clin. Cancer Res. 1:19-31 (1995).
Raffi et al., Nature Medicine 9(6):702-712 (2003).
Raffi, S. et al. Blood, Rapid Communication, 84(1): 10-19 (1994).
Ray and Diamond, PNAS. 91:5548-51, 1994.
Robb, et al., Bioessays 20:611-4 (1998).
Rockwell et al., Molecular and Cellular Differentiation 3:315-335 (1995).
Rockwell et al., Molecular and Cellular Differentiation 3:91-109 (1995).
Rosnet et al., Oncogene 6, 1641-1650 (1991).
Rosnet, Genomic 9, 380-385 (1991).
Sambrook et al., Molecular Cloning: A Laboratory Manual, 2nd Ed, Cold Spring Harbor Laboratory Press (1989).
Sarzani et al., Biochem Biophys Res Comm. 186(2) 706-714 Jul. 31, 1992.
Sauter et al., Am. J Path. 148:1047-53 (1996).
Scahill et al., PNAS 80:4654-4659 (1983).
Seimeister et al. Cancer and Metastasis Reviews 17: 241-248, 1998.
Peichev, et al., Expression of VEGFR-2 and AC133 by circulating human CD34+ cells identifies a population of functional endothelial precursors, Blood 95(3) 952-958 (2000).

Figure 1. Amino acid sequence of the human anti-VEGFR-1 antibodies

6F9-Light chain
METPAQLLFLLLLWLPESTGEIVLTQSPGTLSLSPGERATLSC<u>RASQSGSSSYLA</u>WYQQKPGQAPRLLIY
                                                                                                     CDR1
<u>GASSRAT</u>GIPDRFSGSGSGTDFTLTISRLEPEDFAVYYC<u>QQYGSSPLT</u>FGGGTKVEIKRTVAAPSVFIFP
    CDR2                                                   CDR3

6F9-Heavy chain
MEFGLSWVFLVALLRGVQCQVQLVESGGGVVQPGRSLRLSCAAS<u>GFTFSSYGMH</u>WVRQAPGKGLEW
                                                                               CDR1
VA<u>VIWYDGSNKYYADSVKG</u>RFTISRDNSKNTVYLQMNSLRAEDTAVYHCTRD<u>HFGSGAHYYYYGMD</u>
<u>V</u>
      CDR2                                                                              CDR3
WGQGTTVTVSS

13G12-Light chain
METPAQLLFLLLLWLPESTGEIVLTQSPGTLSLSPGERATLSC<u>RASQSGSSSYLA</u>WYQQKPGQAPRLLIY
                                                                      CDR1
<u>GASSRAT</u>GIPDRFSGSGSGTDFTLTISRLEPEDFAVYYC<u>QQYGSSPLT</u>FGGGTKVEIKRTVAAPSVFIFP
    CDR2                                                  CDR3

13G12-Heavy chain
MEFGLSWVFLVALLRGVQCQVQLVESGGGVVQPGRSLRLSCAAS<u>GFTFSSYGMH</u>WVRQAPGKGLEW
                                                                           CDR1
VA<u>VIWYDGSNKYYADSVKG</u>RFTISRDNSKNTLYLQMNSLRAEDTAVYYCARD<u>HYGSGAHYYYYGMD</u>
<u>V</u>
      CDR2                                                                    CDR3
WGQGTTVTVSS

15F11-Light chain
MEAPAQLLFLLLLWLPDTTGEIVLTQSPGTLSLSPGERATLSC<u>RASQSVSSSYLA</u>WYQQKPGQAPRLLIY
                                                                     CDR1
<u>GASSRAT</u>GIPDRFSGSGSGTDFTLTISRLEPEDFAVYYC<u>QQYGSSPLT</u>FGQGTRLEIKRTVAAPSVFIFP
    CDR2                                                 CDR3

15F11-Heavy chain
MEFGLSWVFLVALLRGVQCQVQLVESGGGVVQPGRSLRLSCAAS<u>GFTFSSYGMH</u>WVRQAPGKGLEW
                                                                             CDR1
VA<u>VIWFDGSNKYYADSVKG</u>RFTISRDNSKNTLYLQMNSLRAEDTAVYYCARD<u>HYGSGAHSYYYYGLDV</u>
        CDR2                                                                          CDR3
WGQGTSVTVSS

18F1-Light chain
METPAQLLFLLLLWLPDTTGEIVLTQSPGTLSLSPGERATLSC<u>RASQSVSSSYLA</u>WYQQKPGQAPRLLIY
                                                                     CDR1
<u>GASSRAT</u>GIPDRFSGSGSGTDFTLTISRLEPEDFAVYYC<u>QQYGSSPLT</u>FGGGTKVEIKRTVAAPSVFIFP
    CDR2                                               CDR3

18F1-Heavy chain
MEFGLSWVFLVALLRGVQCQAQVVESGGGVVQSGRSLRLSCAAS<u>GFAFSSYGMH</u>WVRQAPGKGLE
W
                                                                               CDR1
VA<u>VIWYDGSNKYYADSVRG</u>RFTISRDNSENTLYLQMNSLRAEDTAVYYCARD<u>HYGSGVHHYFYYGLDV</u>
        CDR2                                                                         CDR3
WGQGTTVTVSS

Figure 2. Nucleotide sequence of the human anti-VEGFR-1 antibodies

```
6F9-Light chain
ATGGAAACCCCAGCGCAGCTTCTCTTCCTCCTGCTACTCTGGCTCCCAGAAAGCACCGGAGAAATTGTGTTGACGC
AGTCTCCAGGCACCCTGTCCTTGTCTCCAGGGGAAAGAGCCACCCTCTCCTGCAGGGCCAGTCAGAGTGGTAGCAG
CAGCTACTTAGCCTGGTACCAGCAGAAACCTGGCCAGGCTCCCAGGCTCCTCATCTATGGTGCATCCAGCAGGGCC
ACTGGCATCCCAGACAGGTTCAGTGGCAGTGGGTCTGGGACAGACTTCACTCTCACCATCAGCAGACTGGAGCCTG
AAGATTTTGCAGTGTATTACTGTCAGCAGTATGGTAGCTCACCGCTCACTTTCGGCGGAGGGACCAAGGTGGAGAT
CAAACGAACTGTGGCTGCACCATCTGTCTTCATCTTCCCG 6F9-Heavy chain
ATGGAGTTTGGGCTGAGCTGGGTTTTCCTCGTTGCTCTTTTAAGAGGTGTCCAGTGTCAGGTGCAGCTGGTGGAGT
CTGGGGGAGGCGTGGTCCAGCCTGGGAGGTCCCTGAGACTCTCCTGTGCAGCGTCTGGATTCACCTTCAGTAGTTA
TGGCATGCACTGGGTCCGCCAGGCTCCAGGCAAGGGGCTGGAGTGGGTGGCAGTTATATGGTATGATGGAAGTAAT
AAATACTATGCAGACTCCGTGAAGGGCCGATTCACCATCTCCAGAGACAATTCCAAGAACACGGTGTATCTGCAAA
TGAACAGCCTGAGAGCCGAGGACACGGCTGTGTATCACTGTACGAGAGATCACTTTGGTTCGGGGCTCACTACTA
CTACTACTACGGTATGGACGTCTGGGGCCAAgggACCACGGTCACCGTCTCCTCA 13G12-Light chain
ATGGAAACCCCAGCGCAGCTTCTCTTCCTCCTGCTACTCTGGCTCCCAGAAAGCACCGGAGAAATTGTGTTGACGC
AGTCTCCAGGCACCCTGTCCTTGTCTCCAGGGGAAAGAGCCACCCTCTCCTGCAGGGCCAGTCAGAGTGGTAGCAG
CAGCTACTTAGCCTGGTACCAGCAGAAACCTGGCCAGGCTCCCAGGCTCCTCATCTATGGTGCATCCAGCAGGGCC
ACTGGCATCCCAGACAGGTTCAGTGGCAGTGGGTCTGGGACAGACTTCACTCTCACCATCAGCAGACTGGAGCCTG
AAGATTTTGCAGTGTATTACTGTCAGCAGTATGGTAGCTCACCGCTCACTTTCGGCGGAGGGACCAAGGTGGAGAT
CAAACGAACTGTGGCTGCACCATCTGTCTTCATCTTCCCG 13G12-Heavy chain
ATGGAGTTTGGGCTGAGCTGGGTTTTCCTCGTTGCTCTTTTAAGAGGTGTCCAGTGTCAGGTGCAGCTGGTGGAGT
CTGGGGGAGGCGTGGTCCAGCCTGGGAGGTCCCTGAGACTCTCCTGTGCAGCGTCTGGATTCACCTTCAGTAGCTA
TGGCATGCACTGGGTCCGCCAGGCTCCAGGCAAGGGGCTGGAGTGGGTGGCAGTTATATGGTATGATGGAAGTAAT
AAATACTATGCAGACTCCGTGAAGGGCCGATTCACCATCTCCAGAGACAATTCCAAGAACACGCTGTATCTGCAAA
TGAACAGCCTGAGAGCCGAGGACACGGCTGTGTATTACTGTGCGAGAGATCACTATGGTTCGGGGCTCACTACTA
CTACTACTACGGTATGGACGTCTGGGGCCAAGGGACCACgGTCACCGTCTCCTCA 15F11-Light chain
ATGGAAGCCCCAGCGCAGCTTCTCTTCCTCCTGCTACTCTGGCTCCCAGATACCACCGGAGAAATTGTGTTGACGC
AGTCTCCAGGCACCCTGTCTTTGTCTCCAGGGGAAAGAGCCACCCTCTCCTGCAGGGCCAGTCAGAGTGTTAGCAG
CAGCTACTTAGCCTGGTACCAGCAGAAACCTGGCCAGGCTCCCAGGCTCCTCATCTATGGTGCATCCAGCAGGGCC
ACTGGCATCCCAGACAGGTTCAGTGGCAGTGGGTCTGGGACAGACTTCACTCTCACCATCAGCAGACTGGAGCCTG
AAGATTTTGCAGTGTATTACTGTCAGCAGTATGGTAGCTCACCCTCTCACCTTCGGCCAAGGGACACGACTGGAGAT
TAAACGAACTGTGGCTGCACCATCTGTCTTCATCTTCCCG 15F11-Heavy chain
ATGGAGTTTGGGCTGAGCTGGGTTTTCCTCGTTGCTCTTTTAAGAGGTGTCCAGTGTCAGGTGCAGCTGGTGGAGT
CTGGGGGAGGCGTGGTCCAGCCTGGGAGGTCCCTGAGACTCTCCTGTGCAGCGTCTGGATTCACCTTCAGTAGCTA
TGGCATGCACTGGGTCCGCCAGGCTCCAGGCAAGGGGCTGGAGTGGGTGGCAGTTATATGGTTTGATGGAAGTAAT
AAATACTATGCAGACTCCGTGAAGGGCCGATTCACCATCTCCAGAGACAATTCCAAGAACACGCTGTATCTGCAAA
TGAACAGCCTGAGAgCCGAGGACACGGCTGTGTATTACTGTGCGAGAGATCACTATGGTTCGGGGCTCACTCCTA
CTACTACTACGGTTTGGACGTTTGGGGCCAAGGGACCTCGGTCACCGTCTCCTCA 18F1-Light chain
ATGGAAACCCCAGCGCAGCTTCTCTTCCTCCTGCTACTCTGGCTCCCAGATACCACCGGAGAAATTGTGTTGACGC
AGTCTCCAGGCACCCTGTCTTTGTCTCCAGGGGAAAGAGCCACCCTCTCCTGCAGGGCCAGTCAGAGTGTTAGCAG
CAGCTACTTAGCCTGGTACCAGCAGAAACCTGGCCAGGCTCCCAGGCTCCTCATCTATGGTGCATCCAGCAGGGCC
ACTGGCATCCCAGACAGGTTCAGTGGCAGTGGGTCTGGGACAGACTTCACTCTCACCATCAGCAGACTGGAGCCTG
AAGATTTTGCAGTGTATTACTGTCAGCAGTATGGTAGCTCACCGCTCACTTTCGGCGGAGGGACCAAGGTGGAGAT
CAAACGAACTGTGGCTGCACCATCTGTCTTCATCTTTCCG 18F1-Heavy chain
ATGGAGTTTGGGCTGAGCTGGGTTTTCCTCGTTGCTCTTTTAAGAGGTGTCCAGTGTCAGGCGCAGGTGGTGGAGT
CTGGGGGAGGCGTGGTCCAGTCTGGGAGGTCCCTGAGACTCTCCTGTGCAGCGTCTGGATTCGCCTTCAGTAGCTA
CGGCATGCACTGGGTCCGCCAGGCTCCAGGCAAGGGGCTGGAGTGGGTGGCAGTTATATGGTATGATGGAAGTAAT
AAATACTATGCAGACTCCGTGAGGGGCCGATTCACCATCTCCAGAGACAATTCCGAGAACACGCTGTATCTGCAAA
TGAACAGCCTGAGAGCCGAGGACACCGCTGTATATTACTGTGCCAGAGATCACTATGGTTCGGGGGTGCACCACTA
TTTCTACTACGGTCTGGACGTCTGGGGCCAAGGGACCACGGTCACCGTCTCCTCA
```

Figure 6
Figure 6A
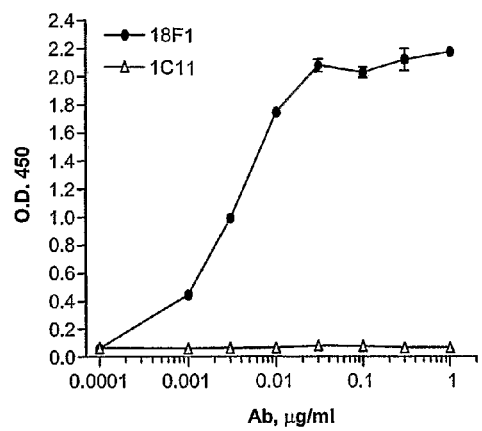
Figure 6B
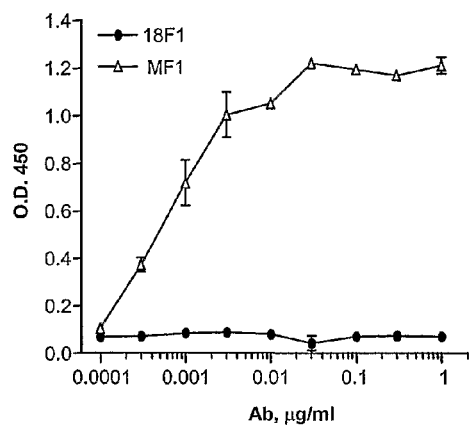
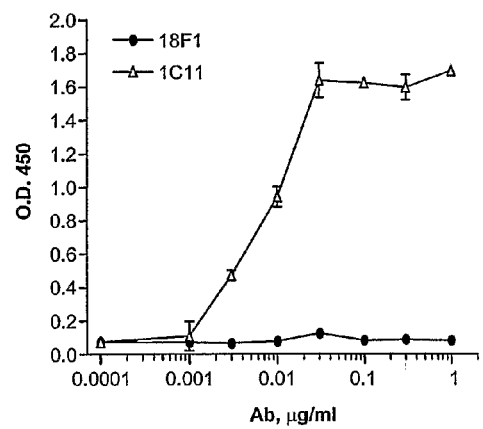
Figure 6C
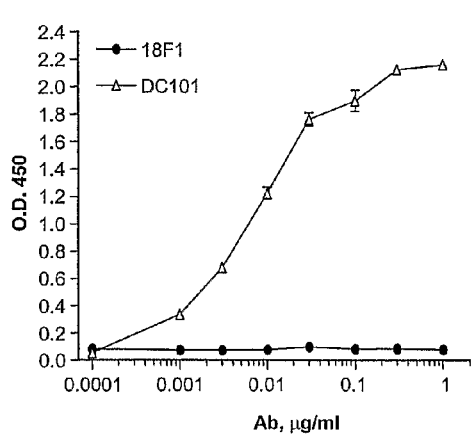
Figure 6D

Figure 8
Figure 8A
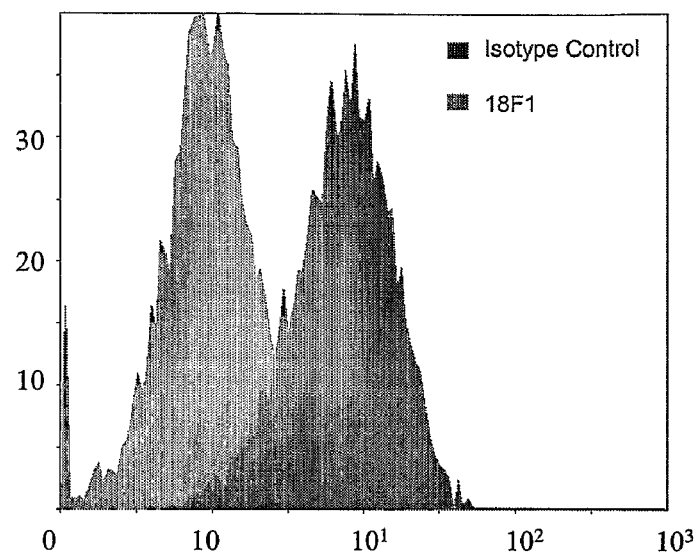
Figure 8B
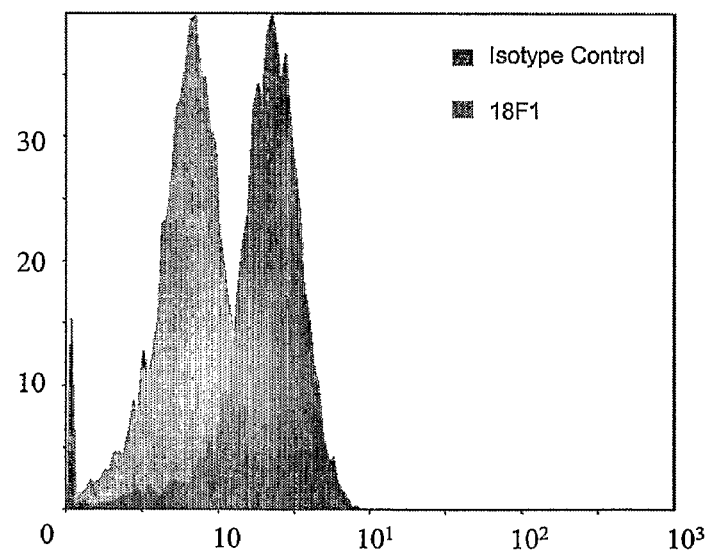

Figure 14
Figure 14A
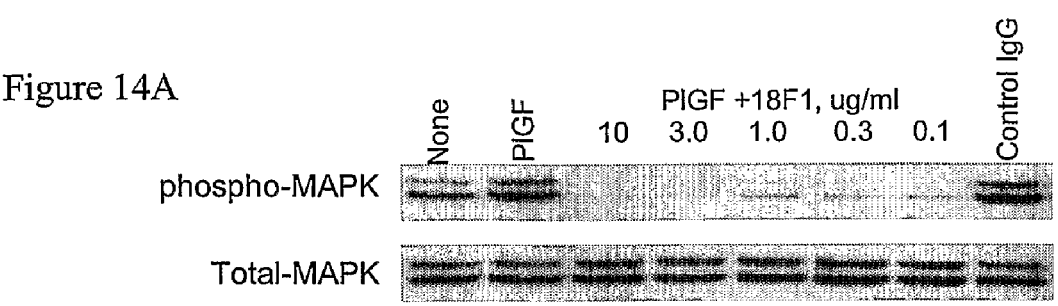
Figure 14B
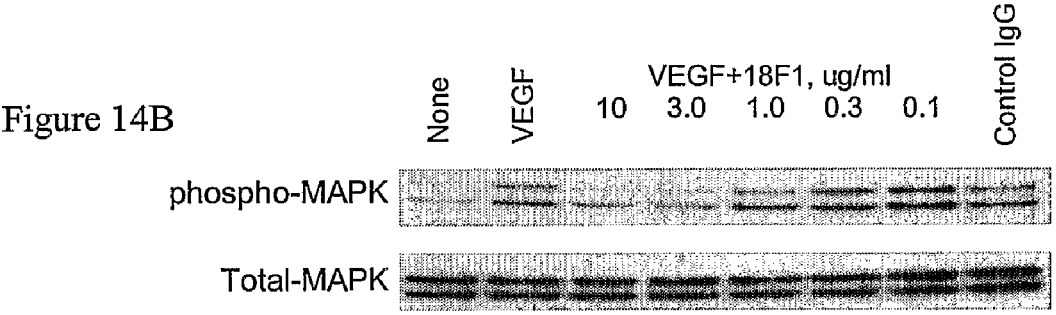

Figure 18
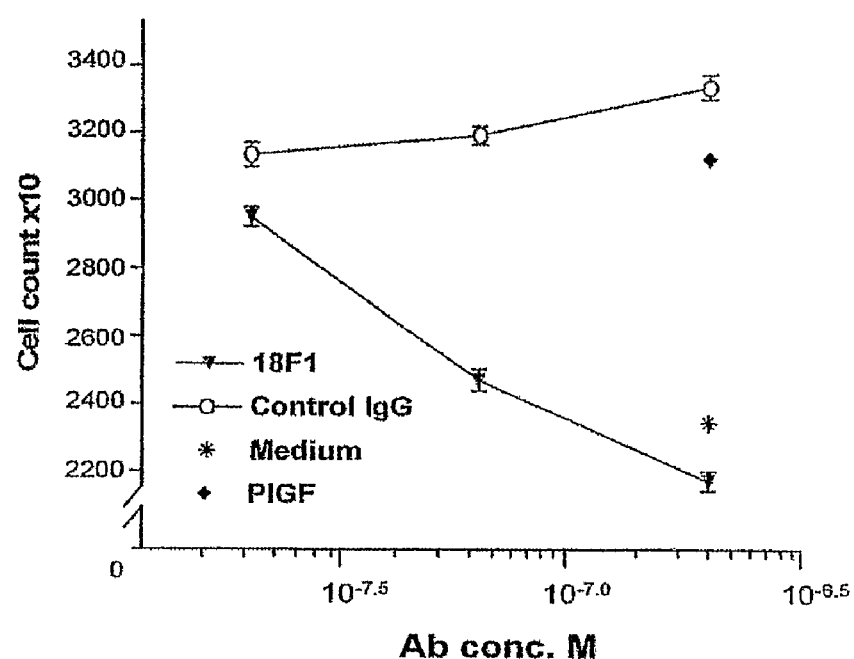
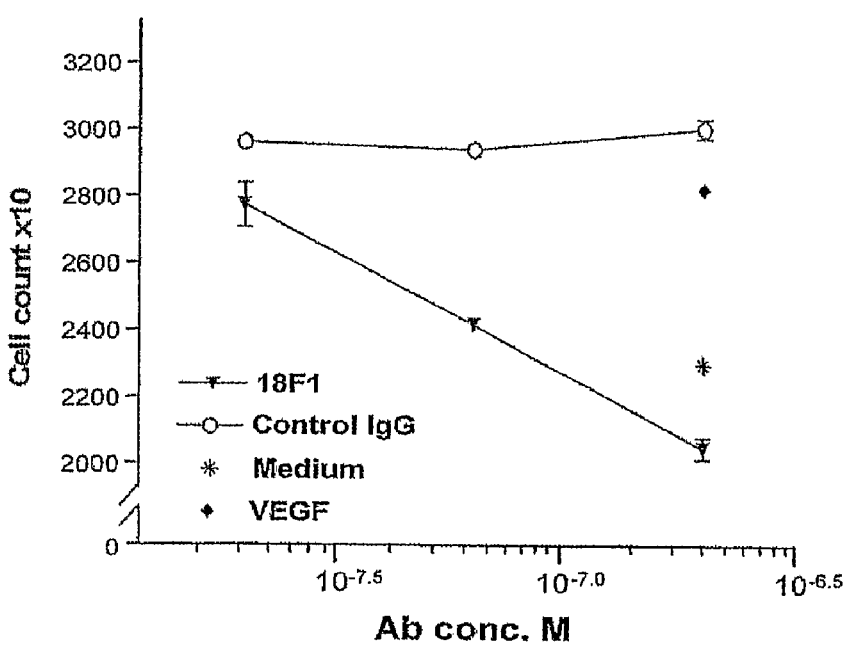

Figure 20
Figure 20A
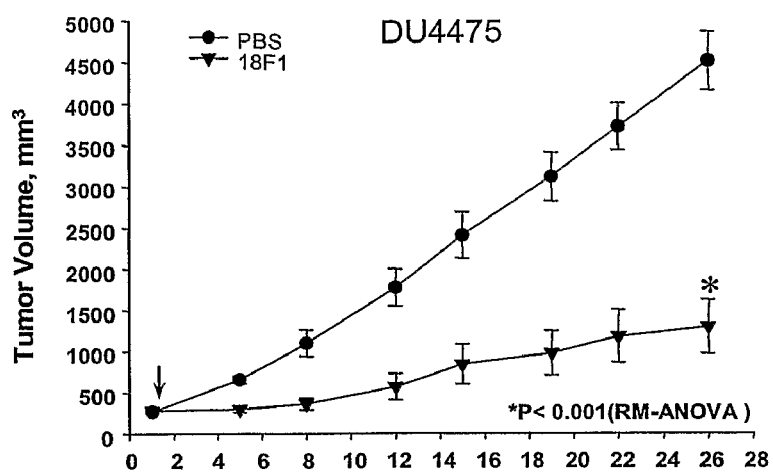
Figure 20B
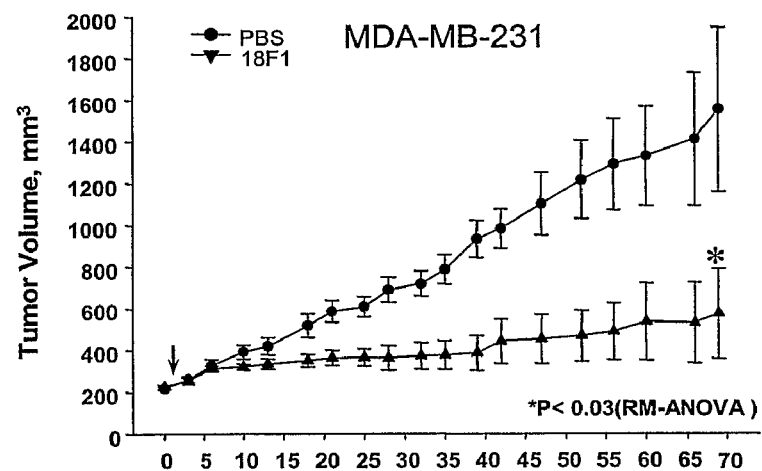
Figure 20C
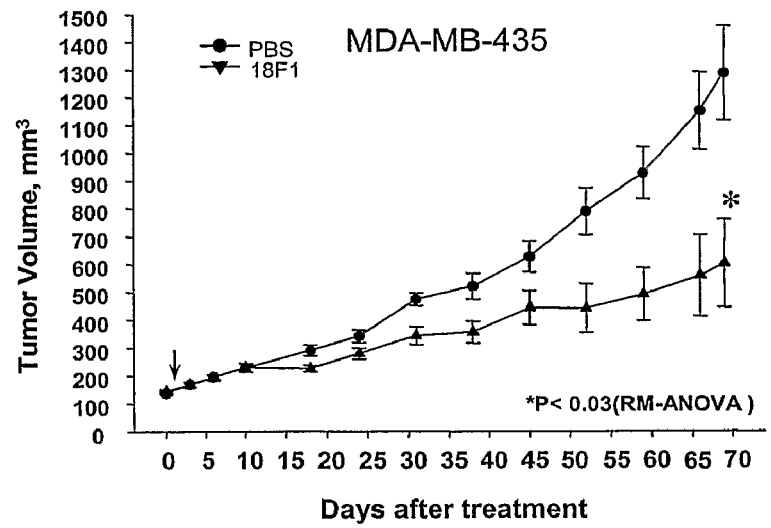
Days after treatment Figure 21
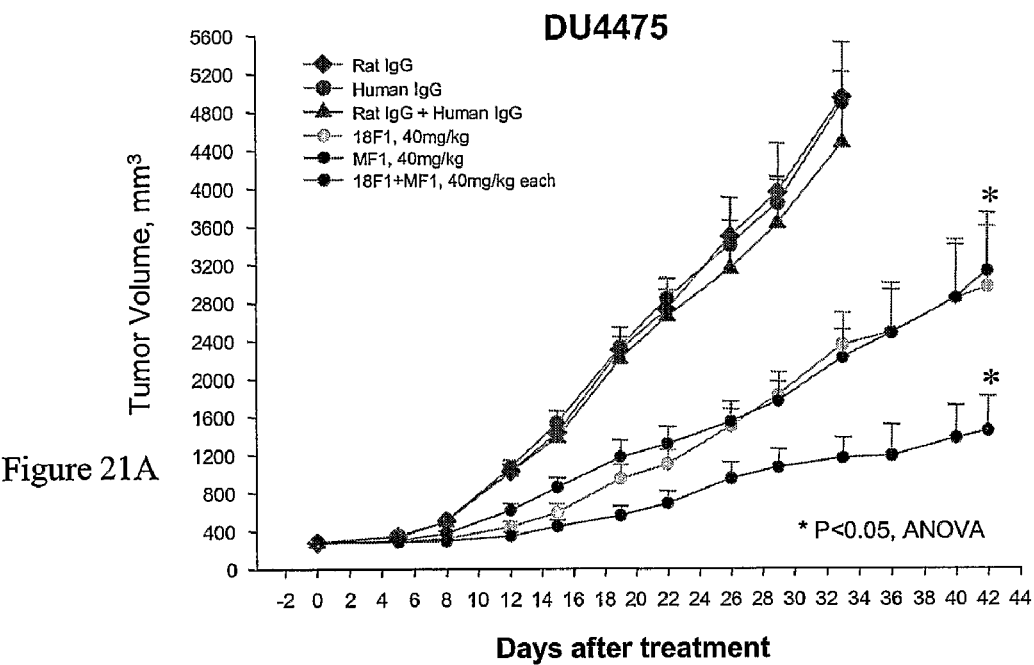
Figure 21A
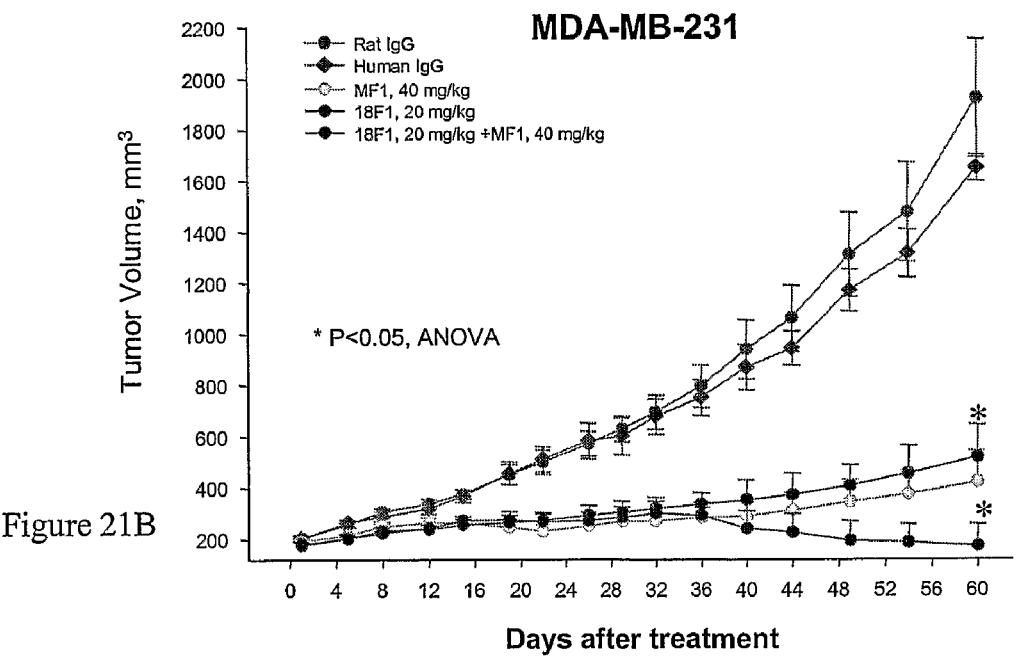
Figure 21B Figure 22: Inhibition of Tumor Cell Colony Formation. HT29 tumor cells were seeded in medium containing soft agar with or without 18F1 in the presence of VEGF-A or VEGF-B and incubated for 14 days. Colonies were counted under microscope. Treatment with 18F1 decreased colony formation induced by the VEGF ligands (*$P < 0.03$). Bars indicate SEM. Data from Pavco et al; Clin. Cancer Res. 2000; 6:2094-103.

Figure 23A and B: Inhibition of Tumor Cell Migration. (A) HT-29 tumor cells were treated with 18F1 in the presence of VEGF-A or VEGF-B for 48 hours. Cell migration across a layer of Matrigel is plotted as Mean ± SEM (*$P < 0.0001$). (B) Photomicrographs of migrated cells stained with Diff-Quik. Data from Pavco *et al*; Clin. Cancer Res. 2000; 6:2094-103.

Figure 24
Figure 24A
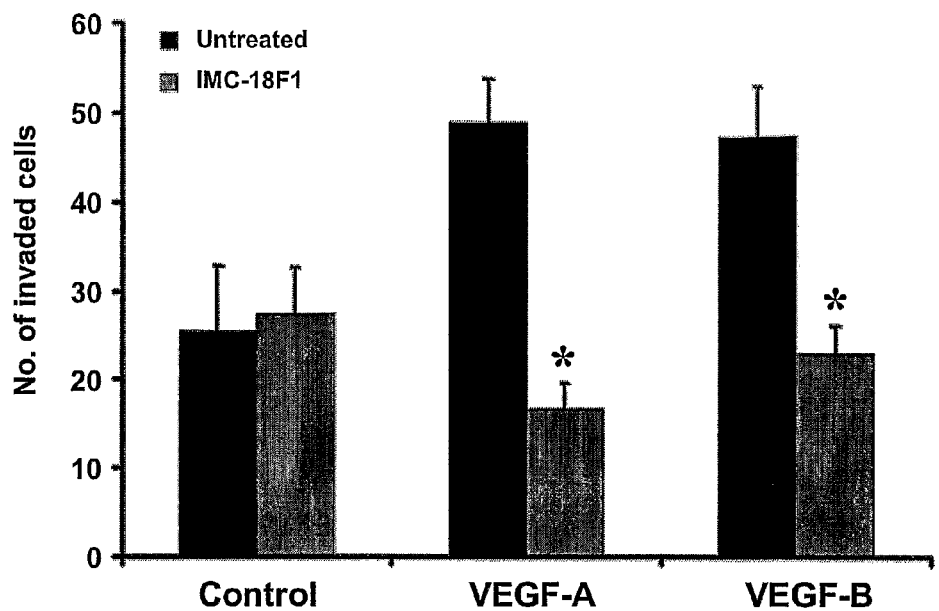
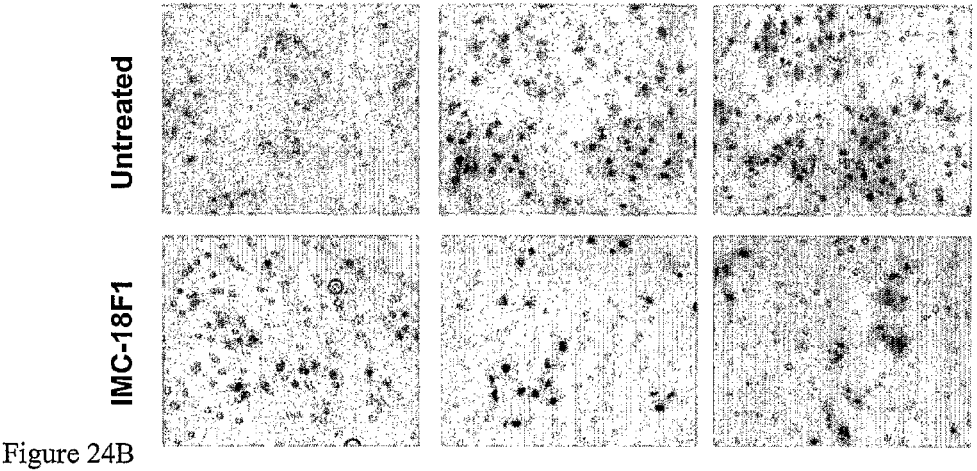
Figure 24B
Figure 24A and B: Inhibition of Tumor Cell Invasion. (A) SW480 tumor cells were treated with 18F1 in the presence of VEGF-A or VEGF-B for 48 hours. Cell migration across a layer of Matrigel is plotted as Mean ± SEM (*$P < 0.0001$). (B) Photomicrographs of migrated cells stained with Diff-Quik. Data from Pavco *et al*; Clin. Cancer Res. 2000; 6:2094-103.

Figure 25
Figure 25A
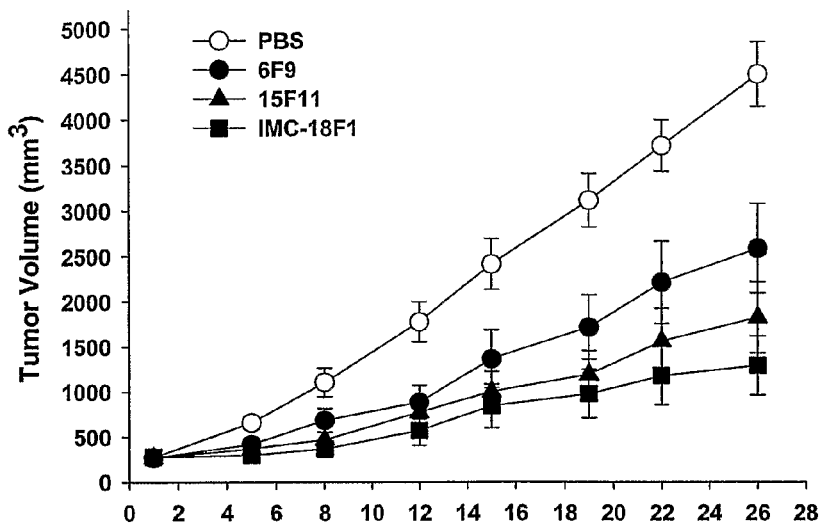
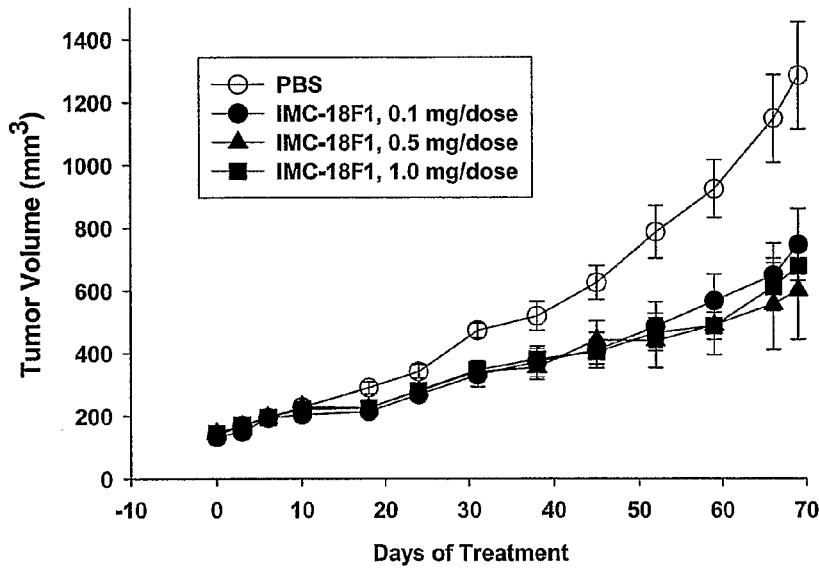
Figure 25B
Figure 25A and B: Effect of 18F1 Monotherapy on Breast Cancer Xenografts. (A) Mice with DU4475 xenografts were treated with 18F1, 6F9, or 15F11 antibodies to VEGFR-1, at 1.0 mg/dose, M-W-F. (B) Mice with MDA-MB-435 xenografts were treated with 18F1 at the indicated dosages or PBS at 0.5 mL/dose, M-W-F. Mean tumor volume ± SEM is plotted for n=12 per group.

Figure 26
Figure 26A
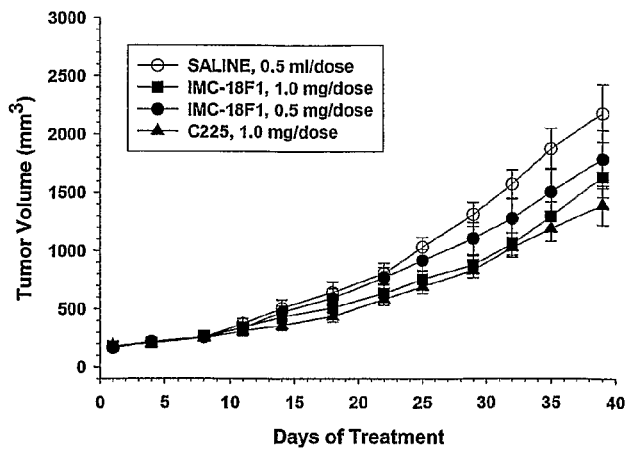
Figure 26B
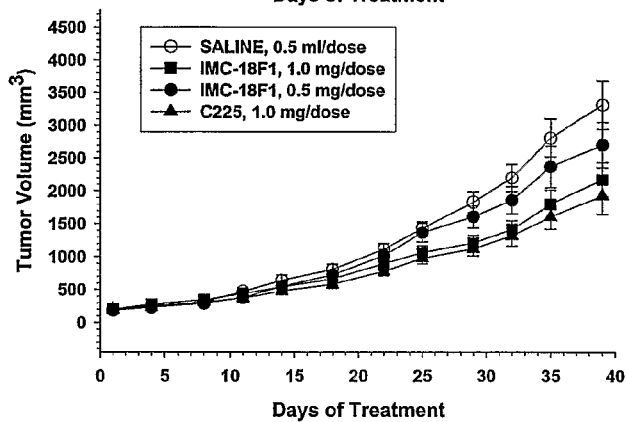
Figure 26C
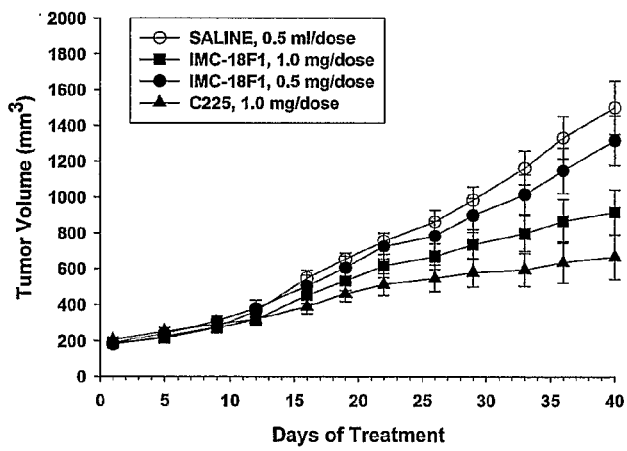
Figure 26A, B, and C: Effect of 18F1 Monotherapy on Colon Cancer Xenografts. Mice with HT-29 (A), DLD-1 (B), and GEO (C) xenografts were treated with 18F1 at the indicated dosages, M-W-F. Mean tumor volume ± SEM is plotted for n=10 per group.

Figure 27: Ki-67, phosphorylated MAPK (P-MAPK) and TUNEL (ApopTag) Staining in MDA-MB-231 Xenograft Tumors. Tumor sections were stained for Ki67, P-MAPK (14 days of 18F1 treatment at 20 mg/kg, 2x/week); or ApopTag (7 days of 18F1 treatment at 0.5 mg/dose, 3x/week) Representative tumor sections are shown. Control indicates the matching dose of Human IgG.

Figure 28
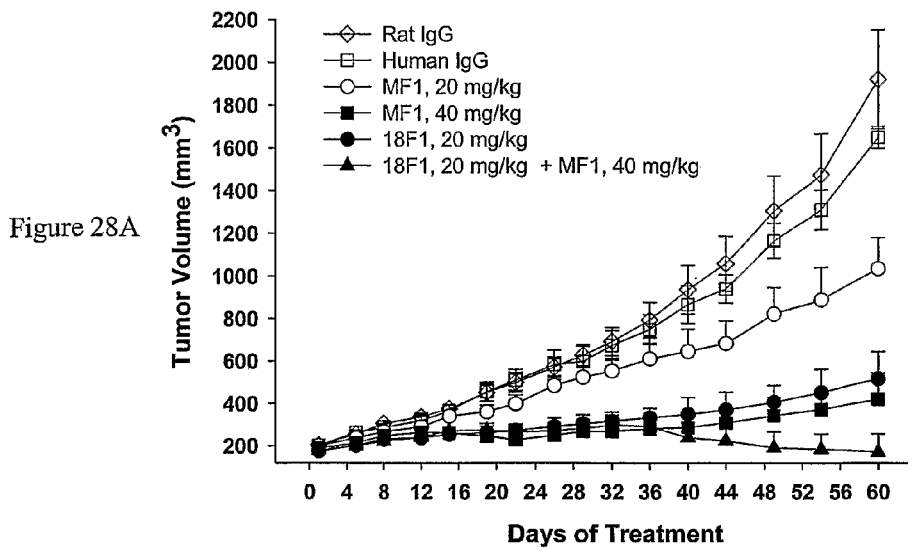
Figure 28A
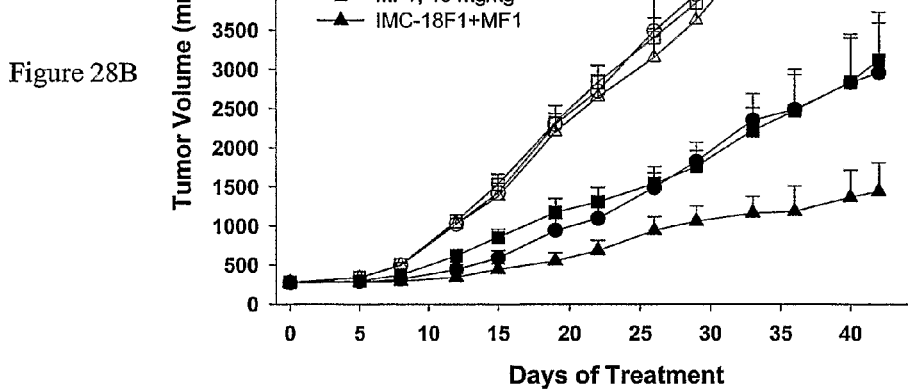
Figure 28B
Figure 28A and B: Effect of Combined Inhibition of Mouse and Human VEGFR-1 on Xenograft Growth. Mice with MDA-MB-231 (A) or DU4475 (B) xenografts were treated with 18F1, MF1 or the combination, at the indicated dosages (2x/week for 18F1 and 3x/week for MF1). Mean tumor volume ± SEM is plotted for n=16-18 per group.

Figure 29: Effect of Cyclophosphamide Treatment in Combination with Anti-mouse and human VEGFR-1 Antibodies on the Growth of MDA-MB-231 Xenografts. Mice with MDA-MB-231 xenografts were treated with 18F1 + MF1 alone (2x/week), cyclophosphamide monotherapy (q7d), or the combination, at the indicated dosages. Mean tumor volume ± SEM is plotted for n=12 per group.

Figure 30

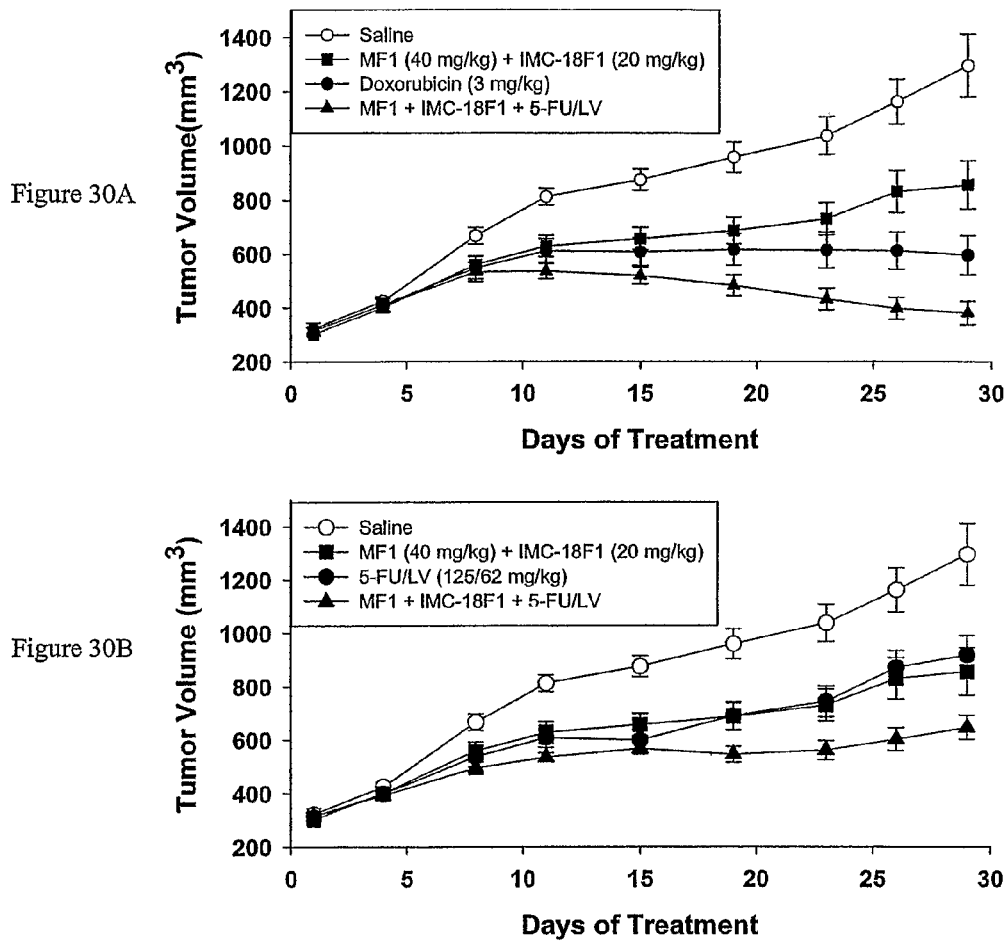

Figure 30A and B: Effect of 5-FU/LV or Doxorubicin Treatment in Combination with Anti-mouse and human VEGFR-1 Antibodies on the Growth of MDA-MB-231 Xenografts. Mice with MDA-MB-231 xenografts were treated with 18F1 + MF1 alone (3x/week), 5-FU/LV monotherapy (q7d) (A), doxorubicin (2x/week) (B) or a combination of antibody plus chemotherapy, at the indicated dosages. Mean tumor volume ± SEM is plotted for n=12 per group.

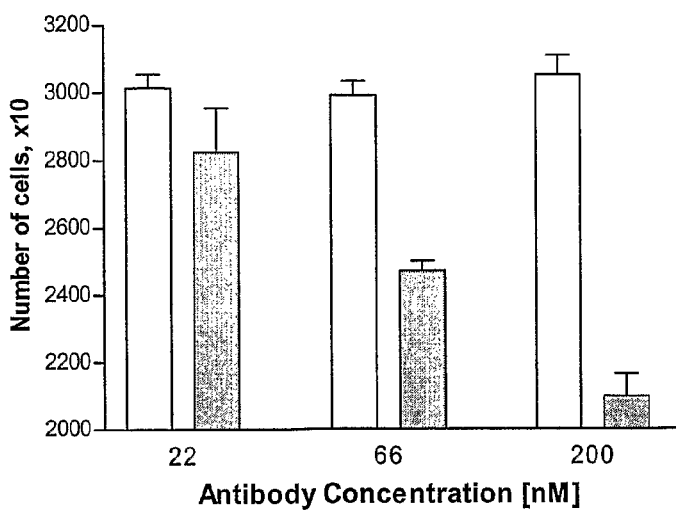

Figure 31B

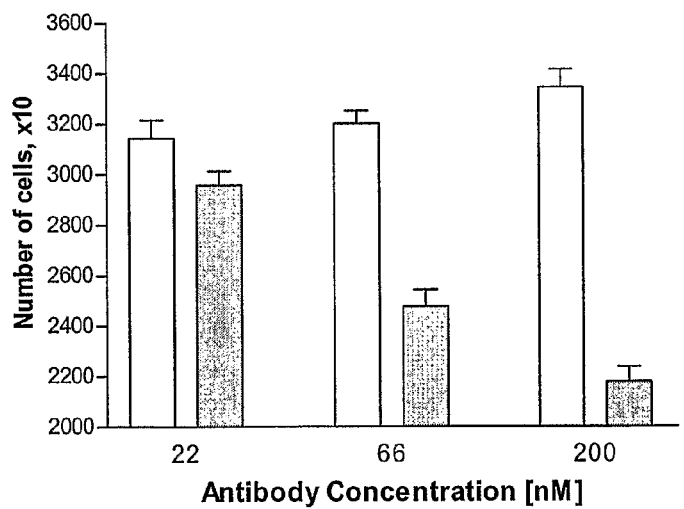

Figure 31A and B: Inhibition of Tumor Cell Proliferation. $2 \times 10^4$ DU4475 cells were serum starved overnight following treatment with desferrioxamine, then incubated with various amount of 18F1 (shadowed bar) or isotype control IgG (opened bar) in the presence of VEGF-A (A) or PlGF (B). After 2 days incubation, total cell number was determined using a Coulter cell counter. The results are shown as mean value with standard error.

Figure 32

Figure 32A
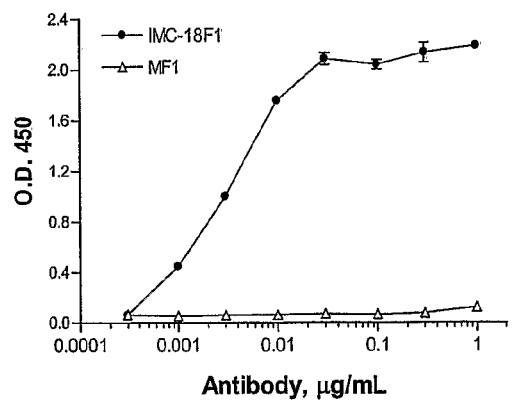

Figure 32B
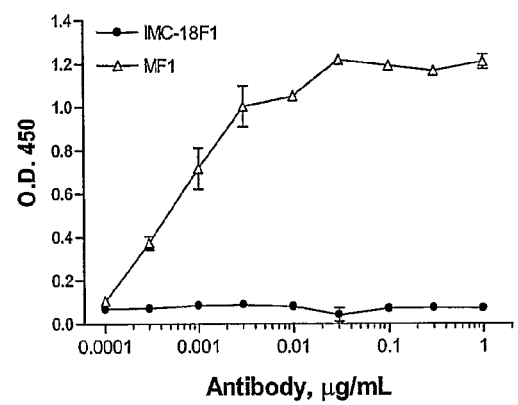

Figure 32C
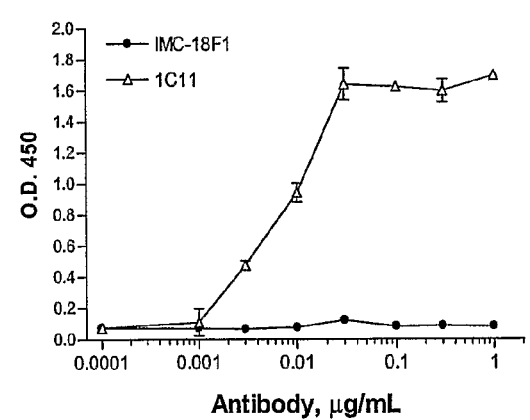

Figure 32A, B, and C: Specificity of 18F1 and Anti-mouse VEGFR-1 Antibody MF1. 18F1 has binding activity with immobilized recombinant human VEGFR-1 (A) but not with mouse VEGFR-1 (B) and human VEGFR-2 (C) as compared to positive control MF1 or VEGFR-2 specific antibody 1C11. Anti-mouse VEGFR-1 antibody MF1 did not bind to immobilized recombinant human VEGFR-1(A). 18F1 was used as a positive control in solid phase binding assay.

```
                         SEQUENCE LISTING

<160> NUMBER OF SEQ ID NOS: 56

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Gln Ser Gly Ser Ser Ser Tyr Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ala Ser Ser Arg Ala Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Tyr Gly Ser Ser Pro Leu Thr
1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Ser Val Ser Ser Ser Tyr Leu Ala
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

```
Gly Phe Thr Phe Ser Ser Tyr Gly Met His
1               5                   10
```

```
<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Ile Trp Tyr Asp Gly Ser Asn Lys Tyr Tyr Ala Asp Ser Val Lys
1               5                   10                  15

Gly
```

```
<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp His Phe Gly Ser Gly Ala His Tyr Tyr Tyr Tyr Tyr Gly Met Asp
1               5                   10                  15

Val
```

```
<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp His Tyr Gly Ser Gly Ala His Tyr Tyr Tyr Tyr Tyr Gly Met Asp
1               5                   10                  15

Val
```

```
<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Ile Trp Phe Asp Gly Ser Asn Lys Tyr Tyr Ala Asp Ser Val Lys
1               5                   10                  15

Gly
```

```
<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp His Tyr Gly Ser Gly Ala His Ser Tyr Tyr Tyr Tyr Gly Leu Asp
1               5                   10                  15
```

Val

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Ala Phe Ser Ser Tyr Gly Met His
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Ile Trp Tyr Asp Gly Ser Asn Lys Tyr Tyr Ala Asp Ser Val Arg
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp His Tyr Gly Ser Gly Val His His Tyr Phe Tyr Tyr Gly Leu Asp
1               5                   10                  15

Val

<210> SEQ ID NO 14
<211> LENGTH: 120
<212> TYPE: PRT
<213> ORGANISM: Homo sapiens

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Gly Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro
            115                 120

<210> SEQ ID NO 15
<211> LENGTH: 120
<212> TYPE: PRT
<213> ORGANISM: Homo sapiens

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Arg Leu Glu Ile Lys Arg Thr Val Ala
            100                 105                 110

Ala Pro Ser Val Phe Ile Phe Pro
            115                 120

<210> SEQ ID NO 16
<211> LENGTH: 120
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro
            115                 120

<210> SEQ ID NO 17
<211> LENGTH: 126
<212> TYPE: PRT
<213> ORGANISM: Homo sapiens

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val

```
                    35                  40                  45
Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr His Cys
                 85                  90                  95

Thr Arg Asp His Phe Gly Ser Gly Ala His Tyr Tyr Tyr Tyr Tyr Gly
                100                 105                 110

Met Asp Val Trp Gly Gln Gly Thr Thr Val Thr Val Ser Ser
            115                 120                 125
```

<210> SEQ ID NO 18
<211> LENGTH: 126
<212> TYPE: PRT
<213> ORGANISM: Homo sapiens

<400> SEQUENCE: 18

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp His Tyr Gly Ser Gly Ala His Tyr Tyr Tyr Tyr Tyr Gly
                100                 105                 110

Met Asp Val Trp Gly Gln Gly Thr Thr Val Thr Val Ser Ser
            115                 120                 125
```

<210> SEQ ID NO 19
<211> LENGTH: 126
<212> TYPE: PRT
<213> ORGANISM: Homo sapiens

<400> SEQUENCE: 19

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Phe Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp His Tyr Gly Ser Gly Ala His Tyr Tyr Tyr Tyr Tyr Gly
                100                 105                 110

Leu Asp Val Trp Gly Gln Gly Thr Ser Val Thr Val Ser Ser
            115                 120                 125
```

<210> SEQ ID NO 20
<211> LENGTH: 126
<212> TYPE: PRT
<213> ORGANISM: Homo sapiens

<400> SEQUENCE: 20

Gln Ala Gln Val Val Glu Ser Gly Gly Gly Val Val Gln Ser Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Arg Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Tyr Gly Ser Gly Val His His Tyr Phe Tyr Tyr Gly
            100                 105                 110

Leu Asp Val Trp Gly Gln Gly Thr Thr Val Thr Val Ser Ser
        115                 120                 125

<210> SEQ ID NO 21
<211> LENGTH: 360
<212> TYPE: DNA
<213> ORGANISM: Homo sapiens

<400> SEQUENCE: 21
gaaattgtgt tgacgcagtc tccaggcacc ctgtccttgt ctccagggga aagagccacc      60
ctctcctgca gggccagtca gagtggtagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgct cactttcggc     300
ggagggacca aggtggagat caaacgaact gtggctgcac catctgtctt catcttcccg     360

<210> SEQ ID NO 22
<211> LENGTH: 360
<212> TYPE: DNA
<213> ORGANISM: Homo sapiens

<400> SEQUENCE: 22
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctct caccttcggc     300
caagggacac gactggagat taaacgaact gtggctgcac catctgtctt catcttcccg     360

<210> SEQ ID NO 23
<211> LENGTH: 360
<212> TYPE: DNA
<213> ORGANISM: Homo sapiens

<400> SEQUENCE: 23

```
gaaattgtgt tgacgcagtc tccaggcacc ctgtctttgt ctccaggga aagagccacc    60 ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccgct cactttcggc  300
ggagggacca aggtggagat caaacgaact gtggctgcac catctgtctt catctttccg  360
```

<210> SEQ ID NO 24
<211> LENGTH: 378
<212> TYPE: DNA
<213> ORGANISM: Homo sapiens

<400> SEQUENCE: 24

```
caggtgcagc tggtggagtc tgggggaggc gtggtccagc ctgggaggtc cctgagactc    60
tcctgtgcag cgtctggatt caccttcagt agttatggca tgcactgggt ccgccaggct  120
ccaggcaagg ggctggagtg ggtggcagtt atatggtatg atggaagtaa taaatactat  180
gcagactccg tgaagggccg attcaccatc tccagagaca attccaagaa cacggtgtat  240
ctgcaaatga acagcctgag agccgaggac acggctgtgt atcactgtac gagagatcac  300
tttggttcgg gggctcacta ctactactac tacggtatgg acgtctgggg ccaagggacc  360
acggtcaccg tctcctca                                                378
```

<210> SEQ ID NO 25
<211> LENGTH: 378
<212> TYPE: DNA
<213> ORGANISM: Homo sapiens

<400> SEQUENCE: 25

```
caggtgcagc tggtggagtc tgggggaggc gtggtccagc ctgggaggtc cctgagactc    60
tcctgtgcag cgtctggatt caccttcagt agctatggca tgcactgggt ccgccaggct  120
ccaggcaagg ggctggagtg ggtggcagtt atatggtatg atggaagtaa taaatactat  180
gcagactccg tgaagggccg attcaccatc tccagagaca attccaagaa cacgctgtat  240
ctgcaaatga acagcctgag agccgaggac acggctgtgt attactgtgc gagagatcac  300
tatggttcgg gggctcacta ctactactac tacggtatgg acgtctgggg ccaagggacc  360
acggtcaccg tctcctca                                                378
```

<210> SEQ ID NO 26
<211> LENGTH: 378
<212> TYPE: DNA
<213> ORGANISM: Homo sapiens

<400> SEQUENCE: 26

```
caggtgcagc tggtggagtc tgggggaggc gtggtccagc ctgggaggtc cctgagactc    60
tcctgtgcag cgtctggatt caccttcagt agctatggca tgcactgggt ccgccaggct  120
ccaggcaagg ggctggagtg ggtggcagtt atatggtttg atggaagtaa taaatactat  180
gcagactccg tgaagggccg attcaccatc tccagagaca attccaagaa cacgctgtat  240
ctgcaaatga acagcctgag agccgaggac acggctgtgt attactgtgc gagagatcac  300
tatggttcgg gggctcactc ctactactac tacggtttgg acgtttgggg ccaagggacc  360
tcggtcaccg tctcctca                                                378
```

-continued

```
<210> SEQ ID NO 27
<211> LENGTH: 378
<212> TYPE: DNA
<213> ORGANISM: Homo sapiens

<400> SEQUENCE: 27
caggcgcagg tggtggagtc tgggggaggc gtggtccagt ctgggaggtc cctgagactc      60
tcctgtgcag cgtctggatt cgccttcagt agctacggca tgcactgggt ccgccaggct     120
ccaggcaagg ggctggagtg ggtggcagtt atatggtatg atggaagtaa taaatactat     180
gcagactccg tgaggggccg attcaccatc tccagagaca attccgagaa cacgctgtat     240
ctgcaaatga acagcctgag agccgaggac accgctgtgt attactgtgc cagagatcac     300
tatggttcgg gggtgcacca ctatttctac tacggtctgg acgtctgggg ccaagggacc     360
acggtcaccg tctcctca                                                   378

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atggagtttg ggctgagctg                                                  20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgccaggggg aagaccgatg g                                                21

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atggaaaccc cagcgcagct tctc                                             24

<210> SEQ ID NO 32
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 32
cgggaagatg aagacagatg                                                     20

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Val or Gly

<400> SEQUENCE: 33

Arg Ala Ser Gln Ser Xaa Ser Ser Ser Tyr Leu Ala
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Thr or Ala

<400> SEQUENCE: 34

Gly Phe Xaa Phe Ser Ser Tyr Gly Met His
1               5                   10

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr or Phe
<220> FEATURE:
<221> NAME/KEY: MOD_RES
<222> LOCATION: (16)..(16)
<223> OTHER INFORMATION: Lys or Arg

<400> SEQUENCE: 35

Val Ile Trp Xaa Asp Gly Ser Asn Lys Tyr Tyr Ala Asp Ser Val Xaa
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phe or Tyr
<220> FEATURE:
```

```
<221> NAME/KEY: MOD_RES
<222> LOCATION: (7)..(7)
<223> OTHER INFORMATION: Ala or Val
<220> FEATURE:
<221> NAME/KEY: MOD_RES
<222> LOCATION: (9)..(9)
<223> OTHER INFORMATION: Tyr, Ser, or His
<220> FEATURE:
<221> NAME/KEY: MOD_RES
<222> LOCATION: (11)..(11)
<223> OTHER INFORMATION: Tyr or Phe
<220> FEATURE:
<221> NAME/KEY: MOD_RES
<222> LOCATION: (15)..(15)
<223> OTHER INFORMATION: Met or Leu

<400> SEQUENCE: 36

Asp His Xaa Gly Ser Gly Xaa His Xaa Tyr Xaa Tyr Tyr Gly Xaa Asp
1               5                   10                  15

Val

<210> SEQ ID NO 37
<211> LENGTH: 140
<212> TYPE: PRT
<213> ORGANISM: Homo sapiens

<400> SEQUENCE: 37

Met Glu Thr Pro Ala Gln Leu Leu Phe Leu Leu Leu Leu Trp Leu Pro
1               5                   10                  15

Glu Ser Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Gly Ser Ser Ser Tyr Leu Ala Trp Tyr Gln Gln Lys Pro Gly Gln Ala
50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Pro Leu Thr Phe Gly Gly Gly Thr Lys Val Glu Ile Lys
        115                 120                 125

Arg Thr Val Ala Ala Pro Ser Val Phe Ile Phe Pro
    130                 135                 140

<210> SEQ ID NO 38
<211> LENGTH: 145
<212> TYPE: PRT
<213> ORGANISM: Homo sapiens

<400> SEQUENCE: 38

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
50                  55                  60

Glu Trp Val Ala Val Ile Trp Tyr Asp Gly Ser Asn Lys Tyr Tyr Ala
65                  70                  75                  80
```

```
Asp Ser Val Lys Gly Arg Phe Thr Ile Ser Arg Asp Asn Ser Lys Asn
                85                  90                  95

Thr Val Tyr Leu Gln Met Asn Ser Leu Arg Ala Glu Asp Thr Ala Val
            100                 105                 110

Tyr His Cys Thr Arg Asp His Phe Gly Ser Gly Ala His Tyr Tyr Tyr
        115                 120                 125

Tyr Tyr Gly Met Asp Val Trp Gly Gln Gly Thr Thr Val Thr Val Ser
    130                 135                 140

Ser
145

<210> SEQ ID NO 39
<211> LENGTH: 140
<212> TYPE: PRT
<213> ORGANISM: Homo sapiens

<400> SEQUENCE: 39

Met Glu Thr Pro Ala Gln Leu Leu Phe Leu Leu Leu Leu Trp Leu Pro
1               5                   10                  15

Glu Ser Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Gly Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Leu Thr Phe Gly Gly Gly Thr Lys Val Glu Ile Lys
        115                 120                 125

Arg Thr Val Ala Ala Pro Ser Val Phe Ile Phe Pro
    130                 135                 140

<210> SEQ ID NO 40
<211> LENGTH: 145
<212> TYPE: PRT
<213> ORGANISM: Homo sapiens

<400> SEQUENCE: 40

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110
```

Tyr Tyr Cys Ala Arg Asp His Tyr Gly Ser Gly Ala His Tyr Tyr Tyr
            115                 120                 125

Tyr Tyr Gly Met Asp Val Trp Gly Gln Gly Thr Thr Val Thr Val Ser
130                 135                 140

Ser
145

<210> SEQ ID NO 41
<211> LENGTH: 140
<212> TYPE: PRT
<213> ORGANISM: Homo sapiens

<400> SEQUENCE: 41

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Leu Thr Phe Gly Gln Gly Thr Arg Leu Glu Ile Lys
        115                 120                 125

Arg Thr Val Ala Ala Pro Ser Val Phe Ile Phe Pro
    130                 135                 140

<210> SEQ ID NO 42
<211> LENGTH: 145
<212> TYPE: PRT
<213> ORGANISM: Homo sapiens

<400> SEQUENCE: 42

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Phe Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp His Tyr Gly Ser Gly Ala His Ser Tyr Tyr
        115                 120                 125

Tyr Tyr Gly Leu Asp Val Trp Gly Gln Gly Thr Ser Val Thr Val Ser
    130                 135                 140

Ser

<210> SEQ ID NO 43
<211> LENGTH: 140
<212> TYPE: PRT
<213> ORGANISM: Homo sapiens

<400> SEQUENCE: 43

```
Met Glu Thr Pro Ala Gln Leu Phe Leu Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Leu Thr Phe Gly Gly Gly Thr Lys Val Glu Ile Lys
        115                 120                 125

Arg Thr Val Ala Ala Pro Ser Val Phe Ile Phe Pro
    130                 135                 140
```

<210> SEQ ID NO 44
<211> LENGTH: 145
<212> TYPE: PRT
<213> ORGANISM: Homo sapiens

<400> SEQUENCE: 44

```
Met Glu Phe Gly Leu Ser Trp Val Phe Leu Val Ala Leu Leu Arg Gly
1               5                   10                  15

Val Gln Cys Gln Ala Gln Val Val Glu Ser Gly Gly Gly Val Val Gln
                20                  25                  30

Ser Gly Arg Ser Leu Arg Leu Ser Cys Ala Ala Ser Gly Phe Ala Phe
            35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Arg Gly Arg Phe Thr Ile Ser Arg Asp Asn Ser Glu Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp His Tyr Gly Ser Gly Val His His Tyr Phe
        115                 120                 125

Tyr Tyr Gly Leu Asp Val Trp Gly Gln Gly Thr Thr Val Thr Val Ser
    130                 135                 140

Ser
145
```

<210> SEQ ID NO 45
<211> LENGTH: 420
<212> TYPE: DNA
<213> ORGANISM: Homo sapiens

<400> SEQUENCE: 45

```
atggaaaccc cagcgcagct tctcttcctc ctgctactct ggctcccaga aagcaccgga      60
gaaattgtgt tgacgcagtc tccaggcacc ctgtccttgt ctccagggga aagagccacc     120
ctctcctgca gggccagtca gagtggtagc agcagctact tagcctggta ccagcagaaa     180
cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgta ttactgtcag cagtatggta gctcaccgct cactttcggc     360
ggagggacca aggtggagat caaacgaact gtggctgcac catctgtctt catcttcccg     420
```

<210> SEQ ID NO 46
<211> LENGTH: 435
<212> TYPE: DNA
<213> ORGANISM: Homo sapiens

<400> SEQUENCE: 46

```
atggagtttg ggctgagctg ggttttcctc gttgctcttt taagaggtgt ccagtgtcag      60
gtgcagctgg tggagtctgg gggaggcgtg gtccagcctg gaggtccct gagactctcc     120
tgtgcagcgt ctggattcac cttcagtagt tatggcatgc actgggtccg ccaggctcca     180
ggcaagggc tggagtgggt ggcagttata tggtatgatg gaagtaataa atactatgca     240
gactccgtga agggccgatt caccatctcc agagacaatt ccaagaacac ggtgtatctg     300
caaatgaaca gcctgagagc cgaggacacg gctgtgtatc actgtacgag agatcacttt     360
ggttcggggg ctcactacta ctactactac ggtatggacg tctggggcca agggaccacg     420
gtcaccgtct cctca                                                       435
```

<210> SEQ ID NO 47
<211> LENGTH: 420
<212> TYPE: DNA
<213> ORGANISM: Homo sapiens

<400> SEQUENCE: 47

```
atggaaaccc cagcgcagct tctcttcctc ctgctactct ggctcccaga aagcaccgga      60
gaaattgtgt tgacgcagtc tccaggcacc ctgtccttgt ctccagggga aagagccacc     120
ctctcctgca gggccagtca gagtggtagc agcagctact tagcctggta ccagcagaaa     180
cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgta ttactgtcag cagtatggta gctcaccgct cactttcggc     360
ggagggacca aggtggagat caaacgaact gtggctgcac catctgtctt catcttcccg     420
```

<210> SEQ ID NO 48
<211> LENGTH: 435
<212> TYPE: DNA
<213> ORGANISM: Homo sapiens

<400> SEQUENCE: 48

```
atggagtttg ggctgagctg ggttttcctc gttgctcttt taagaggtgt ccagtgtcag      60
gtgcagctgg tggagtctgg gggaggcgtg gtccagcctg gaggtccct gagactctcc     120
tgtgcagcgt ctggattcac cttcagtagc tatggcatgc actgggtccg ccaggctcca     180
ggcaagggc tggagtgggt ggcagttata tggtatgatg gaagtaataa atactatgca     240
gactccgtga agggccgatt caccatctcc agagacaatt ccaagaacac ggtgtatctg     300
```

```
caaatgaaca gcctgagagc cgaggacacg gctgtgtatt actgtgcgag agatcactat    360
ggttcggggg ctcactacta ctactactac ggtatggacg tctggggcca agggaccacg    420
gtcaccgtct cctca                                                     435
```

<210> SEQ ID NO 49
<211> LENGTH: 420
<212> TYPE: DNA
<213> ORGANISM: Homo sapiens

<400> SEQUENCE: 49

```
atggaagccc cagcgcagct tctcttcctc ctgctactct ggctcccaga taccaccgga     60
gaaattgtgt tgacgcagtc tccaggcacc ctgtctttgt ctccagggga aagagccacc    120
ctctcctgca gggccagtca gagtgttagc agcagctact tagcctggta ccagcagaaa    180
cctggccagg ctcccaggct cctcatctat ggtgcatcca gcagggccac tggcatccca    240
gacaggttca gtggcagtgg gtctgggaca gacttcactc tcaccatcag cagactggag    300
cctgaagatt ttgcagtgta ttactgtcag cagtatggta gctcacctct caccttcggc    360
caagggacac gactggagat taaacgaact gtggctgcac catctgtctt catcttcccg    420
```

<210> SEQ ID NO 50
<211> LENGTH: 435
<212> TYPE: DNA
<213> ORGANISM: Homo sapiens

<400> SEQUENCE: 50

```
atggagtttg ggctgagctg gttttcctc gttgctcttt taagaggtgt ccagtgtcag     60
gtgcagctgg tggagtctgg gggaggcgtg gtccagcctg gaggtccct gagactctcc    120 tgtgcagcgt ctggattcac cttcagtagc tatggcatgc actgggtccg ccaggctcca    180
ggcaaggggc tggagtgggt ggcagttata tggtttgatg gaagtaataa atactatgca    240
gactccgtga agggccgatt caccatctcc agagacaatt ccaagaacac gctgtatctg    300
caaatgaaca gcctgagagc cgaggacacg gctgtgtatt actgtgcgag agatcactat    360
ggttcggggg ctcactccta ctactactac ggtttggacg tttggggcca agggacctcg    420
gtcaccgtct cctca                                                     435
```

<210> SEQ ID NO 51
<211> LENGTH: 420
<212> TYPE: DNA
<213> ORGANISM: Homo sapiens

<400> SEQUENCE: 51

```
atggaaaccc cagcgcagct tctcttcctc ctgctactct ggctcccaga taccaccgga     60
gaaattgtgt tgacgcagtc tccaggcacc ctgtctttgt ctccagggga aagagccacc    120
ctctcctgca gggccagtca gagtgttagc agcagctact tagcctggta ccagcagaaa    180
cctggccagg ctcccaggct cctcatctat ggtgcatcca gcagggccac tggcatccca    240
gacaggttca gtggcagtgg gtctgggaca gacttcactc tcaccatcag cagactggag    300
cctgaagatt ttgcagtgta ttactgtcag cagtatggta gctcaccgct cactttcggc    360
ggagggacca aggtggagat caaacgaact gtggctgcac catctgtctt catctttccg    420
```

<210> SEQ ID NO 52
<211> LENGTH: 435
<212> TYPE: DNA
<213> ORGANISM: Homo sapiens

```
<400> SEQUENCE: 52
atggagtttg ggctgagctg ggttttcctc gttgctcttt taagaggtgt ccagtgtcag      60
gcgcaggtgg tggagtctgg gggaggcgtg gtccagtctg ggaggtccct gagactctcc     120
tgtgcagcgt ctggattcgc cttcagtagc tacggcatgc actgggtccg ccaggctcca     180
ggcaaggggc tggagtgggt ggcagttata tggtatgatg gaagtaataa atactatgca     240
gactccgtga ggggccgatt caccatctcc agagacaatt ccgagaacac gctgtatctg     300
caaatgaaca gcctgagagc cgaggacacc gctgtatatt actgtgccag agatcactat     360
ggttcggggg tgcaccacta tttctactac ggtctggacg tctggggcca agggaccacg     420
gtcaccgtct cctca                                                     435

<210> SEQ ID NO 53
<211> LENGTH: 20
<212> TYPE: DNA
<213> ORGANISM: Homo sapiens

<400> SEQUENCE: 53
atggagtttg ggctgagctg                                                  20

<210> SEQ ID NO 54
<211> LENGTH: 21
<212> TYPE: DNA
<213> ORGANISM: Homo sapiens

<400> SEQUENCE: 54 tgccagggg aagaccgatg g                                                 21

<210> SEQ ID NO 55
<211> LENGTH: 24
<212> TYPE: DNA
<213> ORGANISM: Homo sapiens

<400> SEQUENCE: 55
atggaaaccc cagcgcagct tctc                                             24

<210> SEQ ID NO 56
<211> LENGTH: 20
<212> TYPE: DNA
<213> ORGANISM: Homo sapiens

<400> SEQUENCE: 56
cgggaagatg aagacagatg                                                  20
```

ANTIBODIES AGAINST VASCULAR ENDOTHELIAL GROWTH FACTOR RECEPTOR-1

FIELD OF INVENTION

The present invention relates to antibodies that are specific for vascular endothelial growth factor receptor-1 (VEGFR-I) and methods of treating angiogenesis-associated diseases and tumors with antibodies to VEGFR-I.

BACKGROUND OF THE INVENTION

Angiogenesis, which refers to the formation of capillaries from pre-existing vessels in the embryo and adult organism, is known to be a key element in tumor growth, survival and metastasis. Growth factors and their receptors, including epidermal growth factor (EGF), transforming growth factor-α (TGF-α), transforming growth factor-δ (TGF-/3), acidic and basic fibroblast growth factor (aFGF and bFGF), platelet derived growth factor (PDGF), and vascular endothelial growth factor (VEGF), are thought to play a role in tumor angiogenesis. See Klagsbrun & D'Amore, Annual Rev. Physiol., 53: 217-239 (1991). Binding of these growth factors to their cell surface receptors induces receptor activation, which initiates and modifies signal transduction pathways and leads to cell proliferation and differentiation. VEGF, an endothelial cell-specific mitogen, is distinct among these factors in that it acts as an angiogenesis inducer by specifically promoting the proliferation of endothelial cells.

The biological response of VEGF is mediated through its high affinity receptors, which are selectively expressed on endothelial cells during embryogenesis (Millauer, *Cell*, 72: 835-846 (1993)) and during tumor formation. VEGF receptors (VEGFRs) typically are class III receptor-type tyrosine kinases characterized by having several, typically 5 or 7, immunoglobulin-like loops in their amino-terminal extracellular receptor ligand-binding domains (Kaipainen et ah, *J. Exp. Med.*, 178:2077-2088 (1993)). The other two regions include a transmembrane region and a carboxy-terminal intracellular catalytic domain interrupted by an insertion of hydrophilic interlbdnase sequences of variable lengths, called the kinase insert domain (Terman et al., *Oncogene*, 6:1677-1683 (1991)). VEGFRs mclude>z,s-like tyrosine kinase receptor (flt-1), or VEGFR-I, sequenced by Shibuya et al., *Oncogene*, 5: 519-524 (1990), kinase insert domain-containing receptor/fetal liver kinase (KDR/fik-1), or VEGFR-2, described in WO 92/14248, filed Feb. 20, 1992, and Terman et al, *Oncogene*, 6: 1677-1683 (1991) and sequenced by Matthews et al, *Proc. Natl. Acad. Sd. USA*, 88: 9026-9030 (1991), although other receptors, such as neuropilin-1 and -2, can also bind VEGF. Another tyrosine kinase receptor, VEGFR-3 (flt-4), binds the VEGF homologues VEGF-C and VEGF-D and is more important in the development of lymphatic vessels.

The importance of VEGFR-I in regulation of pathological angiogenesis has been shown in in vivo experimental models. Deficiency of VEGFR-I tyrosine kinase domain results in decreased blood vessel formation in tumors, indicating a significant role of VEGFR-I tyrosine kinase in pathological angiogenesis (Hiratsuka et al., *Cancer Research*, 61:1207-1213 (2001)). VEGFR-I tyrosine kinase domain is also required for promotion of tumor pathogenesis and metastasis by induction of matrix metalloprotease-9 (MMP-9) in endothelial cells and macrophages (Hiratsuka et al., *Cancer Cell*, 2:289-300 (2002)). In addition, VEGFR-I has been shown to mediate mobilization and differentiation of P1GF responsive BM-derived precursors (Hattori et al, *Nature Medicine*, 8:841-849 (2002)). Inhibition of VEGFR-I by an anti-VEGFR-I antibody led to reduction of tumor angiogenesis by preventing recruitment of bone marrow-derived endothelial and monocyte progenitor cells from vascularization in tumors (Lyden et al., *Nature Medicine*, 7:1194-1201 (2001)). Treatment with an anti-VEGFR-I antibody also effectively inhibited pathological angiogenesis in tumors and ischemic retina in animal models (Luttun et al., *Nature Medicine*, 8:831-840 (2002)).

hi addition to the role of VEGFR-I in angiogenesis, co-expression of VEGF and its receptors is also frequently found in hematological malignant cells and certain solid tumor cells (Bellamy, *Cancer Research*, 59:728-733 (1999); Ferrer et al., *Urology*, 54:567-572 (1999); Price et al, *Cell Growth Differ.*, 12:129-135 (2001)). VEGF has been shown to directly induce proliferation, survival, and invasion of VEGF receptor expressing leukemia cells by activation of downstream intracellular signaling pathways through a ligand stimulated autocrine loop (Dias et al, *Proc Natl Acad Sd USA*, 98:10857-10862 (2001); Gerber et al, *J Mol Med*, 81:20-31 (2003)). VEGF stimulation also results in an increased invasiveness of the VEGFR-I expressing breast cancer cells by inducing the activation of ERK1/2 and PI 3/Akt-kinase signaling pathways (Price et al, *Cell Growth Differ.*, 12:129-135 (2001)).

VEGFR-I and its ligands have also been shown to play and important role in inflammatory disorders. VEGF-B deficiency resulted in the reduction of inflammation-associated vessel density and synovial inflammation in models of arthritis (Mould et al, *Arthritis Rheum.*, 48:2660-2669 (2003)). P1GF also plays a critical tole in the control of cutaneous inflammation by mediating vascular enlargement, inflammatory cells and monocytes/macrophages, and has been shown to contribute to modulation of atherosclerosis and rheumatoid arthritis in animal models (Luttun et al, *Nature Medicine*, 8:831-840 (2002); Autiero & *Thromb Haemost*, 1:1356-1370 (2003)). Treatment with a neutralizing anti-VEGFR-1 antibody suppressed inflammatory joint destruction in arthritis, reduced atherosclerotic plaque growth and vulnerability. The anti-inflammatory effects of the anti-VEGFR-1 antibody were attributable to a reduced mobilization of bone marrow-derived myeloid progenitors into the peripheral blood, a defective activation of myeloid cells, and an impaired differentiation and infiltration of VEGFR-I-expressing leukocytes in inflamed tissues. Thus, VEGFR-I may also be therapeutic target for treatment of inflammation-related disorders.

There remains a need for agents which inhibit VEGF receptor activity, such as fully human monoclonal antibodies (mAbs) specific for VEGFR-I. The anti-VEGFR-1 antibodies may be a useful, novel therapeutic antagonist for treatment of angiogenesis-associated diseases and cancer.

BRIEF SUMMARY OF THE INVENTION

In an embodiment, the present invention provides a monoclonal antibody or fragment thereof that specifically bind to VEGFR-I and comprises a light chain complementarity determining region-2 (CDR2) of SEQ ID NO: 2 and a light chain complementarity region-3 (CDR3) of SEQ ID NO: 3.

In another embodiment, the present invention provides a monoclonal antibody or fragment thereof that specifically binds to VEGFR-I and is at least 70% homologous to the amino acid sequence of an antibody or fragment thereof that comprises a light chain complementarity determining region-2 (CDR2) of SEQ ID NO: 2 and a light chain complementarity region-3 (CDR3) of SEQ ID NO: 3.

In another embodiment, the present invention provides an isolated polynucleotide comprising a nucleotide sequence selected from the group consisting of SEQ ID NO: 21, SEQ ID NO: 22, SEQ ID NO: 23, SEQ ID NO: 24, SEQ ID NO: 25, SEQ ID NO: 26, and SEQ ID NO: 27. The nucleotide sequence encodes an antibody or fragment thereof that specifically binds to VEGFR-I.

In another embodiment, the present invention provides an isolated polynucleotide comprising a nucleotide sequence that encodes an antibody or fragment thereof that specifically binds to VEGFR-I and that is at least 70% homologous to the nucleotide sequence selected from the group consisting of SEQ ID NO: 21, SEQ ID NO: 22, SEQ ID NO: 23, SEQ ID NO: 24, SEQ ID NO: 25, SEQ ID NO: 26, and SEQ ID NO: 27.

In another embodiment, the present invention provides a method of inhibiting angiogenesis or reducing tumor growth by administering a therapeutically effective amount of an antibody or fragment thereof that specifically bind to VEGFR-I and comprises a light chain complementarity determining region-2 (CDR2) of SEQ ID NO: 2 and a light chain complementarity region-3 (CDR3) of SEQ ID NO: 3.

BRIEF DESCRIPTION OF THE FIGURES

FIG. 1 is the amino acid sequences of the light chain variable region and the heavy chain variable region of embodiments of anti-VEGFR-I antibodies of the present invention.

FIG. 2 is the nucleotide sequences of the light chain variable region and the heavy chain variable region of embodiments of anti-VEGFR-I antibodies of the present invention.

FIG. 6A-D are charts depicting the results of specificity of anti-VEGFR-I antibody 18F1 of the present invention with binding of human VEGFR-I (FIG. 6A), but not mouse VEGFR-I (FIG. 6B), human VEGFR-2 (FIG. 6C), or mouse VEGFR-2 (FIG. 6D).

FIG. 8A-B is results of flow cytometry analysis showing binding reactivity of anti-VEGFR-1 antibody 18F1 of the present invention with VEGFR-I expressing porcine endothelial cells (FIG. 8A) and DU4475 human breast carcinoma cells (FIG. 8B).

FIGS. 14A-B is a Western blot analysis demonstrating the inhibition of PIGF (FIG. 14A) or VEGF (FIG. 14B)-*induced* activation of ERK 1/2 downstream signaling by anti-VEGFR-I antibody 18F1 of the present invention in VEGFR-I expressing porcine aorta endothelial cells.

FIG. 18A-B is a dose response curve showing the inhibition of PIGF (FIG. 18A) or VEGF (FIG. 18B)-*stimulated* cell proliferation in DU4475 breast carcinoma cells treated with anti-VEGFR-I antibody 18F1 of the present invention in a dose response manner.

FIG. 20A-C is a chart plotting tumor growth of DU4475 (FIG. 20A), MDA-MB-231 (FIG. 20B) and MDA-MB-435 (FIG. 20C) breast tumors versus days after treatment with anti-VEGFR-I antibody 18F1 of the present invention.

FIG. 21A-B is a chart plotting tumor growth of DU4475 (FIG. 21A) and MDA-MB-231 (FIG. 21B) breast tumors versus days after treatment with anti-human VEGFR-I antibody 18F1 of the present invention and anti-mouse VEGFR-I antibody MF1.

FIG. 24A is a chart of the number of tumor cells that migrated across a layer of MATRIGEL™ after treatment with anti-human VEGFR-I antibody 18F1 in the presence of VEGF-A or VEGF-B.

FIG. 24B are photomicrographs of stained migrated cells after treatment with anti-human VEGFR-I antibody 18F1 in the presence of VEGF-A and VEGF-B.

FIG. 25 is a chart plotting tumor growth of DU4475 (FIG. 25A) and MDA-MB-435 (FIG. 25B) breast tumors versus days after treatment with anti-VEGFR-I antibodies 18F1, 6F9 and 15F11.

FIG. 26 is a chart plotting growth of HT-29 (FIG. 26A), DLD-I (FIG. 26B) and GEO (FIG. 26C) colon cancer cells versus days after treatment with particular doses of anti-human VEGFR-I antibody 18F1.

FIG. 28 is a chart plotting tumor growth versus days after treatment with particular doses of anti-human anti-VEGFR-I antibody 18F1, anti-mouse anti-VEGFR-I antibody MF1, or both in MDA-MB-231 (FIG. 28A) and DU4475 (FIG. 28B) xenografts.

FIGS. 30A and B are charts plotting tumor growth versus days after treatment with 5-FU/LV or doxorubicin in combination with anti-human anti-VEGFR-I antibody 18F1 and anti-mouse anti-VEGFR-1 antibody MF1 in MDA-MB-231 xenografts.

FIG. 31 is a chart of total tumor cell count versus antibody concentration of various amounts of 18F1 in the presence of VEGF-A (FIG. 31A) or PIGF (FIG. 31B) following treatment with desferoxamine.

FIGS. 32A, B, and C are charts depicting the specificity of anti-human anti-VEGFR-1 antibody 18F1 and anti-mouse anti-VEGFR-1 antibody MF1.

DETAILED DESCRIPTION OF THE INVENTION

Figure 3:
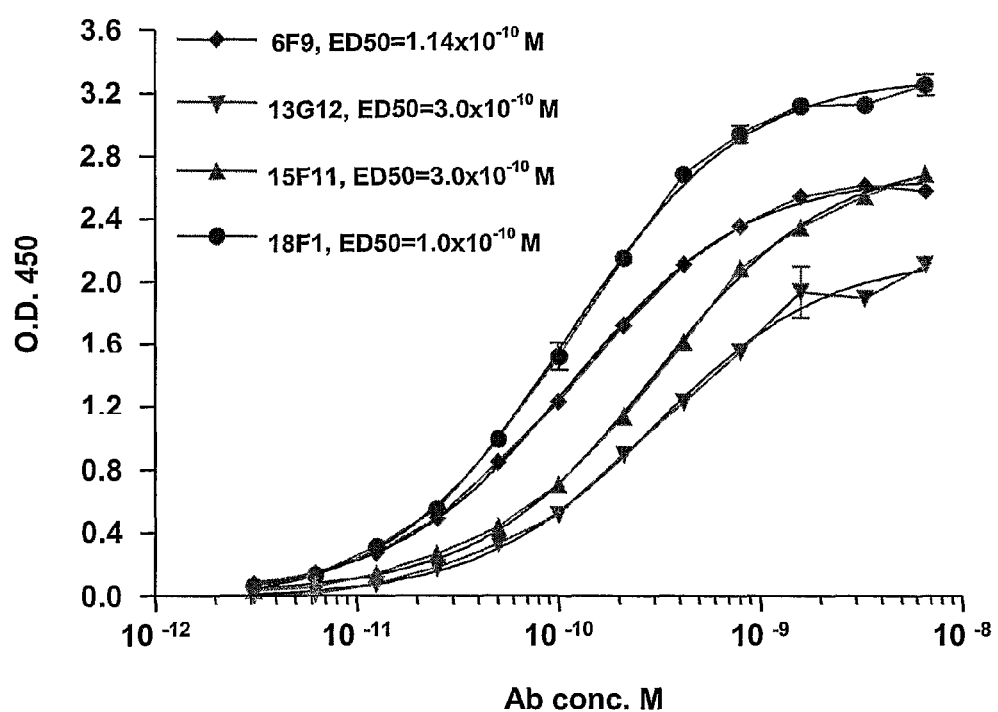
FIG. 3 is a chart depicting the results of an ELISA-based binding assay measuring in vitro binding activity of embodiments of anti-VEGFR-I antibodies of the present invention to VEGFR-I.

In an embodiment, the present invention provides a monoclonal antibodies and fragments thereof that specifically bind to VEGFR-I (such antibodies and fragments thereof referred to herein as "anti-VEGFR-1 antibodies" unless otherwise indicated). Anti-VEGFR-1 antibodies of the present invention comprise a light chain complementarity determining region-2 (CDR2) of SEQ ID NO: 2 and a light chain complementarity region-3 (CDR3) of SEQ ID NO: 3. Alternatively and preferably, anti-VEGFR-1 antibodies of the present invention comprise a light chain complementarity region-1 (CDR1) having the following sequence:

RASQSX$_1$ SSSYLA, where X$_1$ is V or G (SEQ ID NO: 1 or 4). Alternatively and preferably, anti-VEGFR-I antibodies of the present invention comprise a heavy chain CDR1 having the following sequence: GFX$_2$FSSYGMH, where X$_2$ is T or A (SEQ ID NO: 5 or 11). Alternatively and preferably, anti-VEGFR-I antibodies of the present invention comprise a heavy chain CDR2 having the following sequence:

VIWX$_3$ DGSNKYYADSVX$_4$ G, where X$_3$ is Y or F and X$_4$ is K or R (SEQ ID NO: 6, 9, or 12). Alternatively and also preferably, anti-VEGFR-1 antibodies of the present invention comprise a heavy chain CDR3 having the following sequence:

DHX$_5$ GSGX$_6$ HX$_7$ YX$_8$ YYGX$_9$ DV, where X$_5$ is F or Y; X$_6$ is A or V; X$_7$ is Y, S, or H; X$_8$ is Y or F; and X$_9$ is M or L (SEQ ID NO: 7, 8, 10, 13). The amino acid sequences of the CDRs of preferred anti-VEGFR-1 antibodies (designated as clones "6F9," "13G12," "15F11," and "18F1" (or "MC-18F1")) are set forth below in Table 1.

TABLE 1

CDR sequence of anti-VEGFR-1 antibodies

| Clone | CDR1 | CDR2 | CDR3 |
|---|---|---|---|
| Light Chain | | | |
| 6F9 | RASQSGSSSYLA (SEQ ID NO: 1) | GASSRAT (SEQ ID NO: 2) | QQYGSSPLT (SEQ ID NO: 3) |
| 13G12 | RASQSGSSSYLA (SEQ ID NO: 1) | GASSRAT (SEQ ID NO: 2) | QQYGSSPLT (SEQ ID NO: 3) |
| 15F11 | RASQSVSSSYLA (SEQ ID NO: 4) | GASSRAT (SEQ ID NO: 2) | QQYGSSPLT (SEQ ID NO: 3) |
| 18F1 | RASQSVSSSYLA (SEQ ID NO: 4) | GASSRAT (SEQ ID NO: 2) | QQYGSSPLT (SEQ ID NO: 3) |
| Heavy Chain | | | |
| 6F9 | GFTFSSYGMH (SEQ ID NO: 5) | VIWYDGSNKYYADSVKG (SEQ ID NO: 6) | DHFGSGAHYYYYGMDV (SEQ ID NO: 7) |
| 13G12 | GFTFSSYGMH (SEQ ID NO: 5) | VIWYDGSNKYYADSVKG (SEQ ID NO: 6) | DHYGSGAHYYYYGMDV (SEQ ID NO: 8) |
| 15F11 | GFTFSSYGMH (SEQ ID NO: 5) | VIWFDGSNKYYADSVKG (SEQ ID NO: 9) | DHYGSGAHSYYYGLDV (SEQ ID NO: 10) |
| 18F1 | GFAFSSYGMH (SEQ ID NO: 11) | VIWYDGSNKYYADSVRG (SEQ ID NO: 12) | DHYGSGVHHYFYYGLDV (SEQ ID NO: 13) |

In another embodiment, anti-VEGFR-I antibodies of the present invention have a light chain variable region (V$_L$) of SEQ ID NO: 14, 15, or 16 and/or a heavy chain variable region (V$_H$) of SEQ ID NO: 17, 18, 19, or 20. The amino acid sequences of the light and heavy chain variable regions of preferred anti-VEGFR-I antibodies of the present invention are set forth below in Table 2.

TABLE 2

Variable region sequence of anti-VEGFR-1 antibodies (underlined portions represent CDRs)

Clone

Light Chain

6F9     EIVLTQSPGTLSLSPGERATLSC<u>RASQSGSSSYLA</u>WYQQKPGQAPRLLIY<u>GASS
        RAT</u>GIPDRFSGSGSGTDFTLTISRLEPEDFAVYYC<u>QQYGSSPLT</u>FGGGTKVEIK
        RTVAAPSVFIFP
        SEQ ID NO: 14

13G12   EIVLTQSPGTLSLSPGERATLSC<u>RASQSGSSSYLA</u>WYQQKPGQAPRLLIY<u>GASS
        RAT</u>GIPDRFSGSGSGTDFTLTISRLEPEDFAVYYC<u>QQYGSSPLT</u>FGGGTKVEIK
        RTVAAPSVFIFP
        SEQ ID NO: 14

15F11   EIVLTQSPGTLSLSPGERATLSC<u>RASQSVSSSYLA</u>WYQQKPGQAPRLLIY<u>GASS
        RAT</u>GIPDRFSGSGSGTDFTLTISRLEPEDFAVYYC<u>QQYGSSPLT</u>FGQGTRLEIKR
        TVAAPSVFIFP
        SEQ ID NO: 15

18F1    EIVLTQSPGTLSLSPGERATLSC<u>RASQSVSSSYLA</u>WYQQKPGQAPRLLIY<u>GASS
        RAT</u>GIPDRFSGSGSGTDFTLTISRLEPEDFAVYYC<u>QQYGSSPLT</u>FGGGTKVEIK
        RTVAAPSVFIFP
        SEQ ID NO: 16

Heavy Chain

6F9     QVQLVESGGGVVQPGRSLRLSCAAS<u>GFTFSSYGMH</u>WVRQAPGKGLEWVA<u>VI
        WYDGSNKYYADSVKGR</u>FTISRDNSKNTVYLQMNSLRAEDTAVYHCTR<u>DHFG
        SGAHYYYYGMDV</u>WGQGTTVTVSS
        SEQ ID NO: 17

13G12   QVQLVESGGGVVQPGRSLRLSCAAS<u>GFTFSSYGMH</u>WVRQAPGKGLEWVA<u>VI
        WYDGSNKYYADSVKGR</u>FTISRDNSKNILYLQMNSLRAEDTAVYYCA<u>RDHY
        GSGAHYYYYGMDV</u>WGQGTTVTVSS
        SEQ ID NO: 18

15F11   QVQLVESGGGVVQPGRSLRLSCAAS<u>GFTFSSYGMH</u>WVRQAPGKGLEWVA<u>VI
        WFDGSNKYYADSVKGR</u>FTISRDNSKNTLYLQMNSLRAEDTAVYYCA<u>RDHYG
        SGAHSYYYYGLDV</u>WGQGTSVTVSS
        SEQ ID NO: 19

18F1    QAQVVESGGGVVQSGRSLRLSCAAS<u>GFAFSSYGMH</u>WVRQAPGKGLEWVA<u>VI
        WYDGSNKYYADSVRGR</u>FTISRDNSENTLYLQMNSLRAEDTAVYYCA<u>RDHYG
        SGVHHYFYYGLDV</u>WGQGTTVTVSS
        SEQ ID NO: 20

In a preferred embodiment, the anti-VEGFR-I antibodies of the present invention are human antibodies.

Anti-VEGFR-1 antibodies of the present invention include whole antibodies and antibody fragments that specifically bind to VEGFR-I. Non-limiting examples of types of antibodies according to the present invention include naturally occurring antibodies; single chain antibodies; multivalent single chain antibodies such as diabodies and tribodies; monovalent fragments such as Fab (Fragment, antigen binding), bivalent fragments such as $(FaV)_2$; Fv (fragment variable) fragments or derivatives thereof such as single chain Fv (scFv) fragments; and single domain antibodies that bind specifically to VEGFR-I.

Naturally occurring antibodies typically have two identical heavy chains and two identical light chains, with each light chain covalently linked to a heavy chain by an interchain disulfide bond and multiple disulfide bonds further linking the two heavy chains to one another. Individual chains can fold into domains having similar sizes (110-125 amino acids) and structures, but different functions. The light chain can comprise one $V_L$ and one constant domain ($C_L$). The heavy chain can also comprise one $V_H$ and/or depending on the class or isotype of antibody, three or four constant domains ($C_H1$, CH2, $C_H3$, and $C_H4$). In humans, the isotypes are IgA, IgD, IgE, IgG, and IgM, with IgA and IgG further subdivided into subclasses or subtypes ($IgA_{1-2}$ and $IgG_{1-4}$).

Single chain antibodies lack some or all of the constant domains of the whole antibodt from which they are derived. The peptide linkers used to produce the single chain antibodies may be flexible peptides selected to assure that the proper three-dimensional folding of the $V_L$ and $V_H$ domains occurs. Generally, the carboxyl terminus of the $V_L$ or $V_H$ sequence may be covalently linked by such a peptide linker to the amino acid terminus of a complementary VH or VL sequence. The linker is generally 10 to 50 amino acid residues, preferably 10 to 30 amino acid residues, more preferably 12 to 30 amino acid residues, and most preferably 15 to 25 amino acid residues. An example of such linker peptides include (Gly-Gly-Gly-Gly-Ser)$_3$ (SEQ ID NO: 28).

Multiple single chain antibodies, each single chain having one $V_H$ and one $V_L$ domain covalently linked by a first peptide linker, can be covalently linked by at least one or more peptide linkers to form a multivalent single chain antibody, which can be monospecific or multispecific. Each chain of a mulivalent single chain antibody includes a variable light chain fragment and a variable heavy chain fragment, and is linked by a peptide linker to at least one other chain.

Two single chain antibodies can be combined to form a diabody, also known as a trivalent dimer. Diabodies have two chains and two binding sites and can be monospecific or bispecific. Each chain of the diabody includes a $V_H$ domain connected to a $V_L$ domain. The domains are connected with linkers that are short enough to prevent pairing between domains on the same chain, thus driving the pairing between complementary domains on different chains to recreate the two antigen-binding sites.

Three single chain antibodies can be combined to form triabodies, also known as trivalent trimers. Triabodies are constructed with the amino acid terminus of a $V_L$ or $V_H$ domain directly fused to the carboxyl terminus of a $V_L$ or $V_H$ domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

Fab fragments refer to fragments of the antibody consisting of $V_L C_L V H C H_I$ domains. Those generated by papain digestion are referred to as "Fab" and do not retain the heavy chain hinge region. Those generated by pepsin digestion are referred to either as "(Fab')$_2$," in which case the interchain disulfide bonds are intact, or as Fab', in which case the disulfide bonds are not retained. Bivalent (Fab')$_2$ fragments have higher avidity for antigen than that of monovalent Fab fragments.

Fv fragments are the portion of an antibody consisting of the $V_L$ and $V_H$ domains and constitute the antigen-binding site. scFv is an antibody fragment containing a VL domain and $V_H$ domain on one polypeptide chain, wherein the N terminus of one domain and the C terminus of the other domain are joined by a flexible linker to allows the two fragments to associate to form a functional antigen binding site (see, for example U.S. Pat. No. 4,946,778 (Ladner et al), WO 88/09344, (Huston et al.), both of which are incorporated by reference herein). WO 92/01047 (McCafferty et al.), which is incorporated by reference herein, describes the display of scFv fragments on the surface of soluble recombinant genetic display packages, such as bacteriophage.

Single domain antibodies have a single variable domain that is capable of efficiently binding antigen. Examples of antibodies wherein binding affinity and specificity are contributed primarily by one or the other variable domain are known in the art. See, e.g., Jeffrey, P. D. et al., *Proc. Natl Acad. ScL* USA 90:10310-4 (1993), which is incorporated by reference herein and which discloses an anti-digoxin antibody which binds to digoxin primarily by the antibody heavy chain. Accordingly, single antibody domains can be identified that bind well to VEGF receptors. It is understood that, to make a single domain antibody from an antibody comprising a $V_H$ and a $V_L$ domain, certain amino acid substitutions outside the CDR regions may be desired to enhance binding, expression or solubility. For example, it may be desirable to modify amino acid residues that would otherwise be buried in the $V_H$-$V_L$ interface.

Each domain of anti-VEGFR-1 antibodies of the present invention may be a complete antibody heavy or light chain variable domain, or it may be a functional equivalent or a mutant or derivative of a naturally occuring domain, or a synthetic domain constructed, for example, in vitro using a technique such as one described in WO 93/11236 (Griffiths et al.). For instance, it is possible to join together domains corresponding to antibody variable domains which are missing at least one amino acid. The important characterizing feature is the ability of each domain to associate with a complementary domain to form an antigen binding site. Accordingly, the terms "variable heavy/light chain fragment" should not be construed to exclude variants which do not have a material effect on VEGFR-I binding specificity.

As used herein, an "anti-VEGFR-I antibody" include modifications of an anti-VEGFR-I antibody of the present invention that retain specificity for VEGFR-I. Such modifications include, but are not limited to, conjugation to an effector molecule such as a chemotherapeutic agent (e.g., cisplatin, taxol, doxorubicin) or cytotoxin (e.g., a protein, or a non-protein organic chemotherapeutic agent). Modifications further include, but are not limited to conjugation to detectable reporter moieties. Modifications that extend antibody half-life (e.g., pegylation) are also included.

Proteins and non-protein agents may be conjugated to the antibodies by methods that are known in the art. Conjugation methods include direct linkage, linkage via covalently attached linkers, and specific binding pair members (e.g., avidin-biotin). Such methods include, for example, that described by Greenfield et al., *Cancer Research* 50, 6600-6607 (1990), which is incorporated by reference herein, for the conjugation of doxorubicin and those described by Amon et al., *Adv. Exp. Med. Biol.* 303, 79-90 (1991) and by Kiseleva et al, *Mol. Biol. (USSR)*25, 508-514 (1991), both of which are incorporated by reference herein, for the conjugation of platinum compounds.

Anti-VEGFR-I antibodies of the present invention also include those for which binding characteristics have been improved by direct mutation, methods of affinity maturation, phage display, or chain shuffling. Affinity and specificity may be modified or improved by mutating any of the CDRs of the antibodies of the present invention and screening for antigen binding sites having the desired characteristics (see, e.g., Yang et al., *J. Mol. Biol,* 254: 392-403 (1995), which is incorporated by reference herein). The CDRs may be mutated in a variety of ways that are known to one of skill in the art. For example, one way is to randomize individual residues or combinations of residues so that in a population of otherwise identical antigen binding sites, all twenty amino acids are found at particular positions. Alternatively, mutations are induced over a range of CDR residues by error prone PCR methods (see, e.g., Hawkins et al., *J. Mol. Biol,* 226: 889-896 (1992), which is incorporated by reference herein). For example, phage display vectors containing heavy and light chain variable region genes may be propagated in mutator strains of *E. coli* (see, e.g., Low et al., *J. Mol Biol,* 250: 359-368 (1996), which is incorporated by reference herein).

Anti-VEGFR-I antibodies also include functional equivalents that include polypeptides with amino acid sequences substantially the same as the amino acid sequence of the variable or hypervariable regions of the antibodies of the present invention. "Substantially the same" amino acid sequence includes an amino acid sequence with at least 70%, preferably at least 80%, and more preferably at least 90% identity to another amino acid sequence when the amino acids of the two sequences are optimally aligned and compared to determine exact matches of amino acids between the two sequences. "Substantially the same" amino acid sequence also includes an amino acid sequence with at least 70%, preferably at least 80%, and more preferably at least 90% homology to another amino acid sequence, as determined by the FASTA search method in accordance with Pearson and Lipman, Proc. Natl. Acad. Sci. USA 85, 2444-8 (1988).

As stated earlier, anti-VEGFR-I antibodies of the present invention specifically bind to VEGFR-I. Such antibodies can be monospecific or bispecific so long as one antigen-binding site is specific for VEGFR-I. Antibody specificity, which refers to selective recognition of an antibody for a particular epitope of an antigen, of antibodies for VEGFR-I can be determined based on affinity and/or avidity. Affinity, represented by the equilibrium constant for the dissociation of an antigen with an antibody ($K_d$), measures the binding strength between an antigenic determinant (epitope) and an antibody binding site. Avidity is the measure of the strength of binding between an antibody with its antigen. Antibodies typically bind with a $K_d$ of $10^{-5}$ to $10^{-11}$ liters/mole. Any $K_d$ less than $10^{-4}$ liters/mole is generally considered to indicate non-specific binding. The lesser the value of the $K_d$, the stronger the binding strength between an antigenic determinant and the antibody binding site.

Anti-VEGFR-I antibodies of the present invention specifically bind to the extracellular region of VEGFR-I and preferably neutralize activation of VEGFR-I by preventing binding of a ligand of VEGFR-I to the receptor. In such preferable embodiments, the antibody binds VEGFR-I at least as strongly as the natural ligands of VEGFR-I (including VEGF (A), VEGF-B and PlGF).

Neutralizing activation of VEGFR-I includes diminishing, inhibiting, inactivating, and/or disrupting one or more of the activities associated with signal transduction. Such activities include receptor dimerization, autophosphorylation of VEGFR-I, activation of VEGFR-I's internal cytoplasmic tyrosine kinase domain, and initiation of multiple signal transduction and transactivation pathways involved in regulation of DNA synthesis (gene activation) and cell cycle progression or division. One measure of VEGFR-I neutralization is inhibition of the tyrosine kinase activity VEGFR-I. Tyrosine kinase inhibition can be determined using well-known methods such as phosphorylation assays which measuring the autophosphorylation level of recombinant kinase receptor, and/or phosphorylation of natural or synthetic substrates. Phosphorylation can be detected, for example, using an antibody specific for phosphotyrosine in an ELISA assay or on a western blot. Some assays for tyrosine kinase activity are described in Panek et al., *J. Pharmacol. Exp. Them.*, 283: 1433-44 (1997) and Batley et al, *Life ScL,* 62: 143-50 (1998), both of which are incorporated by reference.

In addition, methods for detection of protein expression can be utilized to determine whether an antibody neutralizes activation of VEGFR-I, wherein the proteins being measured are regulated by VEGFR-I tyrosine kinase activity. These methods include immunohistochemistry (IHC) for detection of protein expression, fluorescence in situ hybridization (FISH) for detection of gene amplification, competitive radioligand binding assays, solid matrix blotting techniques, such as Northern and Southern blots, reverse transcriptase polymerase chain reaction (RT-PCR) and ELISA. See, e.g., Grandis et al., *Cancer,* 78:1284-92. (1996); Shimizu et al., *Japan J. Cancer Res.*, 85:567-71 (1994); Sauter et al., *Am. J. Path.*, 148:1047-53 (1996); Collins, *Glia,* 15:289-96 (1995); Radinsky et al., *Clin. Cancer Res.*, 1:19-31 (1995); Petrides et al., *Cancer Res.*, 50:3934-39 (1990); Hoffmann et al., *Anti-cancer Res.*, 17:4419-26 (1997); Wikstrand et al., *Cancer Res.*, 55:3140-48 (1995), all of which are incorporated by reference.

In vivo assays can also be utilized to detect VEGFR-I neutralization. For example, receptor tyrosine kinase inhibition can be observed by mitogenic assays using cell lines stimulated with receptor ligand in the presence and absence of inhibitor. For example, HUVEC cells (ATCC) stimulated with VEGF(A) or VEGF-B can be used to assay VEGFR-I inhibition. Another method involves testing for inhibition of growth of VEGF-expressing tumor cells, using for example, human tumor cells injected into a mouse. See e.g., U.S. Pat. No. 6,365,157 (Rockwell et al.), which is incorporated by reference herein.

Of course, the present invention is not limited by any particular mechanism of VEGFR-I neutralization. Anti-VEGFR-I antibodies of the present invention can, for example, bind externally to VEGFR-I, block binding of ligand to VEGFR-I and subsequent signal transduction mediated via receptor-associated tyrosine kinase, and prevent phosphorylation of VEGFR-I and other downstream proteins in the signal transduction cascade. The receptor-antibody complex can also be internalized and degraded, resulting in receptor cell surface down-regulation. Matrix metalloproteinases, which function is tumor cell invasion and metastasis, can also be down-regulated by anti-VEGFR-I antibodies of the present invention.

Human anti-VEGFR-I antibodies can be obtained from naturally occurring antibodies, or Fab or scFv phage display libraries constructed, for example, from human heavy chain and light chain variable region genes and the CDR sequences of the anti-VEGFR-I antibodies of the present invention can be inserted into such human anti-VEGFR-I antibodies.

Human anti-VEGFR-I antibodies can be produced by methods well known to one of skill in the art. Such methods include the hybridoma method using transgenic mice described by Kohler and Milstein, *Nature,* 256: 495-497 (1975) and Campbell, Monoclonal Antibody Technology, The Production and Characterization of Rodent and Human Hybridomas, Burdon et ah, Eds., Laboratory Techniques in Biochemistry and Molecular Biology, Volume 13, Elsevier Science Publishers, Amsterdam (1985), all of which are incorporated by reference herein; as well as by the recombinant DNA method described by Huse et al., *Science,* 246, 1275-1281 (1989), which is incorporated by reference herein.

Antibody fragments can be produced by cleaving a whole antibody, or by expressing DNA that encodes the fragment. Fragments of antibodies may be prepared by methods described by Lamoyi et al., *J. Immunol. Methods,* 56: 235-243 (1983) and by Parham, *J. Immunol.* 131: 2895-2902 (1983), both of which are incorporated by reference herein. Such fragments may contain one or both Fab fragments or the $F(ab')_2$ fragment. Such fragments may also contain single-chain fragment variable region antibodies, i.e. scFv, diabodies, or other antibody fragments. Methods of producing such antibodies are disclosed in PCT Application WO 93/21319, European Patent Application No. 239,400; PCT Application WO 89/09622; European Patent Application 338,745; and European Patent Application EP 332,424, all of which are incorporated by reference herein.

in another embodiment, the present invention provides polynucleotides encoding the anti-VEGFR-I antibodies of the present invention. Such polynucleotides encode the light chain CDR2 of SEQ ID NO.: 2, the light chain CDR3 of SEQ ID NO: 3, and, preferably, one or more of the other CDRs listed in Table 1. Table 3 sets forth the nucleic acid sequences of preferred anti-VEGFR-I antibodies.

TABLE 3

Nucleotide sequence of anti-VEGFR-1 antibodies

Clone

Light Chain

6F9    GAAATTGTGTTGACGCAGTCTCCAGGCACCCTGTCCTTGTCTCCAGGGGAA
AGAGCCACCCTCTCCTGCAGGGCCAGTCAGAGTGGTAGCAGCAGCTACTT
AGCCTGGTACCAGCAGAAACCTGGCCAGGCTCCCAGGCTCCTCATCTATG
GTGCATCCAGCAGGGCCACTGGCATCCCAGACAGGTTCAGTGGCAGTGGG
TCTGGGACAGACTTCACTCTCACCATCAGCAGACTGGAGCCTGAAGATTTT
GCAGTGTATTACTGTCAGCAGTATGGTAGCTCACCGCTCACTTTCGGCGGA
GGGACCAAGGTGGAGATCAAACGAACTGTGGCTGCACCATCTGTCTTCAT
CTTCCCG
SEQ ID NO: 21

13G12    GAAATTGTGTTGACGCAGTCTCCAGGCACCCTGTCCTTGTCTCCAGGGGAA
AGAGCCACCCTCTCCTGCAGGGCCAGTCAGAGTGGTAGCAGCAGCTACTT
AGCCTGGTACCAGCAGAAACCTGGCCAGGCTCCCAGGCTCCTCATCTATG
GTGCATCCAGCAGGGCCACTGGCATCCCAGACAGGTTCAGTGGCAGTGGG
TCTGGGACAGACTTCACTCTCACCATCAGCAGACTGGAGCCTGAAGATTTT
GCAGTGTATTACTGTCAGCAGTATGGTAGCTCACCGCTCACTTTCGGCGGA
GGGACCAAGGTGGAGATCAAACGAACTGTGGCTGCACCATCTGTCTTCAT
CTTCCCG
SEQ ID NO: 21

15F11    GAAATTGTGTTGACGCAGTCTCCAGGCACCCTGTCTTTGTCTCCAGGGGAA
AGAGCCACCCTCTCCTGCAGGGCCAGTCAGAGTGTTAGCAGCAGCTACTT
AGCCTGGTACCAGCAGAAACCTGGCCAGGCTCCCAGGCTCCTCATCTATG
GTGCATCCAGCAGGGCCACTGGCATCCCAGACAGGTTCAGTGGCAGTGGG
TCTGGGACAGACTTCACTCTCACCATCAGCAGACTGGAGCCTGAAGATTTT
GCAGTGTATTACTGTCAGCAGTATGGTAGCTCACCTCTCACCTTCGGCCAA
GGGACACGACTGGAGATTAAACGAACTGTGGCTGCACCATCTGTCTTCAT
CTTCCCG
SEQ ID NO: 22

18F1    GAAATTGTGTTGACGCAGTCTCCAGGCACCCTGTCTTTGTCTCCAGGGGAA
AGAGCCACCCTCTCCTGCAGGGCCAGTCAGAGTGTTAGCAGCAGCTACTT
AGCCTGGTACCAGCAGAAACCTGGCCAGGCTCCCAGGCTCCTCATCTATG
GTGCATCCAGCAGGGCCACTGGCATCCCAGACAGGTTCAGTGGCAGTGGG
TCTGGGACAGACTTCACTCTCACCATCAGCAGACTGGAGCCTGAAGATTTT
GCAGTGTATTACTGTCAGCAGTATGGTAGCTCACCGCTCACTTTCGGCGGA
GGGACCAAGGTGGAGATCAAACGAACTGTGGCTGCACCATCTGTCTTCAT
CTTTCCCG
SEQ ID NO: 23

Heavy Chain

6F9    CAGGTGCAGCTGGTGGAGTCTGGGGGAGGCGTGGTCCAGCCTGGGAGGTC
CCTGAGACTCTCCTGTGCAGCGTCTGGATTCACCTTCAGTAGTTATGGCAT
GCACTGGGTCCGCCAGGCTCCAGGCAAGGGGCTGGAGTGGGTGGCAGTTA
TATGGTATGATGGAAGTAATAAATACTATGCAGACTCCGTGAAGGGCCGA
TTCACCATCTCCAGAGACAATTCCAAGAACACGGTGTATCTGCAAATGAA
CAGCCTGAGAGCCGAGGACACGGCTGTGTATCACTGTACGAGAGATCACT
TTGGTTCGGGGGCTCACTACTACTACTACTACGGTATGGACGTCTGGGGCC
AAGGGACCACGGTCACCGTCTCCTCA
SEQ ID NO: 24

13G12    CAGGTGCAGCTGGTGGAGTCTGGGGGAGGCGTGGTCCAGCCTGGGAGGTC
CCTGAGACTCTCCTGTGCAGCGTCTGGATTCACCTTCAGTAGCTATGGCAT
GCACTGGGTCCGCCAGGCTCCAGGCAAGGGGCTGGAGTGGGTGGCAGTTA
TATGGTATGATGGAAGTAATAAATACTATGCAGACTCCGTGAAGGGCCGA
TTCACCATCTCCAGAGACAATTCCAAGAACACGCTGTATCTGCAAATGAA
CAGCCTGAGAGCCGAGGACACGGCTGTGTATTACTGTGCGAGAGATCACT
ATGGTTCGGGGGCTCACTACTACTACTACGGTATGGACGTCTGGGGC
CAAGGGACCACGGTCACCGTCTCCTCA
SEQ ID NO: 25

15F11    CAGGTGCAGCTGGTGGAGTCTGGGGGAGGCGTGGTCCAGCCTGGGAGGTC
CCTGAGACTCTCCTGTGCAGCGTCTGGATTCACCTTCAGTAGCTATGGCAT
GCACTGGGTCCGCCAGGCTCCAGGCAAGGGGCTGGAGTGGGTGGCAGTTA
TATGGTTTGATGGAAGTAATAAATACTATGCAGACTCCGTGAAGGGCCGA
TTCACCATCTCCAGAGACAATTCCAAGAACACGCTGTATCTGCAAATGAA
CAGCCTGAGAGCCGAGGACACGGCTGTGTATTACTGTGCGAGAGATCACT
ATGGTTCGGGGGCTCACTCCTACTACTACGGTTTGGACGTTTGGGGCC
AAGGGACCTCGGTCACCGTCTCCTCA
SEQ ID NO: 26

18F1    CAGGCGCAGGTGGTGGAGTCTGGGGGAGGCGTGGTCCAGTCTGGGAGGTC
CCTGAGACTCTCCTGTGCAGCGTCTGGATTCGCCTTCAGTAGCTACGGCAT

TABLE 3-continued

Nucleotide sequence of anti-VEGFR-1 antibodies

Clone

```
GCACTGGGTCCGCCAGGCTCCAGGCAAGGGGCTGGAGTGGGTGGCAGTTA
TATGGTATGATGGAAGTAATAAATACTATGCAGACTCCGTGAGGGGCCGA
TTCACCATCTCCAGAGACAATTCCGAGAACACGCTGTATCTGCAAATGAA
CAGCCTGAGAGCCGAGGACACCGCTGTGTATTACTGTGCCAGAGATCACT
ATGGTTCGGGGGTGCACCACTATTTCTACTACGGTCTGGACGTCTGGGCC
AAGGGACCACGGTCACCGTCTCCTCA
SEQ ID NO: 27
```

DNA encoding human antibodies can be prepared by recombining DNA encoding human constant regions and variable regions, other than the CDRs, derived substantially or exclusively from the corresponding human antibody regions and DNA encoding CDRs derived from a human (SEQ ID NOs: 1-4 for the light chain variable domain CDRs and SEQ ID Nos: 5-13 for the heavy chain variable domain CDRs.

Polynucleotides encoding anti-VEGFR-I antibodies of the present invention include polynucleotides with nucleic acid sequences that are substantially the same as the nucleic acid sequences of the polynucleotides of the present invention. "Substantially the same" nucleic acid sequence is defined herein as a sequence with at least 70%, preferably at least 80%, and more preferably at least 90% identity to another nucleic acid sequence when the two sequences are optimally aligned (with appropriate nucleotide insertions or deletions) and compared to determine exact matches of nucleotides between the two sequences.

Suitable sources of DNAs that encode fragments of antibodies include any cell, such as hybridomas and spleen cells, that express the full-length antibody. The fragments may be used by themselves as antibody equivalents, or may be recombined into equivalents, as described above. The DNA deletions and recombinations described in this section may be carried out by known methods, such as those described in the published patent applications listed above in the section entitled "Functional Equivalents of Antibodies" and/or other standard recombinant DNA techniques, such as those described below. Another source of DNAs are single chain antibodies produced from a phage display library, as is known in the art.

Additionally, the present invention provides expression vectors containing the polynucleotide sequences previously described operably linked to an expression sequence, a promoter and an enhancer sequence. A variety of expression vectors for the efficient synthesis of antibody polypeptide in prokaryotic, such as bacteria and eukaryotic systems, including but not limited to yeast and mammalian cell culture systems have been developed. The vectors of the present invention can comprise segments of chromosomal, non-chromosomal and synthetic DNA sequences.

Any suitable expression vector can be used. For example, prokaryotic cloning vectors include plasmids from *E. coli*, such as colEl,pCRl,pBR322,pMB9,pUC, pKSM, and RP4. Prokaryotic vectors also include derivatives of phage DNA such as Ml3 and other filamentous single-stranded DNA phages. An example of a vector useful in yeast is the 2µ plasmid. Suitable vectors for expression in mammalian cells include well-known derivatives of SV-40, adenovirus, retrovirus-derived DNA sequences and shuttle vectors derived from combination of functional mammalian vectors, such as those described above, and functional plasmids and phage DNA.

Additional eukaryotic expression vectors are known in the art {e.g., P J. Southern & P. Berg, *J. Mol. Appl. Genet*, 1:327-341 (1982); Subramani et al, *Mol. Cell. Biol*, 1: 854-864 (1981); Kaufinann & Sharp, "Amplification And Expression of Sequences Cotransfected with a Modular Dihydrofolate Reductase Complementary DNA Gene," *J. Mol. Biol*, 159: 601-621 (1982); Kaufhiann & Sharp, *Mol. Cell. Biol*, 159: 601-664 (1982); Scahill et al., "Expression And Characterization Of The Product Of A Human Immune Interferon DNA Gene In Chinese Hamster Ovary Cells," *Proc. Nat'l Acad. ScL USA*, 80:4654-4659 (1983); Urlaub & Chasin, *Proc. Nat'l Acad. ScL USA*, 77:4216-4220, (1980), all of which are incorporated by reference herein).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

The present invention also provides recombinant host cells containing the expression vectors previously described. Anti-VEGFR-I antibodies of the present invention can be expressed in cell lines other than in hybridomas. Nucleic acids, which comprise a sequence encoding a polypeptide according to the invention, can be used for transformation of a suitable mammalian host cell.

Cell lines of particular preference are selected based on high level of expression, constitutive expression of protein of interest and minimal contamination from host proteins. Mammalian cell lines available as hosts for expression are well known in the art and include many immortalized cell lines, such as but not limited to, Chinese Hamster Ovary (CHO) cells, Baby Hamster Kidney (BHK) cells and many others. Suitable additional eukaryotic cells include yeast and other fungi. Useful prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, *Pseudomonas, Bacillus*, such as *Bacillus subtilis*, and *Streptomyces*.

These present recombinant host cells can be used to produce an antibody by culturing the cells under conditions permitting expression of the antibody and purifying the antibody from the host cell or medium surrounding the host cell.

Targeting of the expressed antibody for secretion in the recombinant host cells can be facilitated by inserting a signal or secretory leader peptide-encoding sequence {See, Shokri et al, (2003) *Appl Microbiol Biotechnol.* 60(6): 654-664, Nielsen et al, *Prot. Eng.*, 10:1-6 (1997); von Heinje et al., *Nucl. Acids Res.*, 14:4683-4690 (1986), all of which are incorporated by reference herein) at the 5' end of the antibody-encoding gene of interest. These secretory leader peptide elements can be derived from either prokaryotic or eukaryotic sequences. Accordingly suitably, secretory leader peptides are used, being amino acids joined to the N-terminal end of a polypeptide to direct movement of the polypeptide out of the host cell cytosol and secretion into the medium.

The anti-VEGFR-1 antibodies of the present invention can be fused to additional amino acid residues. Such amino acid residues can be a peptide tag to facilitate isolation, for example. Other amino acid residues for homing of the antibodies to specific organs or tissues are also contemplated.

In another embodiment, the present invention provides methods of treating a medical condition by administering a therapeutically effective amount of an anti-VEGFR-I antibody according to the present invention to a mammal in need thereof. Therapeutically effective means an amount effective to produce the desired therapeutic effect, such as inhibiting tyrosine kinase activity.

In a preferred embodiment, the present invention provides a method of reducing tumor growth or inhibiting angiogenesis by administering a therapeutically effective amount of an anti-VEGFR-I antibody of the present invention to a mammal in need thereof. While not intended to be bound to a particular mechanism, the conditions that may be treated by the present methods include, for example, those in which tumor growth or pathogenic angiogenesis is stimulated through a VEGFR paracrine and/or autocrine loop.

With respect to reducing tumor growth, such tumors include primary tumors and metastatic tumors, as well as refractory tumors. Refractory tumors include tumors that fail to respond or are resistant to other forms of treatment such as treatment with chemotherapeutic agents alone, antibodies alone, radiation alone or combinations thereof. Refractory tumors also encompass tumors that appear to be inhibited by treatment with such agents, but recur up to five years, sometimes up to ten years or longer after treatment is discontinued.

Anti-VEGFR-I antibodies of the present invention are useful for treating tumors that express VEGFR-I. Such tumors are characteristically sensitive to VEGF present in their environment, and may further produce and be stimulated by VEGF in an autocrine stimulatory loop. The method is therefore effective for treating a solid or non-solid tumor that is not vascularized, or is not yet substantially vascularized.

Examples of solid tumors which may be accordingly treated include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which anti-VEGFR-1 antibodies of the present invention are effective include squamous cell carcinoma, basal cell carcinoma and skin cancers that can be treated by suppressing the growth of malignant keratinocytes, such as human malignant keratinocytes.

Examples of non-solid tumors include leukemia, multiple myeloma and lymphoma. Some examples of leukemias include acute myelogenous leukemia (AML), chronic myelogenous leukemia (CML), acute lymphocytic leukemia (ALL), chronic lymphocytic leukemia (CLL), erythrocytic leukemia or monocytic leukemia. Some examples of lymphomas include Hodgkin's and non-Hodgkin's lymphoma.

With respect to inhibiting aiigiogenesis, anti-VEGFR-I antibodies of the present invention are effective for treating subjects with vascularized tumors or neoplasms, or angiogenic diseases characterized by excessive angiogenesis. Such tumors and neoplasms include, for example, malignant tumors and neoplasms, such as blastomas, carcinomas or sarcomas, and highly vascular tumors and neoplasms. Cancers that may be treated by the methods of the present invention include, for example, cancers of the brain, genitourinary tract, lymphatic system, stomach, renal, colon, larynx and lung and bone. Non-limiting examples further include epidermoid tumors, squamous tumors, such as head and neck tumors, colorectal tumors, prostate tumors, breast tumors, lung tumors, including lung adenocarcinoma and small cell and non-small cell lung tumors, pancreatic tumors, thyroid tumors, ovarian tumors, and liver tumors. The method is also used for treatment of vascularized skin cancers, including squamous cell carcinoma, basal cell carcinoma, and skin cancers that can be treated by suppressing the growth of malignant keratinocytes, such as human malignant keratinocytes. Other cancers that can be treated include Kaposi's sarcoma, CNS neoplasms (neuroblastomas, capillary hemangioblastomas, meningiomas and cerebral metastases), melanoma, gastrointestinal and renal carcinomas and sarcomas, rhabdomyosarcoma, glioblastoma, including glioblastoma multiforme, and leiomyosarcoma.

Non-limiting examples of pathological angiogenic conditions characterized by excessive angiogenesis involving, for example inflammation and/or vascularization include atherosclerosis, rheumatoid arthritis (RA), neovascular glaucoma, proliferative retinopathy including proliferative diabetic retinopathy, macular degeneration, hemangiomas, angiofibromas, and psoriasis. Other non-limiting examples of non-neoplastic angiogenic disease are retinopathy of prematurity (retrolental fibroplastic), corneal graft rejection, insulin-dependent diabetes mellitus, multiple sclerosis, myasthenia gravis, Crohn's disease, autoimmune nephritis, primary biliary cirrhosis, psoriasis, acute pancreatitis, allograph rejection, allergic inflammation, contact dermatitis and delayed hypersensitivity reactions, inflammatory bowel disease, septic shock, osteoporosis, osteoarthritis, cognition defects induced by neuronal inflammation, Osier-Weber syndrome, restinosis, and fungal, parasitic and viral infections, including cytomegaloviral infections.

The identification of medical conditions treatable by anti-VEGFR-I antibodies of the present invention is well within the ability and knowledge of one skilled in the art. For example, human individuals who are either suffering from a clinically significant neoplastic or angiogenic disease or who are at risk of developing clinically significant symptoms are suitable for administration of the present VEGF receptor antibodies. A clinician skilled in the art can readily determine, for example, by the use of clinical tests, physical examination and medical/family history, if an individual is a candidate for such treatment.

Anti-VEGFR-I antibodies of the present invention can be administered for therapeutic treatments to a patient suffering from a tumor or angiogenesis associated pathologic condition in an amount sufficient to prevent, inhibit, or reduce the progression of the tumor or pathologic condition. Progression includes, e.g, the growth, invasiveness, metastases and/or recurrence of the tumor or pathologic condition. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition. It should be noted, however, that the present invention is not limited to any particular dose.

hi another embodiment, the present invention provides a method of treating a medical condition by administering an anti-VEGFR-I antibody of the present invention in combination with one or more other agents. For example, an embodiment of the present invention provides a method of treating a medical condition by administering an anti-VEGFR-I antibody of the present invention with an antineoplastic or antiangiogenic agent. The anti-VEGFR-I antibody can be chemically or biosynthetically linked to one or more of the antineoplastic or antiangiogenic agents.

Any suitable antineoplastic agent can be used, such as a chemotherapeutic agent or radiation. Examples of chemotherapeutic agents include, but are not limited to, cisplatin, doxorubicin, cyclophosphamide, paclitaxel, irinotecan (CPT-II), topotecan or a combination thereof. When the antineoplastic agent is radiation, the source of the radiation can be either external (external beam radiation therapy—EBRT) or internal (brachytherapy—BT) to the patient being treated.

Further, anti-VEGFR-I antibodies of the present invention maybe administered with antibodies that neutralize other receptors involved in tumor growth or angiogenesis. One example of such a receptor is VEGFR-2/KDR. In an embodiment, an anti-VEGR-I antibody of the present invention is used in combination with a receptor antagonist that binds specifically to VEGFR-2. Particularly preferred are antigen-binding proteins that bind to the extracellular domain of VEGFR-2 and block binding by any one of its ligands, such as VEGF(A), VEGF-C, VEGF-D, or VEGF-E.

Another example of such a receptor is EGFR. hi an embodiment of the present invention, an anti-VEGFR-I antibody is used in combination with an EGFR antagonist. An EGFR antagonist can be an antibody that binds to EGFR or a ligand of EGFR and inhibits binding of EGFR to its ligand. Ligands for EGFR include, for example, EGF, TGF-ce amphiregulin, heparin-binding EGF (HB-EGF) and betarecullulin. EGF and TGF-α are thought to be the main endogenous ligands that result in EGFR-mediated stimulation, although TGF-α has been shown to be more potent in promoting angiogenesis. It should be appreciated that the EGFR antagonist can bind externally to the extracellular portion of EGFR, which may or may not inhibit binding of the ligand, or internally to the tyrosine kinase domain. Examples of EGFR antagonists that bind EGFR include, without limitation, biological molecules, such as antibodies (and functional equivalents thereof) specific for EGFR, and small molecules, such as synthetic kinase inhibitors that act directly on the cytoplasmic domain of EGFR.

Other examples of growth factor receptors involved in tumorigenesis are the receptors for platelet-derived growth factor (PDGFR), insulin-like growth factor (IGFR), nerve growth factor (NGFR), and fibroblast growth factor (FGFR).

In an additional alternative embodiment, the present invention provides a method of treating a medical condition by administering an anti-VEGFR-I antibody of the present invention in combination with one or more suitable adjuvants, such as, for example, cytokines (IL-IO and IL-1 3, for example) or other immune stimulators. See, e.g., Larrivee et al, supra.

In a combination therapy, the anti-VEGFR-I antibody can be administered before, during, or after commencing therapy with another agent, as well as any combination thereof, i.e., before and during, before and after, during and after, or before, during and after commencing the antineoplastic agent therapy. For example, an anti-VEGFR-I antibody of the present invention may be administered between 1 and 30 days, preferably 3 and 20 days, more preferably between 5 and 12 days before commencing radiation therapy. The present invention, however is not limited to any particular administration schedule. The dose of the other agent administered depends on numerous factors, including, for example, the type of agent, the type and severity of the medical condition being treated and the route of administration of the agent. The present invention, however, is not limited to any particular dose.

Any suitable method or route can be used to administer an anti-VEGFR-I antibody of the present invention, and optionally, to coadminister antineoplastic agents and/or antagonists of other receptors. Routes of administration include, for example, oral, intravenous, intraperitoneal, subcutaneous, or intramuscular administration. It should be emphasized, however, that the present invention is not limited to any particular method or route of administration.

It is noted that an anti-VEGFR-I antibody of the present invention can be administered as a conjugate, which binds specifically to the receptor and delivers a toxic, lethal payload following ligand-toxin internalization.

It is understood that anti-VEGFR-I antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection may, as is well known in the art, be formulated so as to provide quick, sustained or delayed release of the active ingredient after administration to the mammal.

Although human antibodies of the invention are particularly useful for administration to humans, they may be administered to other mammals as well. The term "mammal" as used herein is intended to include, but is not limited to, humans, laboratory animals, domestic pets and farm animals.

The present invention also includes kits for inhibiting tumor growth and/or angiogenesis comprising a therapeutically effective amount of an anti-VEGFR-I antibody of the present invention. The kits can further contain any suitable antagonist of, for example, another growth factor receptor involved in tumorigenesis or angiogenesis (e.g., VEGFR-2/FKDR, EGFR, PDGFR, IGFR, NGFR, FGFR, etc, as described above). Alternatively, or in addition, the kits of the present invention can further comprise an antineoplastic agent. Examples of suitable antineoplastic agents in the context of the present invention have been described herein. The kits of the present invention can further comprise an adjuvant, examples of which have also been described above.

In another embodiment, the present invention provides investigative or diagnostic methods using anti-VEGFR-I antibodies of the present invention in vivo or in vitro. In such methods, anti-VEGFR-I antibodies can be linked to target or reporter moieties.

EXAMPLES

The following examples do not include detailed descriptions of conventional methods, such as those employed in the construction of vectors and plasmids, the insertion of genes encoding polypeptides into such vectors and plasmids, or the introduction of plasmids into host cells. Such methods are well known to those of ordinary skill in the art and are described in numerous publications including Sambrook, J., Fritsch, E. F. and Maniatis, T. (1989), Molecular Cloning: A Laboratory Manual, 2nd edition, Cold Spring Harbor Laboratory Press, which is incorporated by reference herein.

Materials

AU reagents and chemicals were purchased from Sigma (St. Louis, Mo.) unless otherwise noted. Human VEGF165 and soluble recombinant human VEGFR-I alkaline phosphatase (rhuVEGFR-I AP) proteins were expressed in stably transfected cells and purified from cell culture supernatant following the procedures known to one skilled in the art (Tessler, *J Biol. Chem.*, 269:12456-12461 (1994), which is incorporated by reference herein). PlGF and soluble recombinant VEGFR-I Fc (rhuVEGFR-1 Fc) proteins were purchased from (R&D Systems Inc. Minneapolis, Minn.). Cell cultureware and assay plates were purchased from (BD Biosciences, Bedford, Mass.).

Cell Lines

The human breast cancer cell lines DU4475, MDA-MB-231, MDA-MB-435, and mouse myeloma cell lines P3-X63-Ag8.653 and NSO were obtained from American Type Tissue Culture Collection (Manassas, Va.). P3-X63-Ag8.653 Bcl/2 transfectant cell line was created in house as previously described (Ray S, Diamond B. Proc Natl Acad Sci USA. 91:5548-51, 1994). The tumor cells were maintained in RPMII 640 medium (Invitrogen/Life Technologies, Inc., Rockville, Md.) containing 10% FCS (Hyclone, Logan, Utah). Porcine aorta endothelial VEGFR-I expressing cell line was provided by Dr. L. Claesson-Welsh, Uppsala University, and cultured in F12 medium (Invitrogen/Life Technologies, Inc., Rockville, Md.) containing 10% FCS (Hyclone, Logan, Utah). All cells were maintained at 37° C. in a humidified, 5% CO2 atmosphere.

Example 1

Generation of Anti-VEGFR 1 Antibodies

Human anti-VEGFR-I monoclonal antibodies (referred to herein as "anti-VEGFR-I antibodies") were generated by a standard hybridoma technology (Harlow & Lane, ed., Antibodies: A Laboratory Manual, Cold Spring Harbor, 211-213 (1998), which is incorporated by reference herein) using KM transgenic mice (Medarex, San Jose, Calif.), which produce human immunoglobulin gamma heavy and kappa light chains. KM mice were immunized subcutaneously (s.c.) with VEGFR-I fragment crystallization (Fc) in complete Freund's adjuvant. Animals were intraperitoneally (i.p.) boosted three times with the same VEGFR-I protein in incomplete Freund's adjuvant before fusion. The animals were rested for a month before they received the final i.p. boost of 25 micrograms of VEGFR-I protein in phosphate buffer solution (PBS). Four days later, splenocytes were harvested from the immunized mouse and fused with P3-X63-Ag8.653 Bcl-2 transfectant plasmacytoma cells using polyethylene glycol (PEG, MW: 1450 KD). After fusion, the cells were resuspended in HAT (hypoxanthine, arninopterin, thymidine) medium supplemented with 10% fetal bovine serum (FBS) and distributed to 96 well plates at a density of 200 microliters per well for establishment of hybridoma cells. At day 6 post-fusion, 100 microliters of medium was aspirated and replaced with 100 microliters of fresh medium.

Example 2A

Anti-VEGFR-I Antibodies from Example 1 Bind to VEGFR-I and Inhibit VEGFR-I Binding to its Ligands a. VEGFR-I Binding and Blocking Assays At day 10-12 post-fusion, the hybridomas were screened for antibody production and specific binding activity of culture supernatant with rhuVEGFR-1 protein in ELISA-based binding and blocking assays. The positive hybridomas were subcloned three times by a limiting dilution culture for establishment of monoclonal hybridomas.

Specifically, hybridoma supernatants or purified antibodies were diluted in PBS with 5% FBS and 0.05% Tween 20 (ELISA buffer) and incubated in rhuVEGFR-I AP or AP coated 96-well microtiter plates for 30 minutes. Plates were washed with the ELISA buffer and incubated with goat anti-mouse IgG-horseradish peroxidase (HRP) conjugate (BioSource International, Camarillo, Calif.) for 30 minutes. TMB (3,3',5,5'-tetra-methylbenzidine) substrate (Kierkegaard and Perry Lab, Inc., Gaithersburg, Md.) was used for color development following the manufacturer's instruction. The absorbance at 450 nanometers (nm) was read for quantification of binding activity of antibodies. For identification of the hybridomas producing anti-VEGFR-I antibodies, hybridoma supernatants were preincubated with VEGFR-I AP for 1 hour. The mixtures were incubated with the ELISA buffer in VEGF or PlGF coated 96-well microtiter plates for 1 hour. PNPP (p-nitrophenyl phosphate) substrate for AP was used for color development following the manufacturer's instruction. The absorbance at 405 nm was read for quantification of VEGFR-I binding to VEGF or PlGF. Optical density (OD) values were read on a microtiter plate reader (Molecular Devices Corp., Sunnyvale, Calif.). ED50 and IC50 of the antibodies were analyzed using GraphPad Prism 3 software (GraphPad Software, Inc., San Diego, Calif.).

Figure 4:
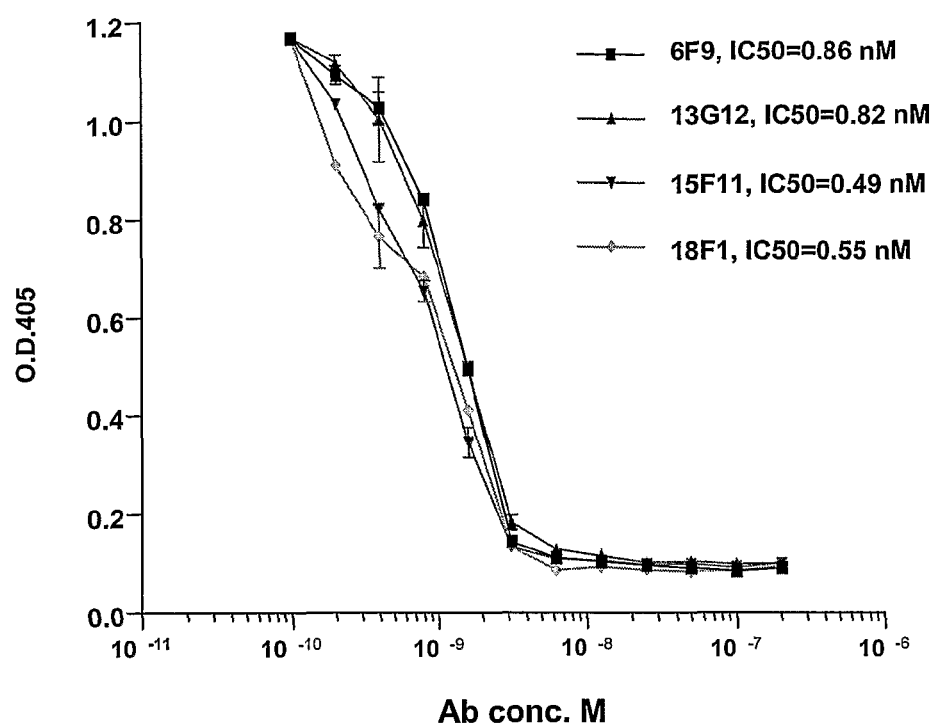
FIG. 4 is a chart depicting the results of an ELISA-based blocking assay measuring in vitro competition of embodiments of anti-VEGFR-I antibodies of the present invention with P1GF for VEGFR-I binding.
Figure 5:
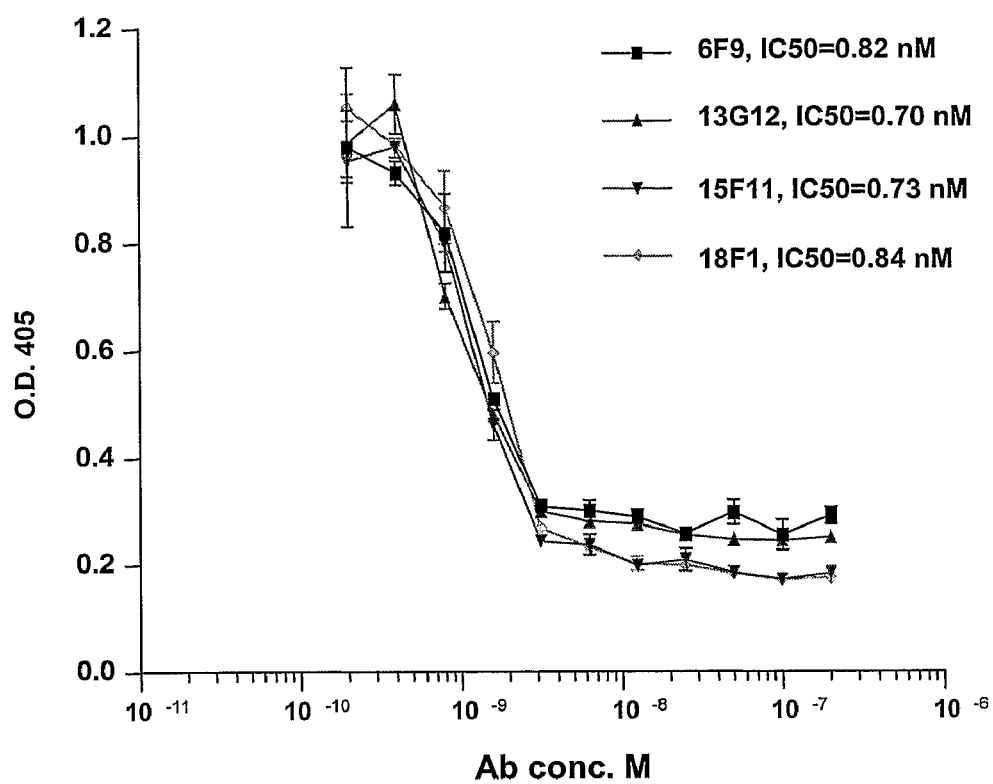
FIG. 5 is a chart depicting the results of an ELISA-based blocking assay measuring in vitro competition of embodiments of anti-VEGFR-I antibodies of the present invention with VEGF for VEGFR-I binding.

FIG. 3 shows the binding activity of purified antibodies produced from hybridomas designated "6F9," "13G12," "15F11," and "18F1." These antibodies exhibited a binding activity with ED50 of 0.1-0.3 nM in ELISA-based binding assay. FIGS. 4 and 5 show respectively that clones 6F9, 13G12, 15F11, 18F1 effectively blocked PlGF binding to VEGFR-I with IC50 of 0.4-0.8 nM and VEGF binding to VEGFR-I with IC50 of 0.7-0.8 nM. The binding and blocking characteristics of the antibodies are summarized in Table 4.

TABLE 4

Binding and Blocking Characteristics of anti-VEGFR-1 antibodies

| Clone | Binding Activity (ED50) | Blocking Activity (IC50) |
|---|---|---|
| 6F9 | 0.1 nM | 0.86 nM: PlGF |
|  |  | 0.82 nM: VEGF |
| 13G12 | 0.3 nM | 0.82 nM: PlGF |
|  |  | 0.70 nM: VEGF |

TABLE 4-continued

Binding and Blocking Characteristics of anti-VEGFR-1 antibodies

| Clone | Binding Activity (ED50) | Blocking Activity (IC50) |
|---|---|---|
| 15F11 | 0.3 nM | 0.49 nM: PlGF |
|  |  | 0.73 nM: VEGF |
| 18F1 | 0.1 nM | 0.55 nM: PlGF |
|  |  | 0.84 nM: VEGF | b. Measurement of Affinity of Anti-VEGFR-1 Antibodies

Affinities of anti-VEGFR-1 antibody clones 6F9, 13 G12, 15F11, 18F1 were determined by plasmon resonance technology using BIAcore 2000 (Pharmacia, Piscataway, N.J.) according to the procedures provided by the manufacturer. Kinetic analyses of the antibodies were performed by immobilization of recombinant extracellular domain of VEGFR-I onto a sensor surface at a low density. The ($k_{on}$) and dissociation ($k_{off}$) rates were determined using the BIAevaluation 2.1 software provided by the manufacturer.

Anti-VEGFR-1 antibody clones 6F9, 13G12, Fl1, and 18F1 exhibited a high affinity with a $K_D$ value of 69, 121, 70, and 54 pM, respectively. The kinetics of the antibodies are summarized in Table 5.

TABLE 5

Kinetics of human anti-VEGFR-1 antibodies

| Clone | $K_{on}$ | $K_{off}$ | $K_D$ |
|---|---|---|---|
| 6F9 | 1.01e6 M | 7.38e−5 M | 69 pM |
| 13G12 | 0.95e6 M | 10.9e−5 M | 121 pM |
| 15F11 | 1.02e6 M | 7.16e−5 M | 70 pM |
| 18F1 | 0.81e6 M | 4.27e−5 M | 54 pM | c. Evaluation of Specificity Anti-VEGFR-1 Antibody

To determine the specificity of an anti-VEGFR-1 monoclonal antibody to human VEGFR-I, purified antibodies 18F1 were tested in an ELISA-based assay. One µg/ml of recombinant human VEGFR-I Fc, mouse VEGFR-I Fc, mouse VEGFR-2 Fc, or human VEGFR-2 alkaline phosphatase was coated with PBS in a 96-well microtiter plates at 4° C. over night. After wash, the receptor coated plates were blocked with PBS containing 5% Dry Milk and 0.05% Tween 20. Serial dilutions of primary antibody 18F1 to human VEGFR-I, MF1 to mouse VEGFR-I, IC11 to human VEGFR-2, or DC1O1 to mouse VEGFR-2 were incubated in the receptor-coated plates for 30 minutes. After wash secondary anti-primary HRP conjugate antibodies was incubated in the plates for 30 minutes. Plates were washed and incubated with the substrate TMB (3,3',5,5'-tetra-methylbenzidine) for color development. The absorbance at 450 nm was read as OD values for quantification of binding activity of antibodies. Data were analyzed using a GraphPad Prism Software.

FIGS. 6A-D show the specificity of monoclonal antibody 18F1 to human VEGFR-I (FIG. 6A), and that the antibody has no cross reactivity with mouse VEGFR-I (FIG. 6B), human VEGFR-2 (FIG. 6C) and mouse VEGFR-2 (FIG. 6D). The results indicate that the anti-human VEGFR-I antibody 18F1 has a strict binding specificity with its respective receptor.

d. Western Blot

Confluent porcine aorta endothelial VEGFR-I expressing (PAE-VEGFR-I) cells and BT474 human breast carcinoma cells were cultured in serum-depleted F12 medium for 48 hours. The cells were then preincubated with anti-VEGFR-I antibody clone 18F1 at concentrations ranging from 0.1 to 30 µg/ml for 1 hour followed by stimulating with VEGF or P1GF for 5 minutes at 37° C. The cells were then rinsed with ice-cold PBS and lysed in lysis buffer (50 mM HEPES, 150 mM NaCl, 1% Triton X-100, and 10% glycerol containing 1 mM phenylmethylsulfonyl fluoride, 10 µg/ml aprotinin, 10 µg/ml leupeptin, and 1 mM sodium vanadate). Cell lysates were subjected to SDS-PAGE and transferred onto Immobilon membranes (Millipore Corp. Billerica, Mass.). After transfer, blots were incubated with the blocking solution and probed with antiphosphotyrosine antibody (PY20, Santa Cruz Biotechnology, Santa Cruz, Calif.) followed by washing. The protein contents were visualized using horseradish peroxidase-conjugated secondary antibodies followed by enhanced chemiluminescence (Amersham Pharmacia Biotech, Piscataway, N.J.). An anti-VEGFR-I specific antibody (Oncogene Research Products, San Diego, Calif.) was used for re-blot of VEGFR-I.

All anti-VEGFR-1 antibodies recognized a 180 KD molecule of VEGFR-I recombinant protein.

Example 2B

Anti-Human Anti-VEGFR-1 Antibody is Specific for Human VEGFR-I

HuVEGFR-I-Fc, mouse VEGFR-I-AP (hnClone Systems) or huVEGFR-2-AP (ImClone Systems) (100 ng/well) was coated on 96 strip-well plates and blocked with 5% milk/PBS. The binding of 18F1 and other anti-human VEGFR-I antibodies or a rat anti-mouse VEGFR-I antibody, MF1 (ImClone Systems, ref. 18), to plate bound VEGFR-I or VEGFR-2 was evaluated as described for the hybridoma supernatant screening above, except that bound antibody was detected with a goat anti-human kappa-HRP antibody (BioSource International, Camarillo, Calif.) for 18F1 and anti-human VEGFR-2 antibody IC11, or a goat anti-rat IgG-HRP antibody (BioSource International) for MF1.

8F1 showed a specific reactivity with human VEGFR-I (FIG. 32A) but no cross reactivity with mouse VEGFR-I (FIG. 32B) and human VEGFR-2 (FIG. 32C). The anti-mouse VEGFR-I blocking antibody MF1 was also demonstrated to be species specific, binding mouse (FIG. 32B). but not human VEGFR-I (FIG. 32A).

Example 3

Anti-VEGFR-I Antibodies Bind to Native VEGFR-I on VEGFR-I Expressing Cells a. Flow Cytometry Analysis Aliquots of $10^6$ PAE-VEGFR-I cells were harvested from subconfluent cultures and incubated with anti-VEGFR-I antibody clones 6F9, 13G12, Fl1, and 18F1 in PBS with 1% bovine serum albumin (BSA) and 0.02% sodium azide (staining buffer) for one hour on ice. Aliquots of $10^6$ DU4475 human breast carcinoma cells were harvested from subconfluent cultures and incubated with anti-VEGFR-1 antibody clone 18F1 in PBS with 1% bovine serum albumin (BSA) and 0.02% sodium azide (staining buffer) for one hour on ice. A matched IgG isotype (Jackson ImmunoResearch, West Grove, Pa.) was used as a negative control. Cells were washed twice with flow buffer and then incubated with a fluorescein isothiocyanate (FITC)-labeled goat anti-human IgG antibody (BioSource International, Camarillo, Calif.) in staining buffer for 30 minutes on ice. Cells were washed as above and analyzed on an Epics XL flow cytometer (Beckman-Coulter, Hialeah, Fla.). Dead cells and debris were eliminated from the analysis on the basis of forward and sideways light scatter. The mean fluorescent intensity units (MFRJ) were calculated as the mean log fluorescence multiplied by the percentage of positive population.

Figures 7, 7A, 7B, 7C, 7D, 7E:
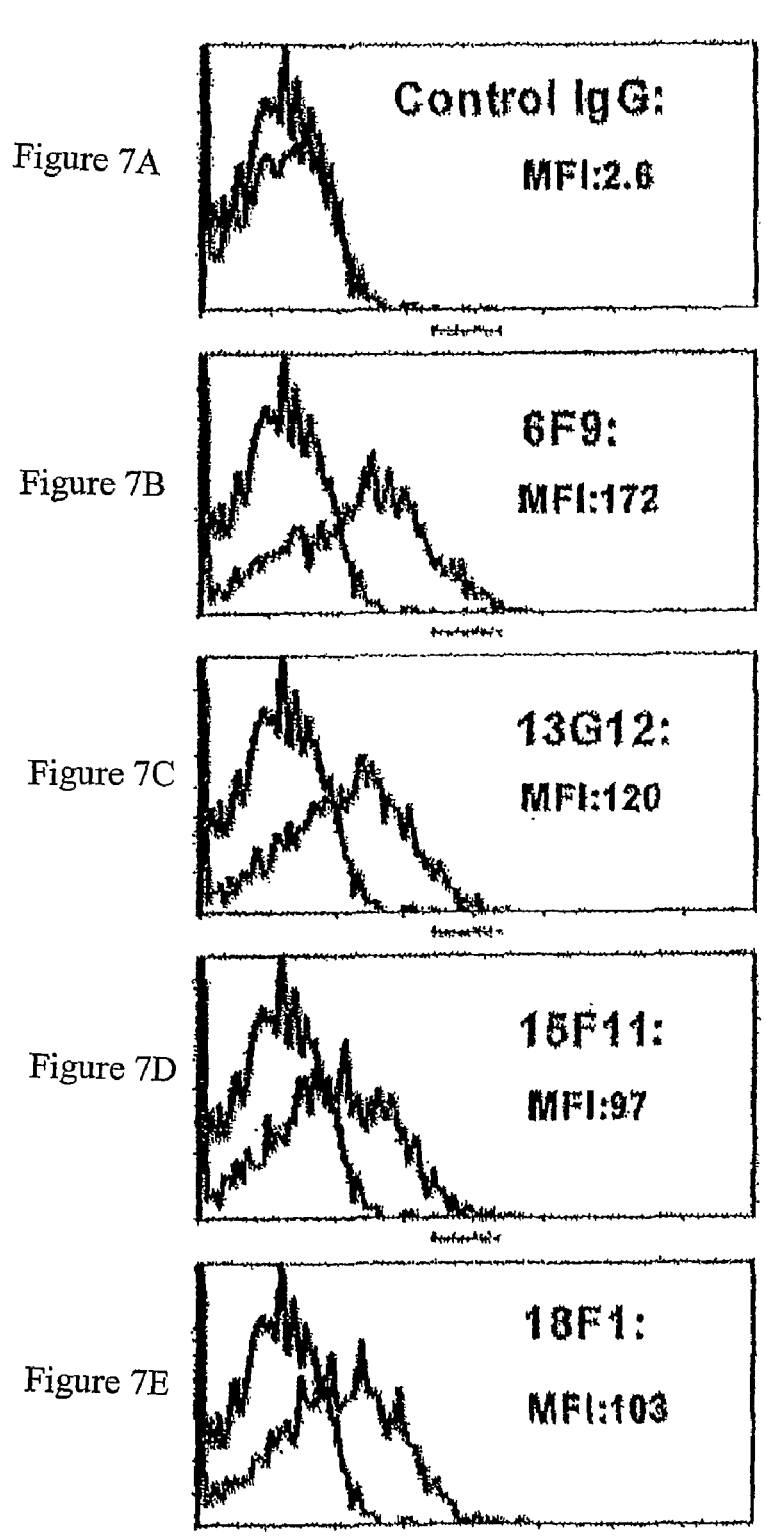
FIG. 7A-E are results of flow cytometry analysis showing binding reactivity of embodiments of anti-VEGFR-I antibodies of the present invention with VEGFR-I expressing porcine aorta endothelial cells.

FIG. 7 shows binding reactivity of clones 6F9, 13G12, 15F11 and 18F1 with the PAE-VEGFR-I expressing cells. FIGS. 8A and 8B show binding reactivity of clone 18F1 with PAE-VEGFR-I expressing cells and DU4475 human breast carcinoma, respectively. These results indicate that the human anti-VEGFR-1 antibodies bind to native VEGFR-I expressed in cell surface.

b. Surface VEGFR-I Blocking Assay

The binding of $^{125}$I-VEGF to VEGFR-I on cell surface was performed using PAE-VEGFR-I expressing cells. Cells were grown on non-coated plastic cell culture plates, which were found to decrease nonspecific binding without affecting the specific binding of $^{125}$I-VEGF. Confluent cells were incubated in serum- and growth supplement-free Dulbecco's Modified Eagle Medium (DMEM)ZF-12 medium (Invitrogen, Carlsbad, Calif.) for 24 hours. Cells were rinsed once with ice-cold DMEMZF-12 medium containing 0.025 M HEPES and 1 mgZml bovine serum albumin (BSA). A serial dilution of anti-VEGFR-I antibody 18F1 or cold VEGF at the concentration of a 200-fold molar excess of labeled VEGF was added to each well in the plate and incubated at 4° C. for 1 hour. After wash, $^{125}$I-VEGF was added at the concentration of 2 ngZml and was incubated at 4° C. for 2 hours on a platform shaker. The cells were washed three times with PBS containing 1 mgZml BSA and 0.25 mM $CaCl_2$, and were incubated for 5 minutes in the presence of 1% Triton X-100, 1 mgZml BSA, and 0.16% $NaN_3$ to remove bound VEGF. The soluble content of each well was counted in a gamma counter. The assays were performed in triplicate in at least three independent experiments and the data were analyzed using Prism GraphPad software 3.03.

Figure 9:
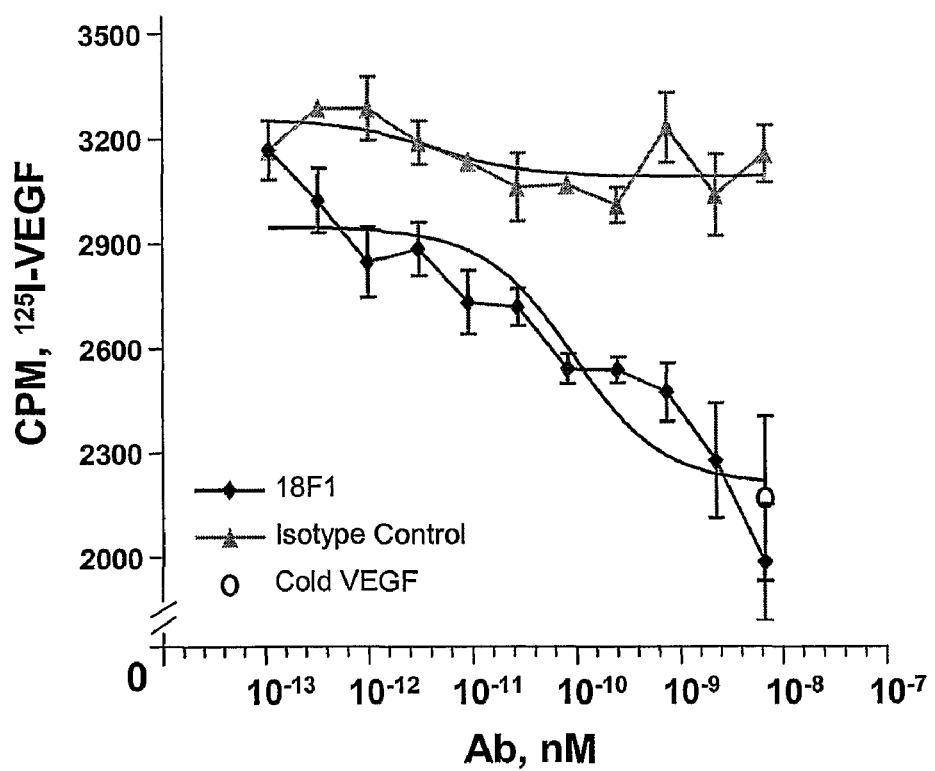
FIG. 9 is a chart depicting results of a cell-based blocking assay measuring in vitro competition of anti-VEGFR-1 antibody 18F1 of the present invention with VEGF binding to VEGFR-I on endothelial cells.

FIG. 9 shows the strong blocking activity of the anti-VEGFR-I antibody 18F1 that dramatically prevents the native VEGFR-I from binding to the $^{125}$I-VEGF on the porcine aorta endothelial cells.

Example 4

Anti-VEGFR-I Antibodies Inhibit Autophosphorylation of VEGFR-I and Activation of MAPK and Akt in Response to VEGF and PlGF a. VEGFR-I Phosphorylation Assay Autophosphorylation of the VEGFR-I induced by its ligands and resulting activation of a classical MAPK, extracellular signal-regulated protein kinases 1Z2 (ERK1Z2) and the PBK/Atk downstrean signaling pathways mediate cellular biological responses such as proliferation, motility, survival, and differentiation. The ability of an anti-VEGFR-1 antibody to inhibit phosphorylation of VEGFR-I and activation of ERK1 Z2 and the Akt kinases downstream signaling were determined by using the PAE-VEGFR-I transfectant and BT474 breast carcinoma cells.

PAE-VEGFR-I and BT474 cells were seeded at a density of $5\times10^5$/well in 100 or 150 $mm^2$ plates and cultured in serum-free medium for 18-48 hours. After replacing the culture medium, the cells were treated at 37° C. with anti-VEGFR-I antibody clones 6F9, 15F11, and 18F1 or isotype control for 1 hour and then incubated with 50 ng/ml of VEGF or 100 ng/ml of PlGF for 10 minutes. After treatments, total cell protein extracts were isolated with lysis buffer [20 mM HEPES (pH 7.4), 10 mM $MgCl_2$, 2 mM, $MnCl_2$, 0.05% Triton X-100, and 1 mM DTT], and immunoprecipitated with anti-VEGFR-I antibody (C-17, Santa Cruz Biotechnology, Santa Cruz, Calif.). Western blot of phosphorylated VEGFR-I was detected using anti-phospho-kinase antibody (PY-20, Santa Cruz Biotechnology, Santa Cruz, Calif.). Proteins were detected using and electrogenerated chemiluminescence system (ECL)(Amersham Pharmacia Biotech, Piscataway, N.J.), and quantified by densitometry using NIH Image (National Institute of Mental Health, Bethesda, Md.).

b. In vitro Kinase Assay

For evaluation of MAPK and Akt phosphorylation, BT474 cells were seeded at a density of $5\times10^5$/well in 12 well plates in serum-free conditions for 18 hours. Cells were treated at 37° C. with anti-VEGFR-1 antibody clone 18F1 or isotype control for 1 hour and then incubated with 50 ng/ml of VEGF or 100 ng/ml of PlGF for 5-10 minutes. Cell lysis, protein isolation and electroblotting were performed. Membranes were incubated with antibodies against phosphorylated p44/p42 MAP kinases (Thr202/Tyr204, Santa Cruz Biotechnology, Santa Cruz, Calif.) or phosphorylated Akt (Ser473, Cell Signaling Technology, Beverly, Mass.), at a concentration of 1 µg/ml, followed by incubation with a secondary IgG-HRP (1:5000). To ensure equal loading of samples, membranes were stripped and reprobed with anti-p44/p42 (Santa Cruz Biotechnology, Santa Cruz, Calif.) or anti-Akt antibodies (Cell Signaling Technology, Beverly, Mass.).

c. Results

Figure 10:
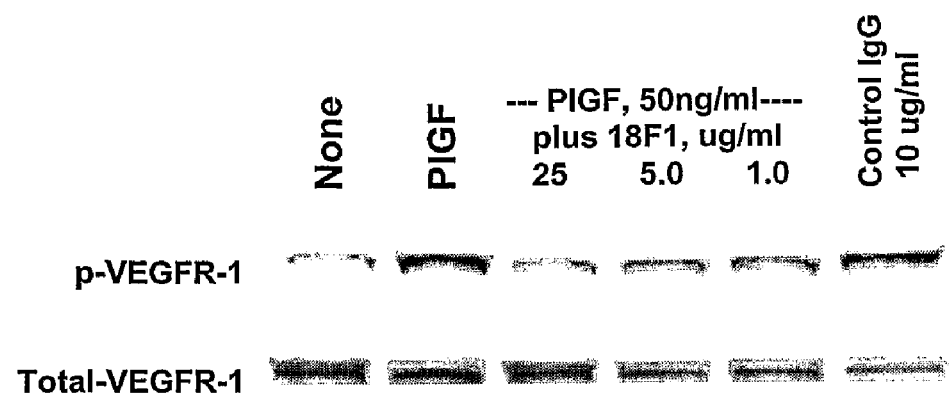
FIG. 10 is a Western blot analysis demonstrating the reduction of P1GF-stimulated phosphorylation of VEGFR-I by treatment with anti-VEGFR-I antibody 18F1 of the present invention in porcine aorta endothelial VEGFR-I expressing cells.
Figure 11:
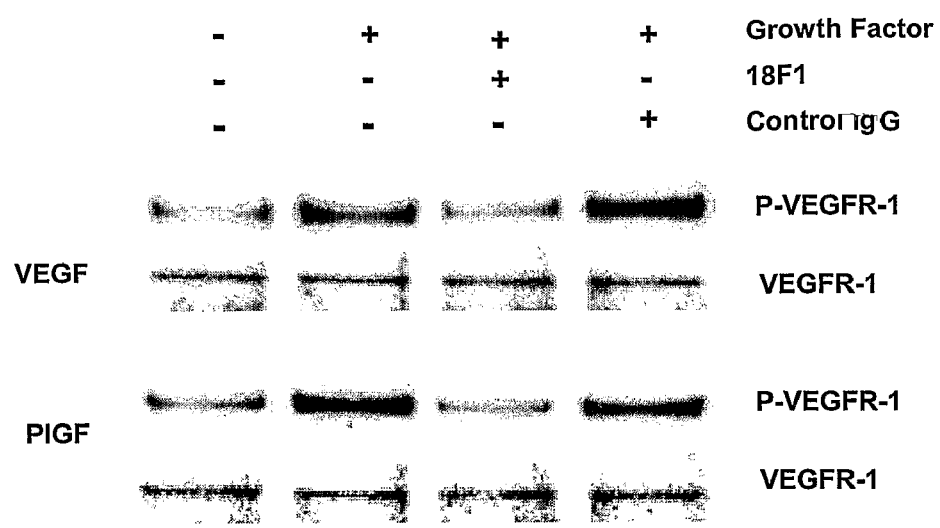
FIG. 11 is a Western blot analysis demonstrating inhibition of P1GF or VEGF-stimulated phosphorylation of VEGFR-I by treatment with anti-VEGFR-I antibody 18F1 of the present invention in BT474 breast cancer cells.
Figure 12:
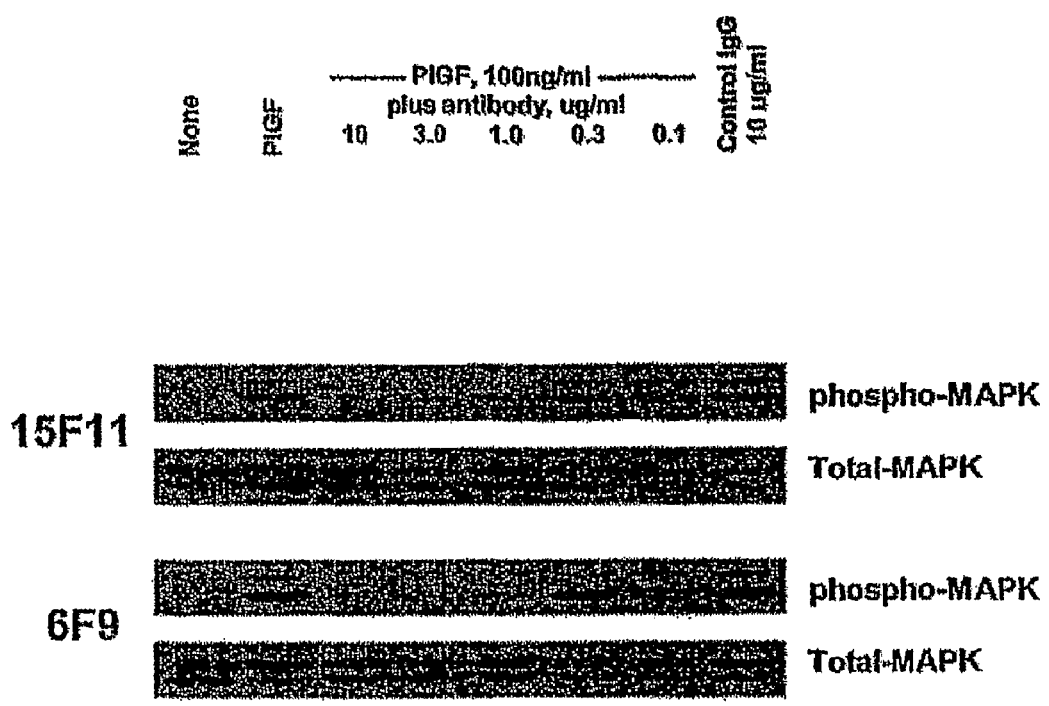
FIG. 12 is a Western blot analysis demonstrating inhibition of P1GF induced activation of ERK1/2 downstream signaling by embodiments of anti-VEGFR-1 antibodies of the present invention in porcine aorta endothelial VEGFR-I expressing cells.
Figure 13:
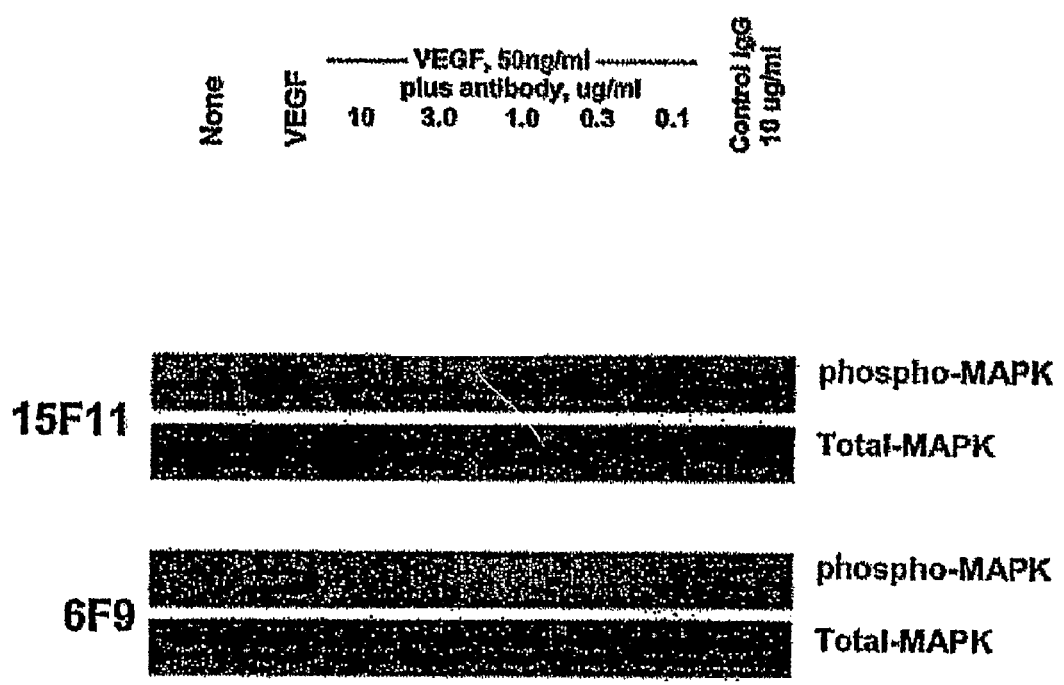
FIG. 13 is a Western blot analysis demonstrating the inhibition of VEGF induced activation of ERK1/2 downstream signaling by embodiments of anti-VEGFR-1 antibodies of the present invention in porcine aorta endothelial VEGFR-I expressing cells.

As shown in FIGS. 10-14 a significant phosphorylation of VEGFR-I and activation of ERK1/2 and Akt signaling in the PAE-VEGFR-I transfectant and BT474 breast cancer cells was induced by VEGF and PlGF stimulation, suggesting the intrinsic activity of the VEGFR-I and the receptor-associated downstream kinase signaling pathways in both breast cancer and endothelial cells. As shown in FIGS. 10 and 11, respectively, treatment with anti-VEGFR-1 antibody 18F1 significantly reduced PlGF or VEGF-stimulated phosphorylation of VEGFR-I compared to untreated control in PAE-VEGFR-I transfectant and BT474 breast cancer cells. As shown in FIGS. 12 and 13 respectively, treatment with anti-VEGFR-I antibodies 15F11 and 6F9 also dramatically inhibited PlGF and VEGF induced activation of ERK1/2 downstream signaling induced by PlGF and VEGF in PAE-VEGFR-I transfectant cells. Activation of Akt protein kinase is an important intracellular signaling event mediating cell survival in breast cancer. As shown in FIGS. 14A and B, respectively, treatment with anti-VEGFR-I antibody 18F1 dramatically inhibited PlGF or VEGF-induced activation of ERK $^1$A downstream signaling induced by PlGF and VEGF in PAE-VEGFR-I transfectant cells.

Figure 15:
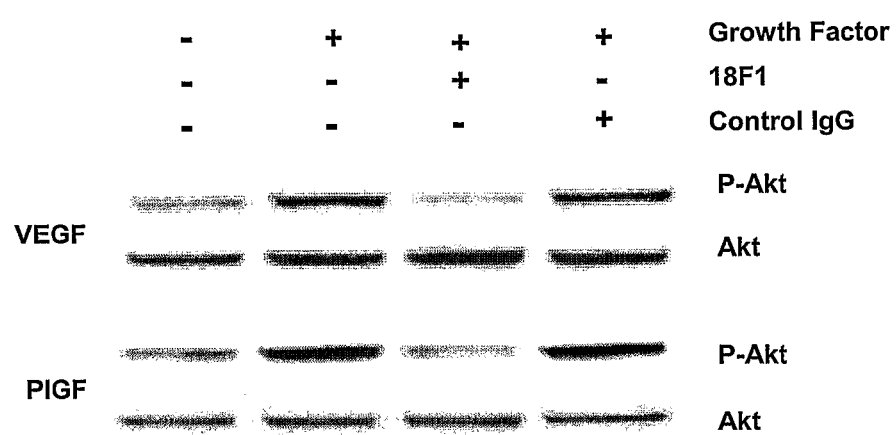
FIG. 15 is a Western blot analysis demonstrating that the anti-VEGFR-I antibody 18F1 of the present invention blocked P1GF or VEGF-stimulated phosphorylation of Akt in BT474 breast cancer cells.

As shown in FIG. 15, the anti-VEGFR-I antibody 18F1 significantly blocked PlGF-stimulated phosphorylation of Akt in BT474 breast cancer cells. These results demonstrated that treatment with the anti-VEGFR-I antibodies is effective to inhibit activation of the VEGFR-I and downstream signaling kinase pathways in both breast cancer and endothelial cells.

Example 5

Anti-VEGFR-I Antibodies Blocks In Vitro Growth of Breast Tumor Cells

Tumor hypoxia is associated with enhancement of malignant progression, increase of aggressiveness and chemotherapeutic drug resistance. Hypoxic tumor cells undergo biological responses that activate signaling pathways for survival and proliferation by upregulation of a variety of gene expression including the VEGFR-I (Harris A L. Nat Rev Cancer. 2:38-47, 2002).

Cell Growth Assay

DU4475 carcinoma cells were seeded at a density of $5 \times 10^3$/well into 96-well plates in serum-free conditions for 18 hours, and in some case followed by treatment with 100 nM of desferoxamine for additional 5 hours. Inhibitory effect of anti-VEGFR-I antibody on tumor cell growth was determined by incubation of cells with anti-VEGFR-I antibody clones 6F9, 13G12, 15F11, and 18F1 at doses of 3, 10, and 30 µg/ml in the presence of 50 ng/ml of VEGF or 200 ng/ml of P1GF for 48 hours. Viable cells were then counted in triplicate using a Coulter cytometer (Coulter Electronics Ltd. Luton, Beds, England). Each experiment was done in triplicate.

Figure 16:
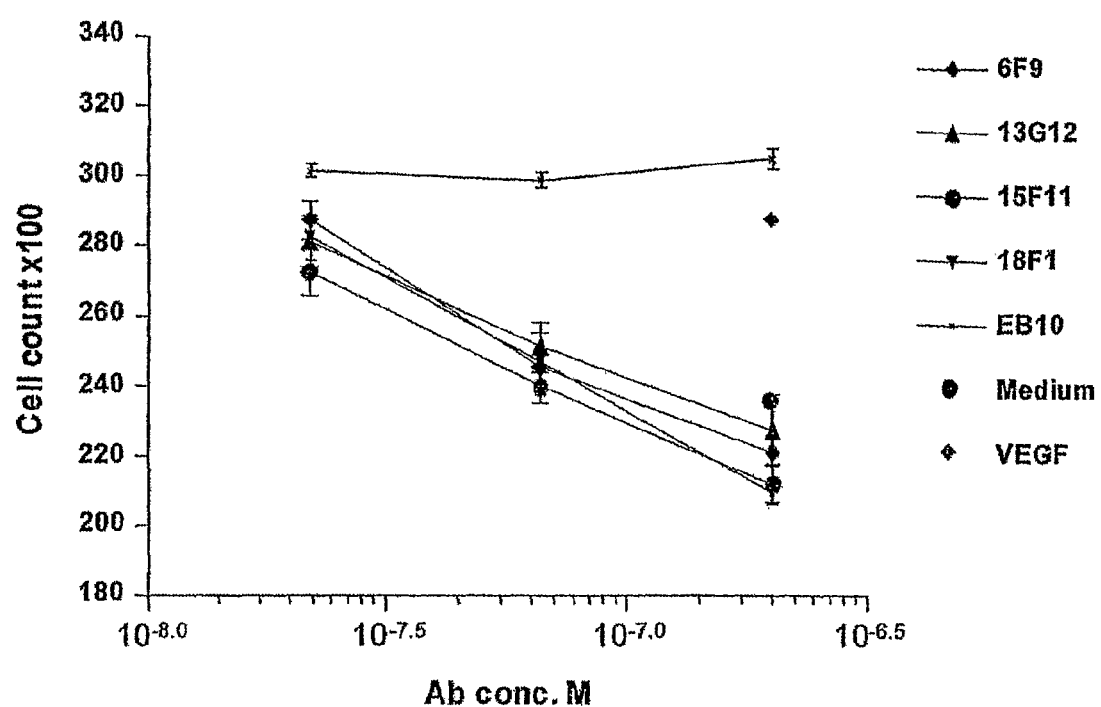
FIG. 16 is a dose response curve showing the inhibition of VEGF stimulated cell proliferation in DU4475 breast carcinoma cells treated with embodiments of anti-VEGFR-I antibodies of the present invention in a dose response manner.
Figure 17:
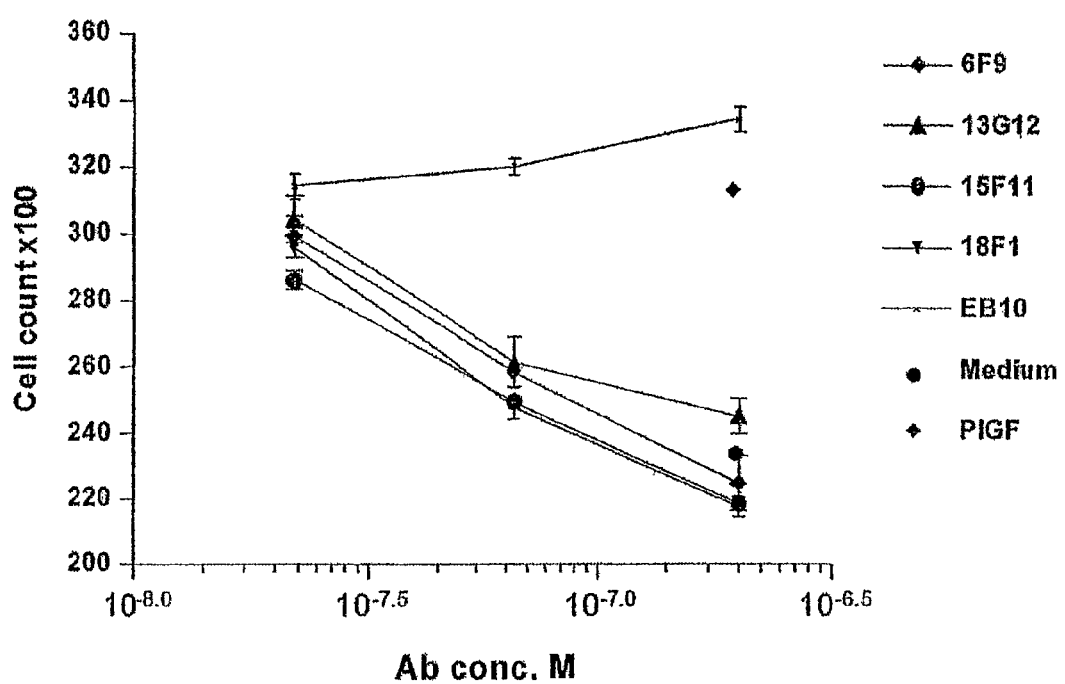
FIG. 17 is a dose response curve showing the inhibition of P1GF stimulated cell proliferation in DU4475 breast carcinoma cells treated with embodiments of anti-VEGFR-I antibodies of the present invention in a dose response manner.

The growth rate of the hypoxia-mimic agent desferoxamine pre-treated DU4475 tumor cells was increased by approximately 2 fold in response to either VEGF or P1GF stimulation. As shown in FIGS. 16 and 17, respectively, treatment with the anti-VEGFR-I antibodies effectively reduced VEGF and PIGF stimulated proliferation of DU4475 breast carcinoma cells in a dose response manner. FIGS. 18A and B separately plots the antibody concentration of antibody clone 18F1 versus cell count of VEGF and PIGF stimulated proliferation of DU4475 breast carcinoma cells. The inhibition of PIGF-induced DU4475 cell growth in vitro by the anti-VEGFR-I antibodies as represented in IC50 values is summarized in Table 6.

TABLE 6

Inhibition of PIGF-induced DU4475 cell growth in vitro

| Clone | in vitro cell growth |
|---|---|
| 6F9 | IC50: 43 nM |
| 13G12 | IC50: 66 nM |
| 15F11 | IC50: 44 nM |
| 18F1 | IC50: 24 [nM] |

Example 6A

Anti-VEGFR-I Antibodies Suppress Growth of Breast Tumor Xenografts

Treatment of Human Breast Carcinoma Xenografts

Antitumor efficacy of the human anti-VEGFR-I antibodies was tested in the human xenograft breast tumor models.

Athymic nude mice (Charles River Laboratories, Wilmington, Mass.) were injected subcutaneously in the left flank area with $2 \times 10^6$ of DU4475 cells or $5 \times 10^6$ of MDA-MB-231 and MDA-MB-435 cells mixed in Matrigel (Collaborative Research Biochemicals, Bedford, Mass.). In the DU4475 and MDA-MB-231 models, tumors were allowed to reach approximately 200 mm³ in size and then mice were randomized into groups of 12-16 animals per group. Animals received i.p. administration of the anti-VEGFR-I antibody clones 6F9, 15F11, or 18F1 at a dose of 0.5 mg (MDA-MB-231) or 1 mg (DU4475) three times each week In the MDA-MB-435 model, the tumor cells were implanted subcutaneously into mammary fat pad area in the mouse. After tumors grew to reach approximately 200 mm³ in size, mice were randomized into groups of 15 animals per group and intraperitoneally administered with 0.5 mg per dose of 18F1 antibody three times each week. Mice in control groups received an equal volume of saline solution. Treatment of animals was continued for the duration of the experiment. Tumors were measured twice each week with calipers. Tumor volumes were calculated using the formula [τr/6 (w1×w2×w2)], where "w1" represents the largest tumor diameter and "w2" represents the smallest tumor diameter.

Figure 19A:
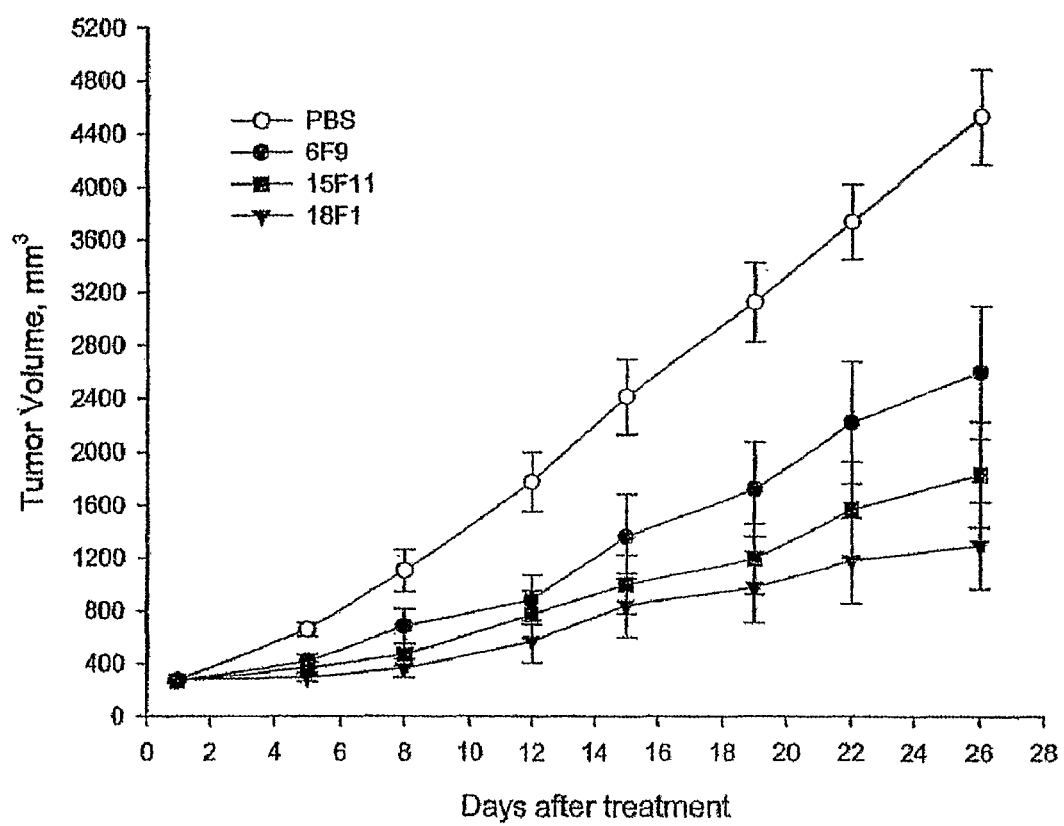
FIGS. 19A and 19B are charts plotting tumor growth of DU4475 breast tumors versus days after treatment with embodiments of anti-VEGFR-I antibodies of the present invention.
Figure 19B:
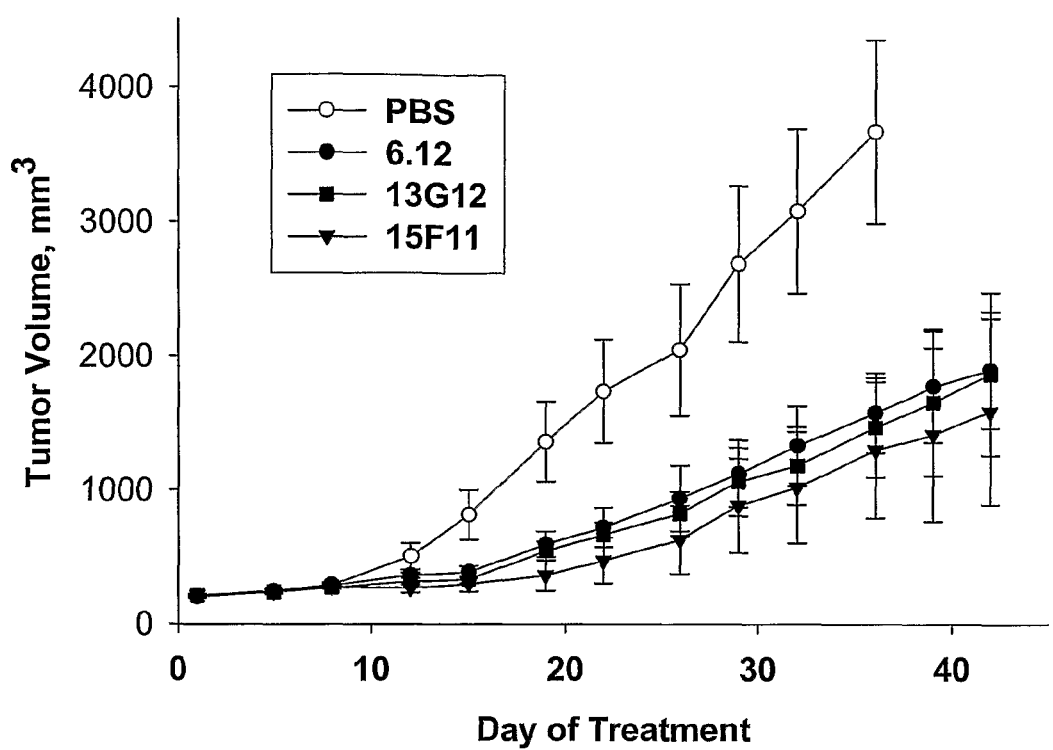

As shown in FIGS. 19A and 19B$_5$ systemic administration of anti-VEGFR-I antibodies 6F9, 15F11, 13G12 and 18F1 at a dose of 1 mg per dose three times each week led to a statistically significant suppression of tumor growth of the DU4475 xenograft (p<0.05). As shown in FIGS. 20A, B, and C respectively, systemic administration of anti-VEGFR-I antibody 18F1 at a dose of 0.5 or 1 mg per dose three times each week led to a statistically significant suppression of tumor growth of the DU4475, MDA-MB-231, MDA-MB-435 xenografts (ANOVA p<0.05). As shown in FIGS. 21A and B, treatment with antibody clone 18F1 against human VEGFR-I for inhibiting cancer cell growth and clone MF1 against mouse VEGFR-I for inhibiting tumor angiogenesis at a dose of 20 or 40 mg/kg twice each week resulted in a stronger inhibition of tumor growth in the DU4475 and MDA-MB-231 xenograft models (P<0.05) when compared to either antibody alone. These results demonstrate that blockade of the in vivo function of VEGFR-I in directly promoting cancer cell growth and modulating tumor vascularization by the anti-VEGFR-I antibody is effective to suppress growth of VEGFR-I positive breast tumors in xenograft models.

Example 6B

Anti-Human Anti-VEGFR-I Antibody Blocks In Vitro Growth of Breast Cancer Cells

DU4475 carcinoma cells ($2 \times 10^4$ per well) were seeded into 24-well plates in serum-free conditions for 18 hours and then treated with hypoxia-mimic agent desferrioxamine (Sigma) for an additional 6 hours. A serial dilution of anti-human VEGFR-I antibody 18F1 was added to the plates in triplicate and incubated in the presence of 50 ng/niL of VEGF-A (R&D Systems) or 200 ng/mL of P1GF for 48 hours. Total cell number (bound and in suspension) was determined for each well using a Coulter cell counter (Coulter Electronics Ltd., England).

Treatment of IMC-18F1 significantly blocked VEGF-A and P1GF stimulated proliferation of DU4475 breast carcinoma cells (FIGS. 31A and 31B, respectively; estimated IC50:30-50 nM). The isotype control antibody had no effect on cell proliferation. Thus, 18F1 inhibited VEGFR-I ligand induced promotion of tumor cell proliferation/survival.

Example 7

Anti-VEGFR-I Antibody Inhibits VEGF-A and VEGF-B Stimulated Colony Formation of Colon Cancer Cells One mL DMEM medium containing 10% FBS and 1% agarose (Cambrex Corporation, East Rutherford, N.J.) was plated in each well of six well plates. HT-29 human colon carcinoma cells in serum free medium were treated with 66 nM 18F1 or control IgG for 1 hour and followed by treatment with 10 ng/mL VEGF-A or 50 ng/mL VEGF-B for additional 4 hours. The treated cells were mixed with 1 mL 10% FBS DMEM containing 0.5% agarose and the appropriate antibodies and/or ligands. One mL of this suspension, containing 250 cells, was plated in each well on top of the 1% agarose base layer. After 2 days, additional medium containing antibodies and/or ligands was added to the wells to keep the agarose hydrated. Cells were allowed to grow for 14 days at 37° C. Afterwards, colonies larger than 50 µm in diameter were counted using a dissecting microscope. Statistical analysis was performed using hiStat Statistical Software (V2.03, GraphPad Software, San Diego, Calif.)

Figure 22:
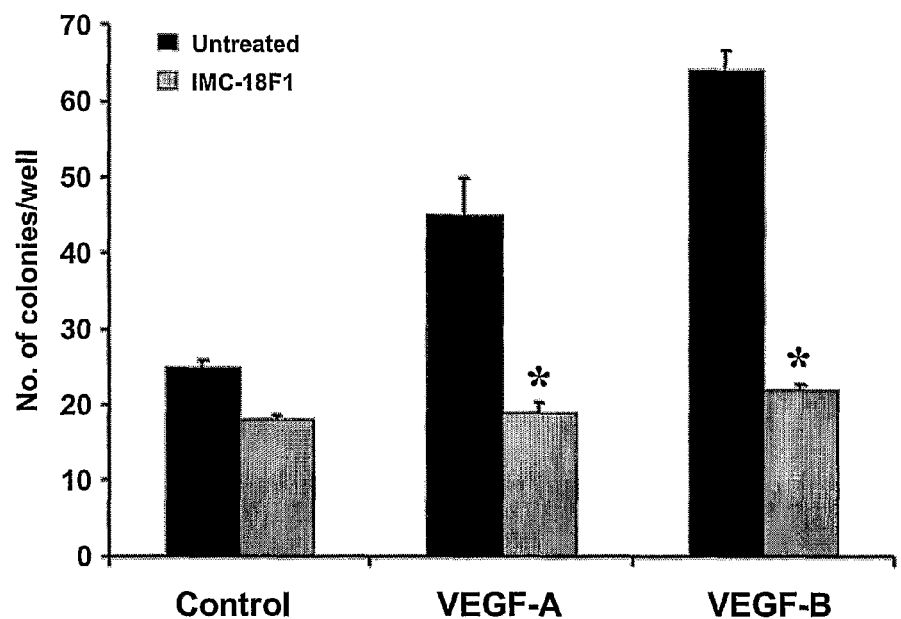
FIG. 22 is a chart of the number of colon cancer cell colonies present after treatment with anti-human VEGFR-I antibody 18F1 in the presence of VEGF-A and VEGF-B.

The number and size of colonies were significantly increased in the wells where cells were treated with VEGF-A or VEGF-B compared to untreated cells in complete medium only. As shown in FIG. 22, treatment with 18F1 completely suppressed ligand-induced colony formation compared to basal activity in the absence of stimulation with ligands ($p<0.03$) (FIG. 22). Thus, for both adherent and non-adherent cells, 18F1 has the capability of suppressing the survival and growth of tumor cells.

Example 8

Anti-VEGFR-I Antibody Inhibits VEGF-A and VEGF-B Induced Migration and Invasion of Colon Cancer Cells HT-29 cells ($2.5 \times 10^4$) or SW480 cells ($1.5 \times 10^4$) were incubated in medium containing 1% FBS with the anti-VEGFR-1 antibody 18F1 (66 nM) in the upper surface of a 24 well MATRIGEL™ coated (HT-29) or uncoated (SW480) 8.0-µm pore size membrane insert (Becton Dickinson Labware, Bedford, Mass.). The inserts were placed into lower chambers containing 10 ng/mL VEGF-A (R&D Systems) or 50 ng/mL VEGF-B (R&D Systems) for 48 hours. Cells remaining in the top chamber of the inserts were removed with a cotton swab. Cells migrating to the underside of the inserts were stained with Diff-Quik (Harleco, Gibbstown, N.J.) and counted in ten random fields at 100× magnification. Statistical analysis was performed using InStat Statistical Software (V2.03, GraphPad Software, San Diego, Calif.).

Figures 23, 23A, 23B:
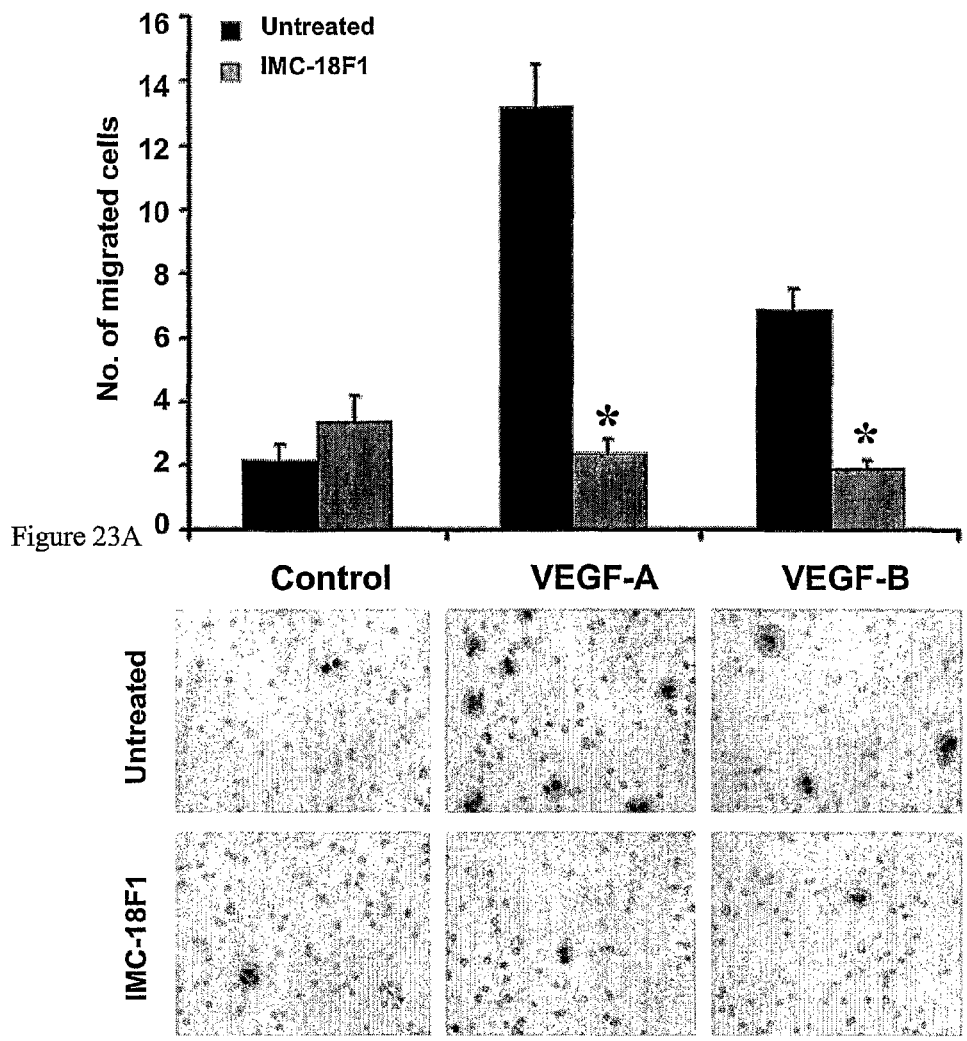
FIG. 23A is a chart of the number of migrated tumor cells after treatment with anti-human VEGFR-I antibody 18F1 in the presence of VEGF-A and VEGF-B.
FIG. 23B are photomicrographs of stained migrated cells after treatment with anti-human VEGFR-I antibody 18F1 in the presence of VEGF-A and VEGF-B.

As shown in FIGS. 23A and 23B, VEGF-A or VEGF-B induced migration of HT-29 cells towards ligand through an uncoated membrane. As shown in FIGS. 24A and 24B, these ligands also induced invasion of SW480 cells through a MATRIGEL™ coated membrane. 18F1 completely blocked VEGFR-I ligand induced migration and invasion compared to basal activity in the absence of stimulation with ligands ($p<0.05$, FIGS. 23 and 24). Thus, in addition to negative effects on tumor cell proliferation and survival, 18F1 may provide a means to inhibit the invasion and subsequent metastasis of tumor cells.

Example 9

Treatment with Anti-VEGFR-1 Specific Antibody Suppresses In Vivo Growth of VEGFR-I Expressing Human Xenograft Tumors Female athymic nu/nu mice, 6-8 weeks of age, were injected subcutaneously on the lateral dorsal surface with 0.4 mL volume of a suspension containing a human tumor cell line in media, diluted 1:1 with MATRIGEL™ (BD Biosciences). The cell lines used in xenograft models, with the cell doses indicated in parenthesis ($10^6$ cells/mouse), were: human colon carcinoma cell lines DLD-I (5), GEO (5) and HT-29 (5); human breast carcinoma cell lines DU4475 (2), MDA-MB-231 (5), MDA-MB-435 (5), and BT474 (5). When tumors reached approximately 200-300 mm³, mice were randomized by tumor size and divided into treatment groups. Tumor growth was evaluated approximately twice weekly, with tumor volume calculated as $\pi/6 \ast (\text{Length} \ast \text{Width}^2)$, where Length=longest diameter and Width=diameter perpendicular to Length. Tumor dimensions were measured with calipers. T/C % was calculated as 100*(Final Treatment Tumor Volume/Initial Treatment Tumor Volume)/(Final Control Tumor Volume/Initial Control Tumor Volume).

18F1 was diluted in 0.9% USP saline (Braun) or phosphate buffered saline (PBS) and administered intraperitoneally in a volume of 0.5 mL per mouse. The effect of treatment on tumor growth was analyzed using repeated measures analysis of variance (RM ANOVA), $p<0.05$ was considered significant.

As shown in FIG. 25, administration of intraperitoneal 18F1 significantly ($p<0.05$) suppressed the growth of DU4475 (FIG. 25A), MDA-MB-231, and MDA-MB-435 (FIG. 25B) xenograft tumors. As shown in FIG. 26, a significant antitumor effect of 18F1 monotherapy was also observed against HT-29 (FIG. 26A), DLD-I (FIG. 26B), and GEO (FIG. 26C) colon cancer xenografts. These results demonstrate that blockade of human VEGFR-I effectively suppresses the growth of xenograft tumors established with VEGFR-I expressing human tumor cell lines.

Example 10

Anti-Human VEGFR-I Treatment Inhibits In Vivo Signaling of Proliferation and Survival Pathways and Induced Tumor Cell Apoptosis Paraffin-embedded MDA-MB-231 xenografts were evaluated immunohistochemically for markers of tumor cell proliferation, survival, and apoptosis. Markers of proliferation and survival included Ki-67 (rabbit pAb; Lab Vision Corporation, Fremont, Calif.), phospho-specific p44/42 MAPK (Thr202/Tyr204) (rabbit pAb; Cell Signaling Technology) and phospho-specific Akt (Ser473) (rabbit pAb; Cell Signaling Technology). The EnVision+ System for rabbit antibodies (DAKO Cytomation, Carpenteria, Calif.) was used with 3,3' diaminobenzidine (DAB) as the chromagen, per kit instructions. After brief counterstaining in Mayer's hematoxylin all sections were dehydrated, cleared and coverslipped using a permanent mounting medium. Tumor apoptosis was assessed by TUNEL assay using ApopTag® Peroxidase In Situ Apoptosis Detection Kit (Chemicon, Temecula, Calif.) per kit instructions. Stained sections were coverslipped with Gelmount (Biomeda, Foster City, Calif.). Positive immunostaining and TUNEL positive immunofluorescence were analyzed and imaged using an Axioskop light microscope with an Axiocam digital camera (Carl Zeiss, Germany).

Figure 27:
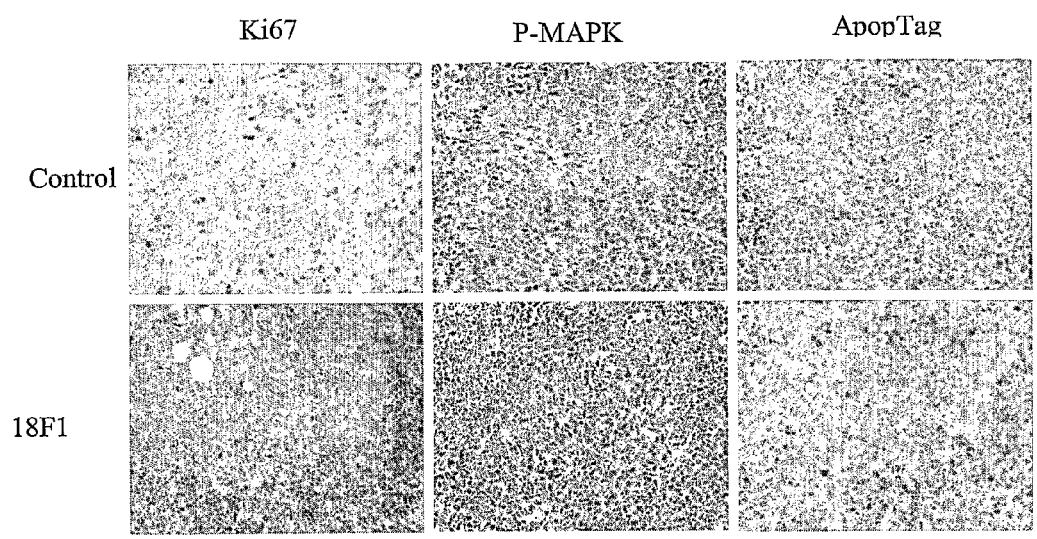
FIG. 27 are photomicrographs of MDS-MB-231 xenograft tumors after treatment with anti-human VEGFR-I antibody 18F1.

As shown in FIG. 27, a marker for proliferating cells (Ki-67) was significantly reduced after 14 days of treatment with 18F1 at 20 mg/kg (about 0.5 mg/dose with female nu/nu athymic mice), 2×/week (Study Number 3067-04). In addition, 18F1 treatment resulted in a marked decrease in the activation of MAPK at this time point (FIG. 27). An increase in apoptosis (FIG. 27) as measured by TUNEL positive events and a significant decrease in Akt phosphorylation were also detected in MDA-MB-231 xenograft tumors after 1 week of treatment with 18F1 (0.5 mg/dose, M-W-F).

Example 11

In Vivo Blockage of Both Human and Murine VEGFR-I Leads to Greater Antitumor Activity Against Human Breast Carcinoma Xenografts 18F1 was used in combination with an antibody to mouse VEGFR-I, MF1. 18F1 was diluted in 0.9% USP saline (Braun) or phosphate buffered saline (PBS) and administered intraperitoneally in a volume of 0.5 niL per mouse. The effect of treatment on tumor growth was analyzed using repeated measures analysis of variance (RM ANOVA), p<0.05 was considered significant As shown in FIG. 28, in both the MDA-MB-231 (FIG. 28A) and DU4475 (FIG. 28B) xenograft models, inhibition of tumor expressed human VEGFR-I with 18F1 and endogenous mouse VEGFR-I with MF1, resulted in significant tumor growth inhibition (p<0.05). MF1 has previously been shown to inhibit tumor growth through a reduction in tumor angiogenesis. The combination of 18F1 and MF1 resulted in significantly more tumor growth inhibition than the monotherapies (p<0.05). 18F1+MF1 combination therapy was not associated with body weight loss. These data support dual inhibition of tumor vascularization and tumor cell proliferation and survival with 18F1 treatment in patients.

Example 12

Anti-VEGFR-I Antibody in Combination with Chemotherapeutics

18F1+MF1 was combined with cytotoxic therapies, 5-flourouracil, leucovorin, and paclitaxel in the MDA-MB-231 model. 18F1 was diluted in 0.9% USP saline (Braun) or phosphate buffered saline (PBS). Antibody treatments administered at a constant dose per mouse were administered in a volume of 0.5 mL per mouse. Antibody and cytotoxic treatments administered at a dose proportional to body weight were given in a volume of 10 µL per gram body weight. 5-Fluorouracil and leucovorin (5-FU/LV) were diluted separately in USP saline and dosed separately. Paclitaxel was either made in 5% benzyl alcohol (Sigma), 5% Cremophor EL (Sigma), and 90% USP saline or in 5% ethyl alcohol (Sigma), 5% Cremophor EL, and 90% USP saline. Cyclophosphamide and Doxorubicin were dissolved in USP saline for dosing. AU treatments were administered i.p. The effect of treatments on tumor growth were analyzed using repeated measures analysis of variance (RM ANOVA), p<0.05 was considered significant.

Figure 29:
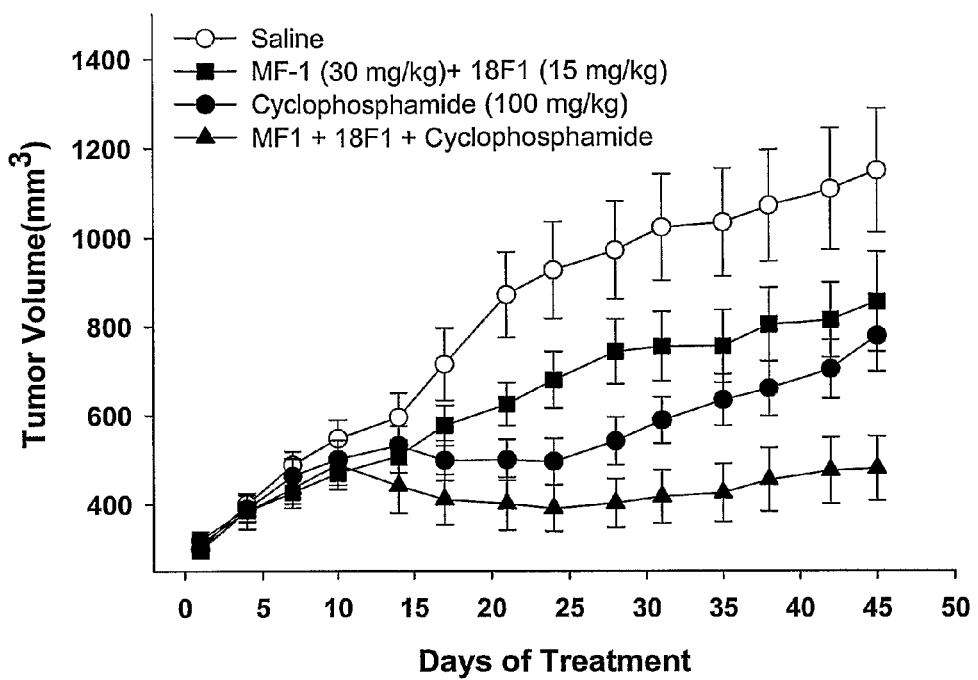
FIG. 29 is a chart plotting tumor growth versus days after treatment with anti-human anti-VEGFR-I antibody 18F1 and anti-mouse anti-VEGFR-I antibody MF1 in combination with cyclophosphamide in MDS-MB-231 xenografts.

As shown in FIG. 29, in the MDA-MB-231 model, adding 18F1+MF1 to an active dose of cyclophosphamide therapy significantly increased the antitumor effect. As shown in FIG. 30, when 5-FU/LV and doxorubicin chemotherapy were administered at certain dose levels, 18F1+MF1 increased the antitumor effects of these two chemotherapies.

hi the DU4475 xenograft model, there was a trend for increased activity (lower T/C %) when IMC-18F1+MF1 was combined with 5-FU/LV, doxorubicin and paclitaxel, although the effect did not reach statistical significance compared to the IMC-18F1+MF1 alone, or cytotoxic agent monotherapy. In MDA-MB-231 this was again the case for doxorubicin, although for 5-FU/LV and paclitaxel there was no trend for increased activity with the combination. The lack of additivity may be due to the minimal effects of 5-FU/LV and paclitaxel as monotherapies at the selected dose levels. The combination with cyclophosphamide also had increased activity in the MDA-MB-435 model (T/C %=51) compared to IMC-18F1+MF1 alone (T/C %=60) or cyclophosphamide monotherapy (T/C %=65), although these differences did not reach statistical significance. This was also the case for doxorubicin and paclitaxel in the same study. Similar to the MDA-MB-231 and MDA-MB-435 data above, a combination of BVIC-18F1, MF1, and cyclophosphamide exhibited increased antitumor activity compared to antibody or cytotoxic therapy alone in a DU4475 xenograft model, although the trend did not reach statistical significance.

Statistical Analysis

Tumor volumes and analysis of in vitro tumor cell growth were analyzed using Student's t test using the SigmaStat statistical package (v. 2.03; Jandel Scientific, San Rafael, Calif.). Differences of p<0.05 were considered statistically significant.

Example 13

Cloning and Sequencing of VH/$V_L$ Regions of Anti-VEGFR-I Antibodies

Poly (A+) mRNA was isolated from hybridoma cells producing clones 6F9, 13G12, 15F11, and 18F1 derived from VEGFR-I immunized KM mice using a Fast-Track kit (Invitrogen, Carlsbad, Calif.). The generation of random primed cDNA was followed by polymerase chain reaction (PCR) using a Clontech kit. Primers (forward: [SEQ ID NO. 53]5'-ATGGAGTTTGGGCTGAGCTG and reverse: [SEQ ID NO. 54]3'-TGCCAGGGGGAAGACCGATGG) and (forward: [SEQ ID. NO. 55]5'-ATG GAA ACC CCA GCG CAG CTT CTC and reverse: [SEQ ID NO. 56]3'-CGGGAAGATGAA-GACAGATG) were used for binding to variable regions of heavy and kappa light chains, respectively. Sequences of human immunoglobulin-derived heavy and kappa chain transcripts from hybridomas were obtained by direct sequencing of PCR products generated from poly (A+) RNA using the primers described above. PCR products were also cloned into pCR2.1 using a TA cloning kit (Invitrogen, Carlsbad, Calif.) and both strands were sequenced using Prism dye-terminator sequencing kits and an ABI 3730 Sequencer (GENEWIZ, North Brunswick, N.J.). All sequences were analyzed by alignments to the Kataman antibody sequence program using the DNASTAR software.

Table 2, above, shows amino acid sequences of the light and heavy chain variable regions of anti-VEGFR-I antibody clones 6F9, 13G 12, 15F11, and 18F1. The sequences of CDR1, CDR2, and CDR3 domains are indicated by underlining. Table 3, above, shows nucleotide sequences of the cDNA encoding the heavy and light chain variable regions of clones 6F9, 13G12, 15F11, and 18F1

Example 14

Engineering and Expression of Human IgG1 Anti-VEGFR-I Antibodies

The DNA sequences encoding the heavy and light chain variable regions of the anti-VEGFR-1 antibody clones 6F9, 13G12, 15F11, and 18F1 were amplified by PCR for cloning into expression vectors. The heavy chain variable regions were fused in frame to the human immunoglobulin heavy chain gammal constant region in vector pEEó.1 (Lonza Biologies pic, Slough, Berkshire, UK). The entire human light chain cDNA was cloned directly into vector pEE12.1 (Lonza Biologies PLC, Slough, Berkshire, UK). Engineered immunoglobulin expression vectors were stably transfected in NSO myeloma cells by electroporation and selected in glutamine synthetase selection medium. Stable clones were screened for antibody expression by anti-Fc and VEGFR-I specific binding ELISA. Positive clones were expanded into serum-free medium culture for antibody production in spinner flasks or bioreactors for a period of up to two weeks. Full length IgG1 antibody was purified by protein A affinity chromatography (Poros A, PerSeptive Biosystems Inc., Foster City, Calif.) and eluted into a neutral buffered saline solution.

The foregoing description and examples have been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. An isolated human monoclonal antibody or binding fragment thereof that binds specifically to human VEGFR-1 comprising a CDRL1 having the sequence RASQSVSSSYLA (SEQ ID NO:4), a CDRL2 having the sequence GASSRAT (SEQ ID NO:2), a CDRL3 having the sequence QQYGSSPLT (SEQ ID NO:3), a CDRH1 having the sequence GFAFSSYGMH (SEQ ID NO: 11), a CDRH2 having the sequence VIWYDGSNKYYADSVRG (SEQ ID NO:12), and a CDRH3 having the sequence DHYGSGVHHYFYYGLDV (SEQ ID NO:13).

2. A method of inhibiting phosphorylation of human VEGFR-1 in a human comprising administering an effective amount of an antibody or binding fragment thereof of claim 1.

3. A method of inhibiting angiogenesis in a human comprising administering an effective amount of an antibody or binding fragment thereof of claim 1.

4. A method of reducing tumor growth in a human comprising administering an effective amount of an antibody or binding fragment thereof of claim 1.

5. The method of claim 4, wherein the method further comprises administering an anti-neoplastic agent.

6. The method of claim 4, wherein the tumor is a breast tumor.

* * * * *

UNITED STATES PATENT AND TRADEMARK OFFICE
CERTIFICATE OF CORRECTION

| | |
|---|---|
| PATENT NO. | : 7,972,596 B2 |
| APPLICATION NO. | : 11/719677 |
| DATED | : July 5, 2011 |
| INVENTOR(S) | : Yan Wu et al. |

It is certified that error appears in the above-identified patent and that said Letters Patent is hereby corrected as shown below:

On the coversheet of the Patent, Field (75) Inventors: delete the name "Danny" and substitute --Daniel-- therefor.

Signed and Sealed this
Sixteenth Day of August, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,972,596 B2 | Page 1 of 1 |
| APPLICATION NO. | : 11/719677 | |
| DATED | : July 5, 2011 | |
| INVENTOR(S) | : Wu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Fifteenth Day of November, 2011

David J. Kappos
*Director of the United States Patent and Trademark Office*